(12) United States Patent
Maggiore

(10) Patent No.: US 10,119,108 B2
(45) Date of Patent: Nov. 6, 2018

(54) MANUFACTURING WITHIN A SINGLE-USE CONTAINER

(71) Applicant: Sartorius Stedim Biotech GmbH, Goettingen (DE)

(72) Inventor: Frank Maggiore, Port Jefferson Station, NY (US)

(73) Assignee: Sartorius Stedim Biotech GmbH, Goettingen (DE)

( * ) Notice: Subject to any disclaimer, the term of this patent is extended or adjusted under 35 U.S.C. 154(b) by 180 days.

(21) Appl. No.: 14/927,848

(22) Filed: Oct. 30, 2015

(65) Prior Publication Data

US 2016/0068793 A1 Mar. 10, 2016

Related U.S. Application Data

(63) Continuation-in-part of application No. 13/956,990, filed on Aug. 1, 2013, now Pat. No. 9,505,173.

(51) Int. Cl.
   *B29C 64/227* (2017.01)
   *C12M 3/00* (2006.01)
   (Continued)

(52) U.S. Cl.
   CPC ............... *C12M 21/08* (2013.01); *B25J 9/10* (2013.01); *B25J 9/14* (2013.01); *B25J 21/00* (2013.01);
   (Continued)

(58) Field of Classification Search
   CPC ... B29C 64/20; B29C 64/205; B29C 64/2227; B29C 64/227; B29C 64/232;
   (Continued)

(56) References Cited

U.S. PATENT DOCUMENTS

2004/0118309 A1  6/2004  Fedor et al.
2009/0229671 A1  9/2009  Hartnett et al.
(Continued)

OTHER PUBLICATIONS

Skaret, Lars, "A Stewart Platform Based Replicating Rapid Prototyping System with Biologically Inspired Path-Optimization", May 2, 2011, University of Oslo Department of Informatics, Master Thesis, pp. 1-48. (Year: 2011).*

(Continued)

*Primary Examiner* — Seyed Masoud Malekzadeh
*Assistant Examiner* — Lawrence D Hohenbrink, Jr.
(74) *Attorney, Agent, or Firm* — Gerald E. Hespos; Michael J. Porco; Matthew T. Hespos

(57) ABSTRACT

A manufacturing assembly has at least a sterilizable chamber containing at least one of a three-dimensional printing device (additive manufacturing), a Computer Numerical Controlled (CNC) finishing head (subtractive manufacturing), a vacuum-forming unit, an injection-molding unit, a laser-cutting unit, a ultrasonic-welding unit, a robotic arman analysis device, a sampling device or a combination thereof. A plurality of individual sterilizable chambers may be aseptically connected into a network of sterilizable chambers that provides additional functionality for the manufacturing assembly. A sterilizable printer assembly may include at least one printing head, a printing platform, and a driving mechanism adapted to perform a movement of the at least one printing head relative to the printing platform along three degrees of freedom; a printer housing enclosing the printer assembly in a sterile manner, at least one aseptic connector fluidly connected to a corresponding one of the at least one printing head.

3 Claims, 37 Drawing Sheets

(51) Int. Cl.
| | |
|---|---|
| C12M 1/36 | (2006.01) |
| C12M 1/00 | (2006.01) |
| C12M 1/12 | (2006.01) |
| C12M 1/34 | (2006.01) |
| B25J 9/10 | (2006.01) |
| B25J 9/14 | (2006.01) |
| B25J 21/00 | (2006.01) |
| B33Y 30/00 | (2015.01) |
| B33Y 40/00 | (2015.01) |
| B29C 64/232 | (2017.01) |
| B29C 64/236 | (2017.01) |
| B29C 67/00 | (2017.01) |
| B29C 64/321 | (2017.01) |
| B29C 64/25 | (2017.01) |
| B29C 64/20 | (2017.01) |
| B29C 64/364 | (2017.01) |
| B29C 64/379 | (2017.01) |
| B29C 64/307 | (2017.01) |
| B29C 64/205 | (2017.01) |
| B29C 64/209 | (2017.01) |

(52) U.S. Cl.
CPC .......... *B29C 64/227* (2017.08); *B29C 64/232* (2017.08); *B29C 64/236* (2017.08); *B29C 67/0059* (2013.01); *B29C 67/0085* (2013.01); *B33Y 30/00* (2014.12); *B33Y 40/00* (2014.12); *C12M 25/00* (2013.01); *C12M 29/00* (2013.01); *C12M 41/12* (2013.01); *C12M 41/40* (2013.01); *C12M 41/48* (2013.01); *B29C 64/20* (2017.08); *B29C 64/205* (2017.08); *B29C 64/209* (2017.08); *B29C 64/25* (2017.08); *B29C 64/307* (2017.08); *B29C 64/321* (2017.08); *B29C 64/364* (2017.08); *B29C 64/379* (2017.08); *Y10S 901/19* (2013.01); *Y10S 901/22* (2013.01)

(58) Field of Classification Search
CPC ..... B29C 64/236; B29C 64/25; B29C 64/307; B29C 64/321; B29C 64/364; B29C 64/379; B29C 67/0059; B29C 67/0085; B29C 67/0081; B33Y 30/00; B33Y 40/00
USPC ............................. 425/174.4, 375; 264/308
See application file for complete search history.

(56) References Cited

U.S. PATENT DOCUMENTS

| | | | |
|---|---|---|---|
| 2010/0206224 A1* | 8/2010 | Thurner | B29C 64/106 118/620 |
| 2014/0208731 A1* | 7/2014 | Shepherd | B25J 9/1075 60/327 |
| 2017/0072632 A1* | 3/2017 | Page | G05B 19/4099 |

OTHER PUBLICATIONS

Chinese Office Action dated Jul. 3, 2017.

* cited by examiner

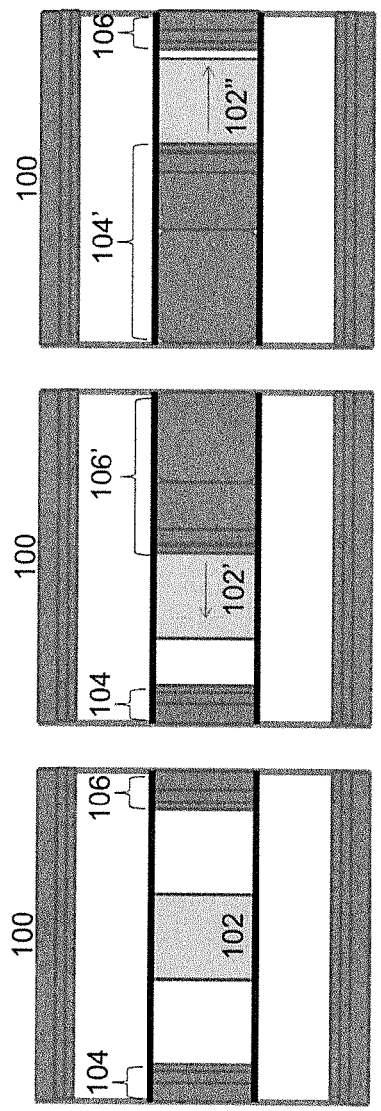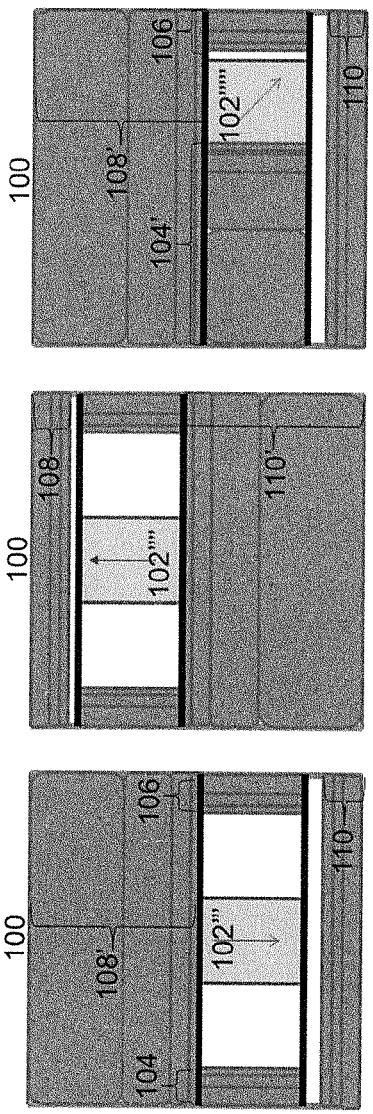
Fig. 3A  Fig. 3B  Fig. 3C
Fig. 3D  Fig. 3E  Fig. 3F

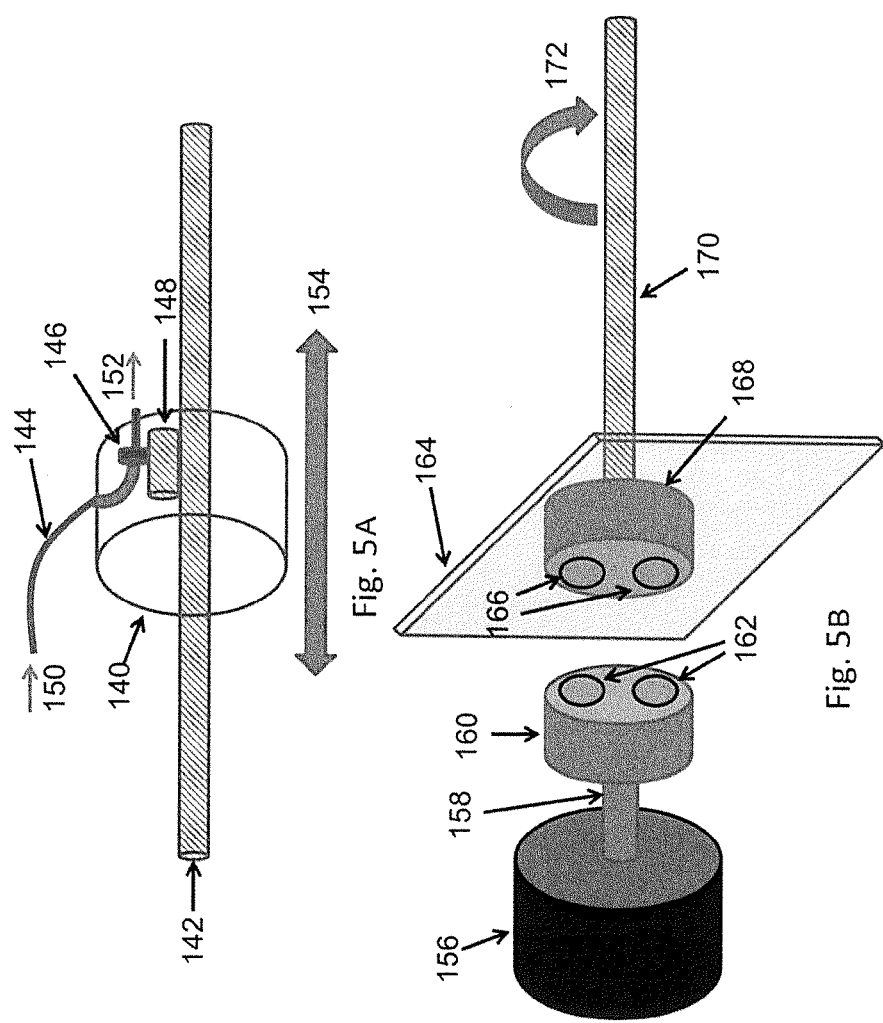

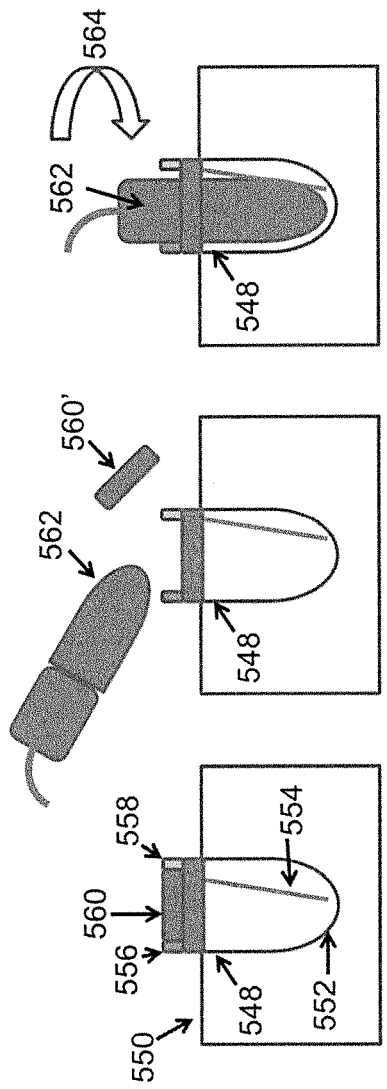

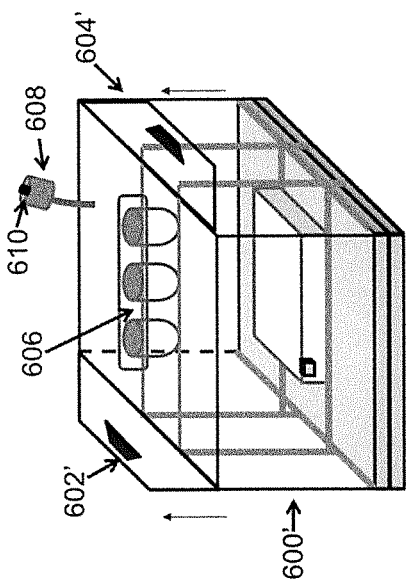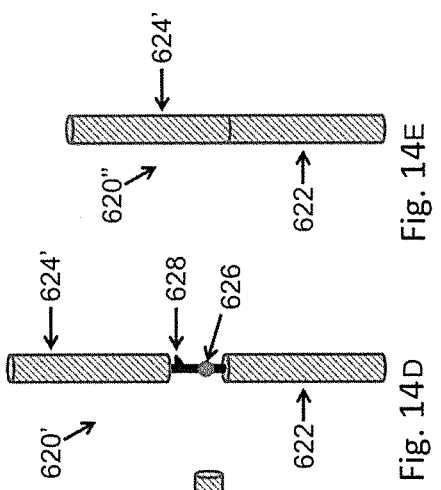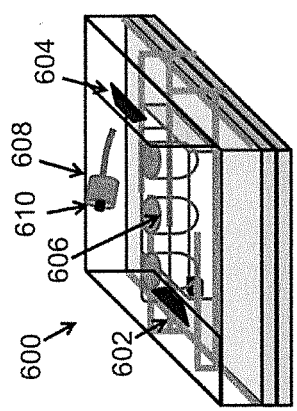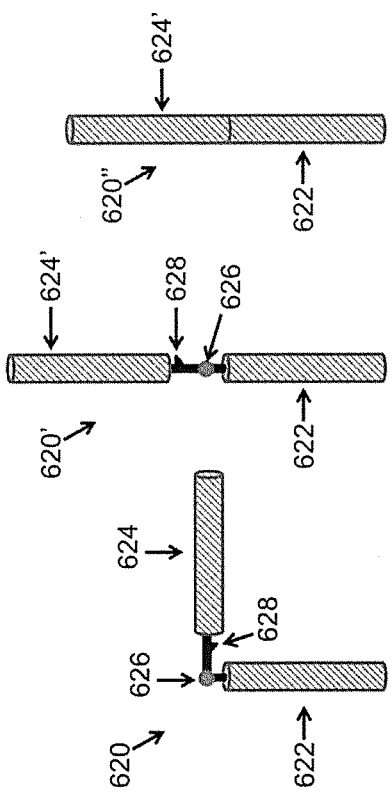

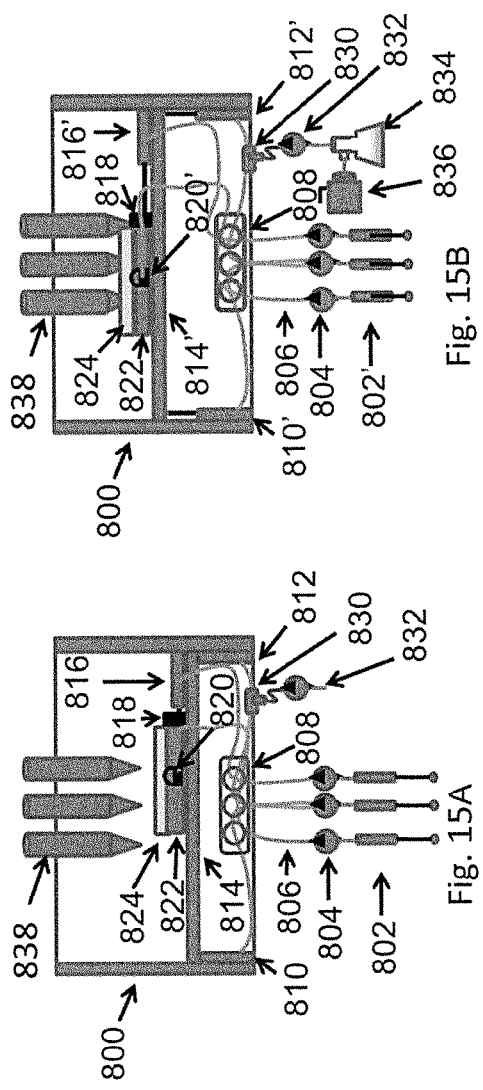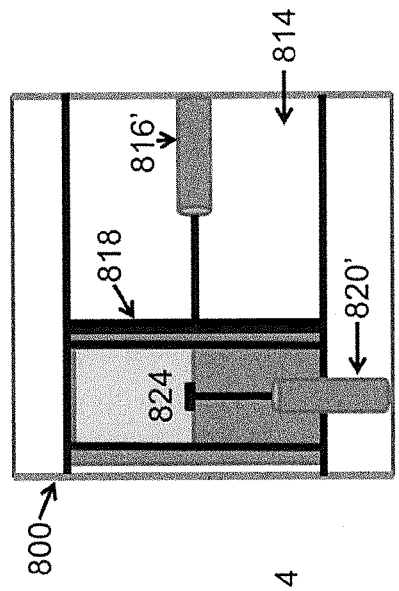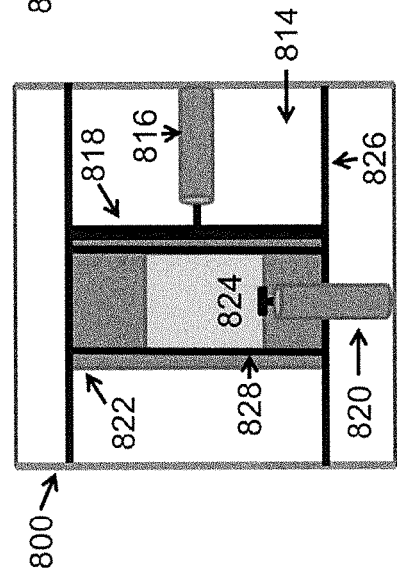

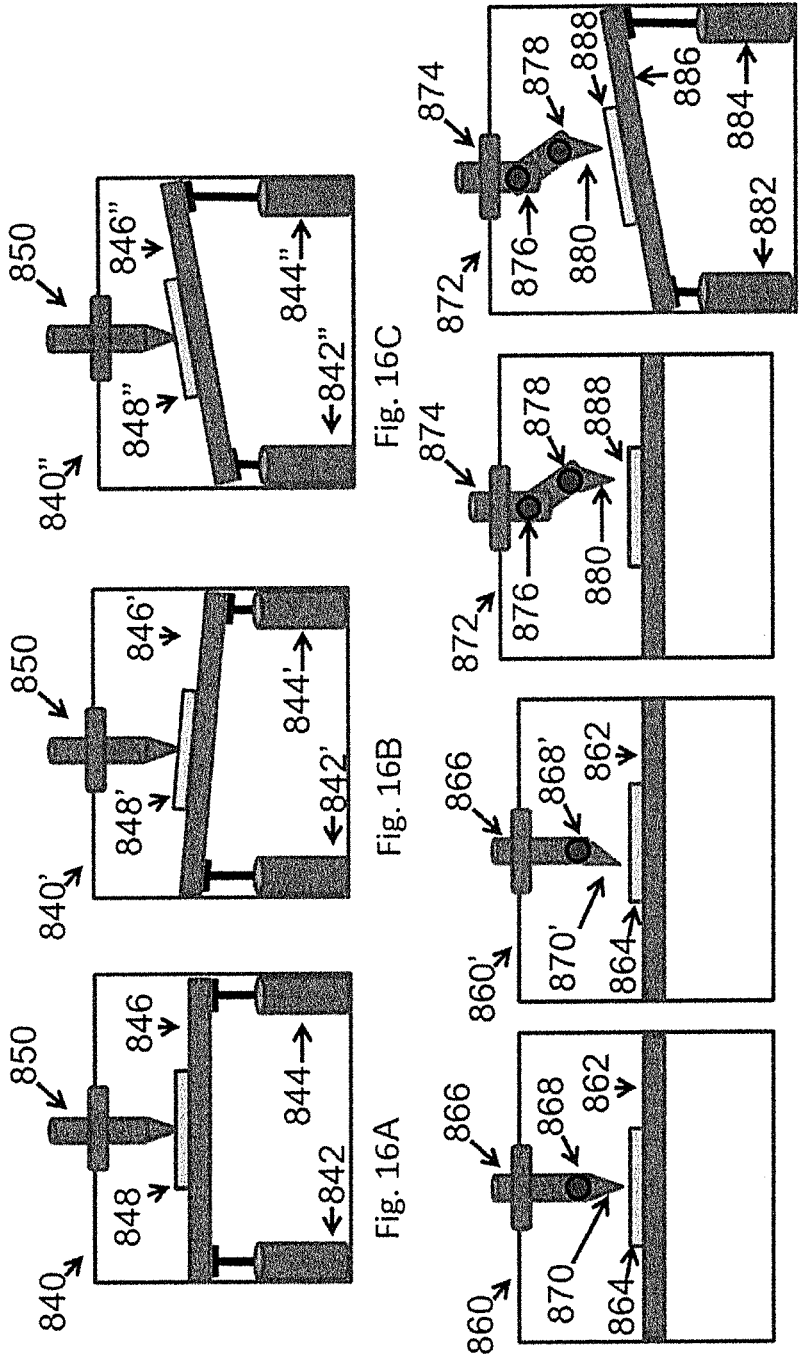

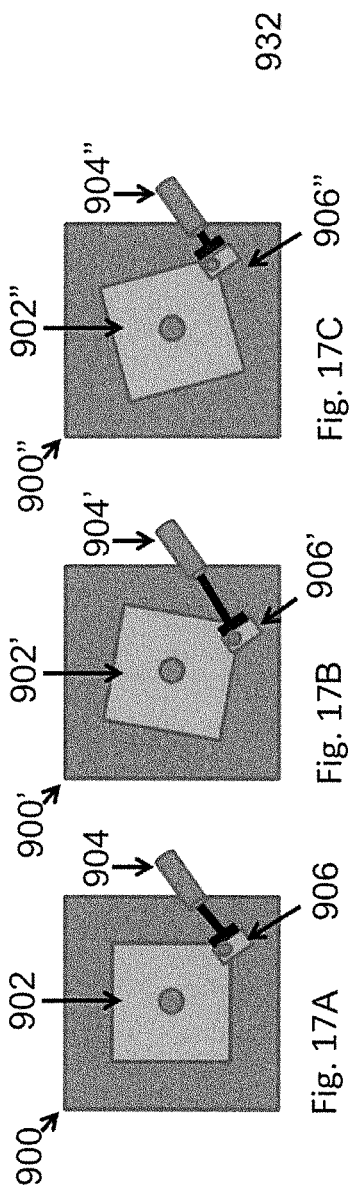

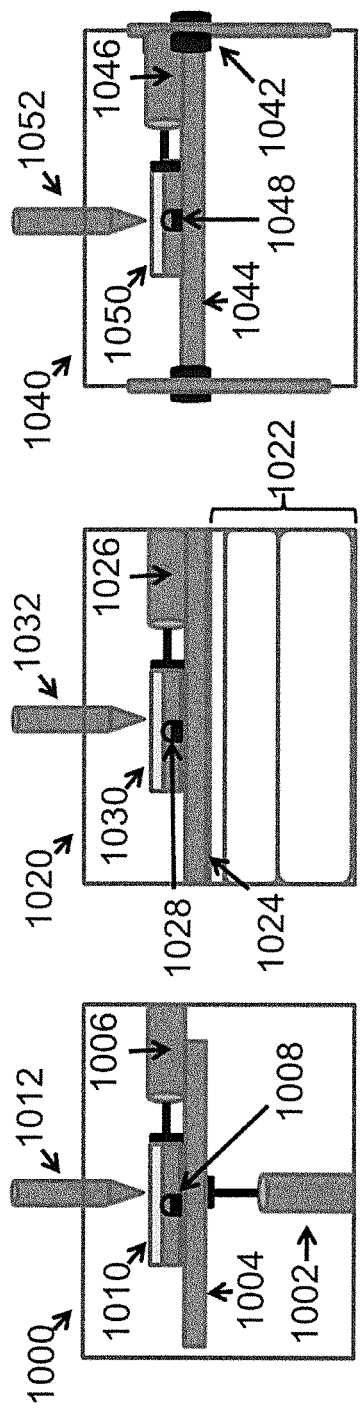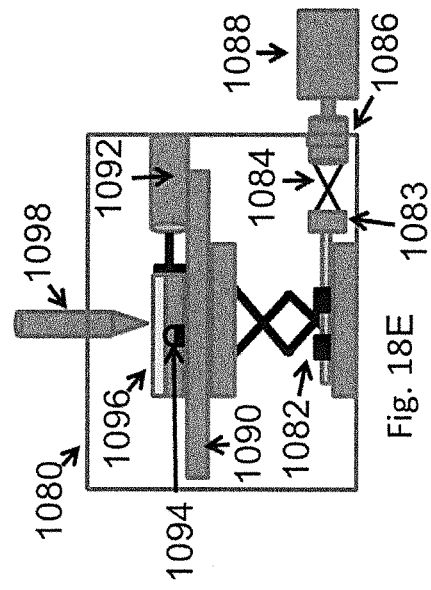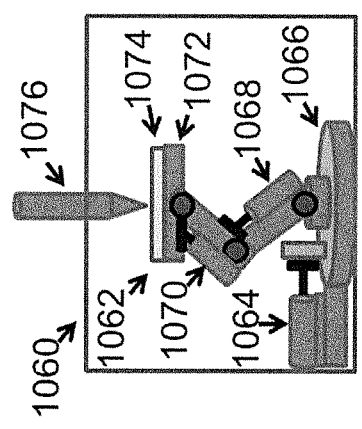

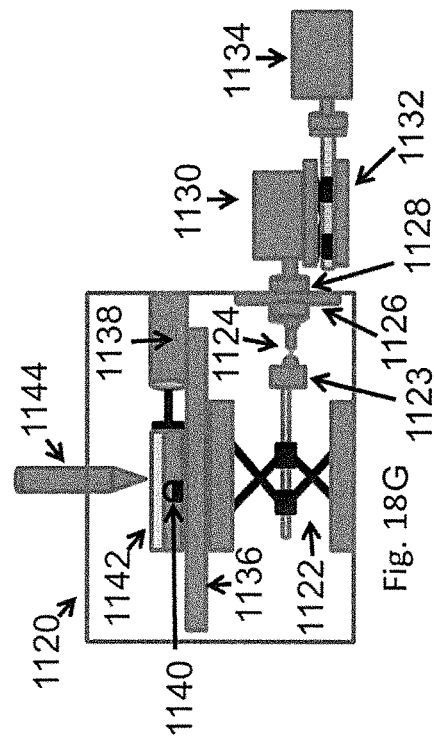
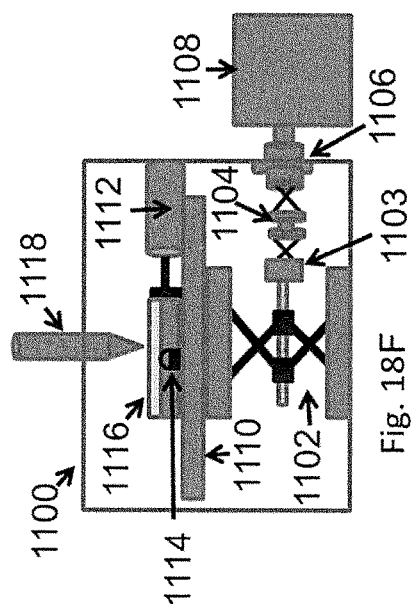
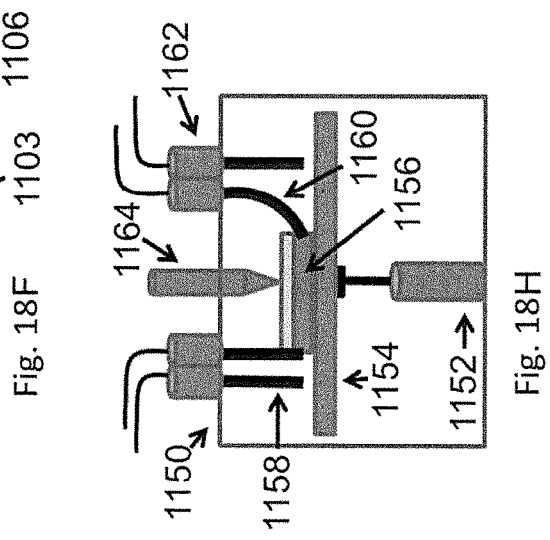
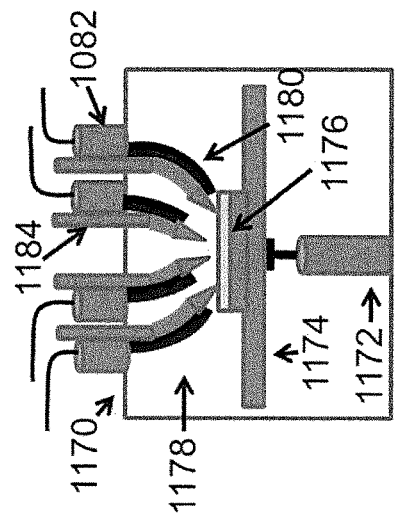

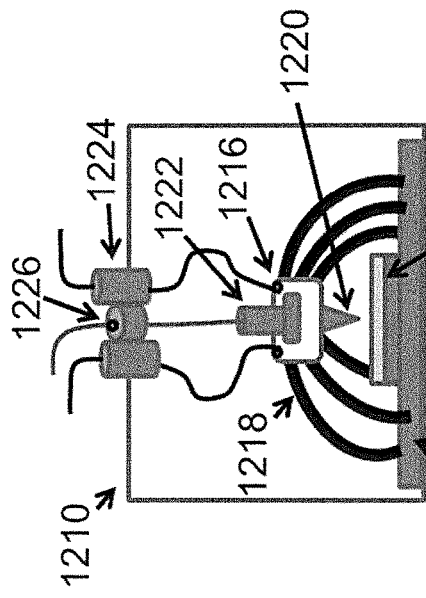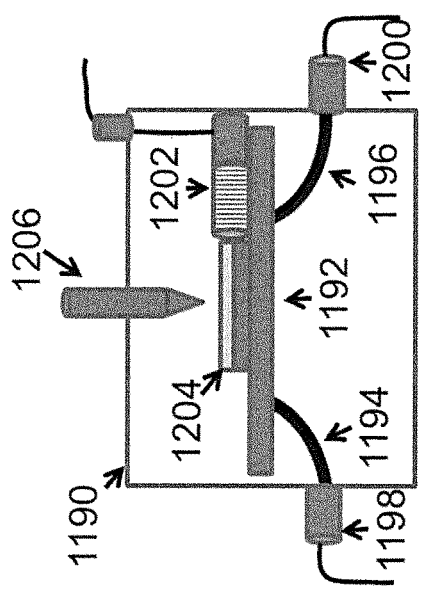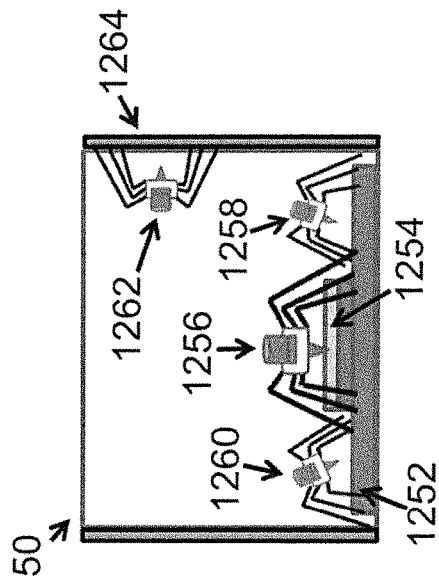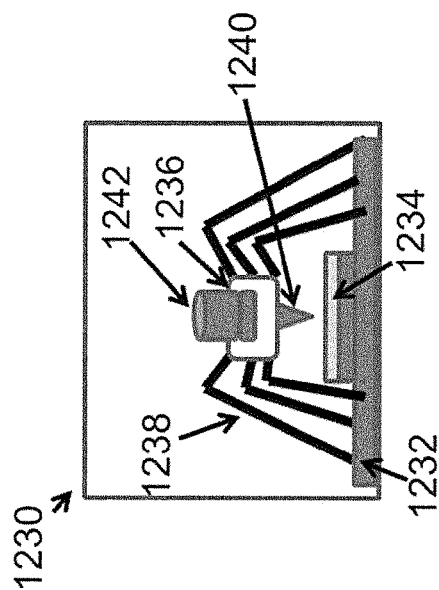

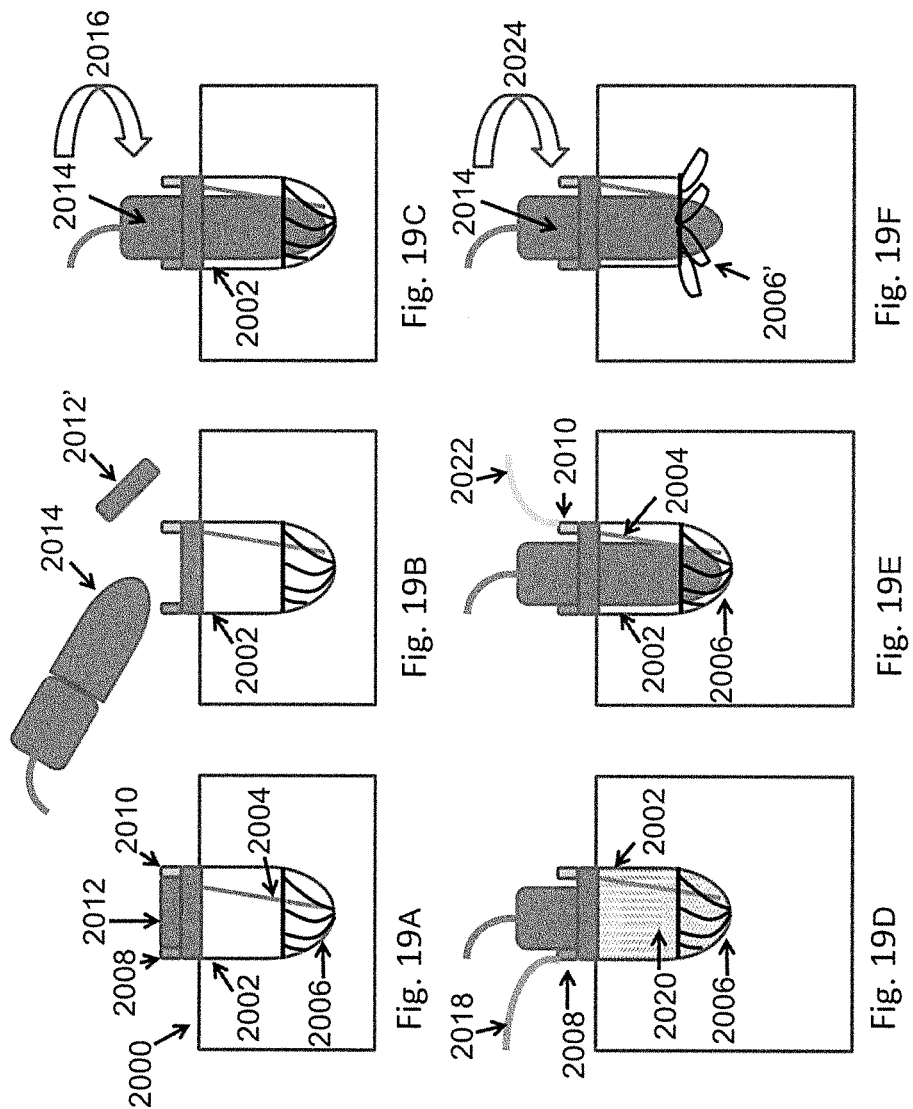

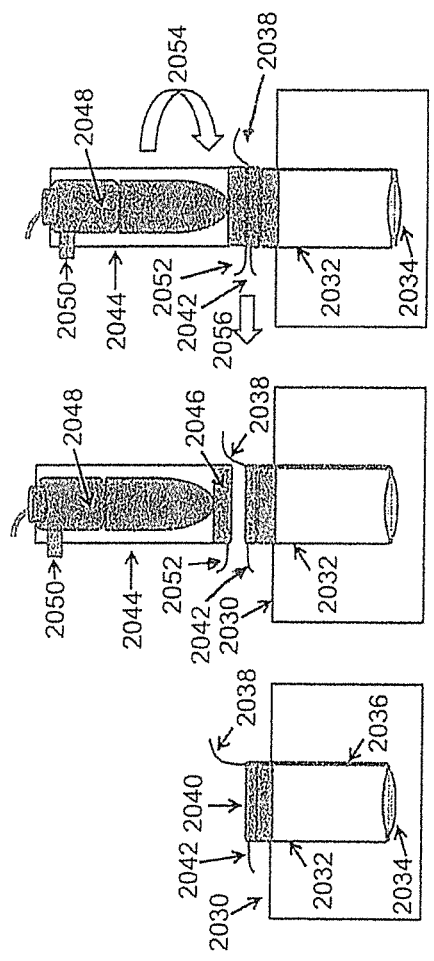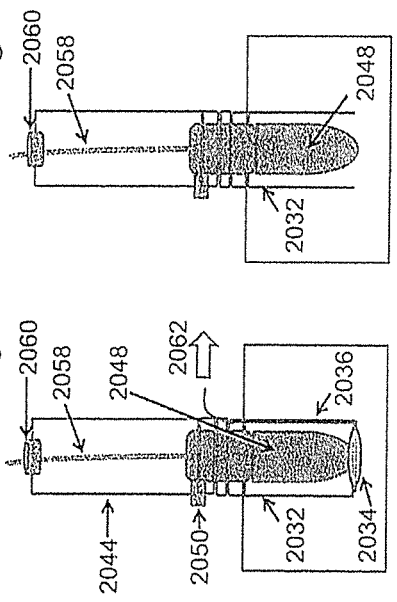

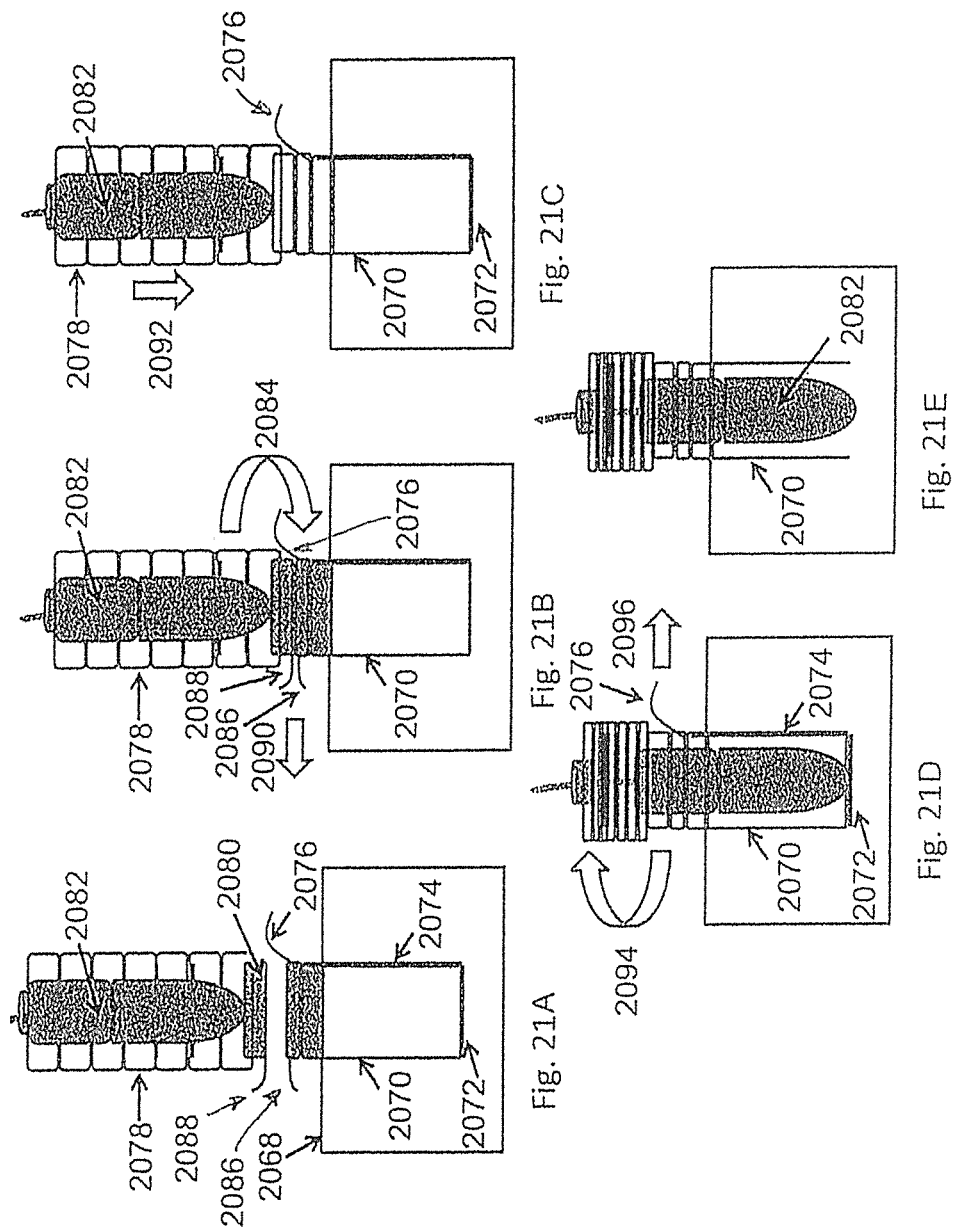

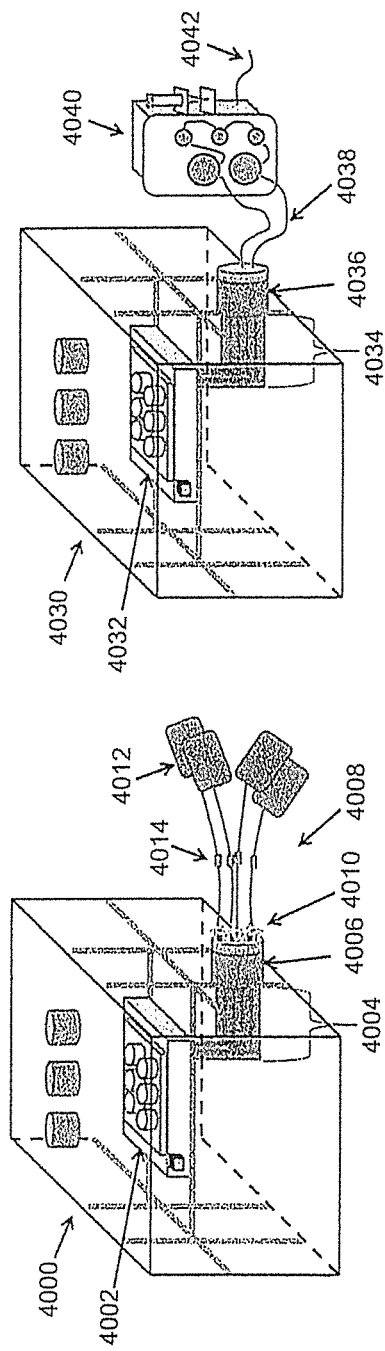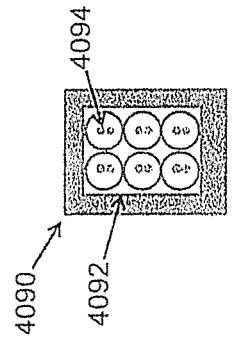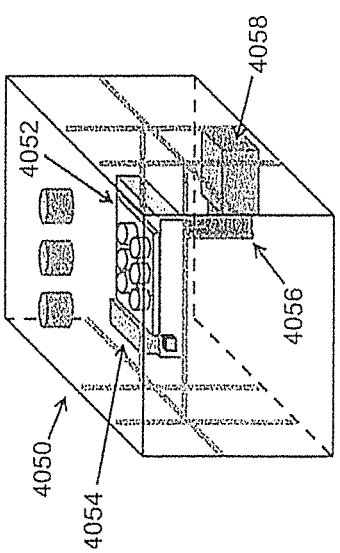

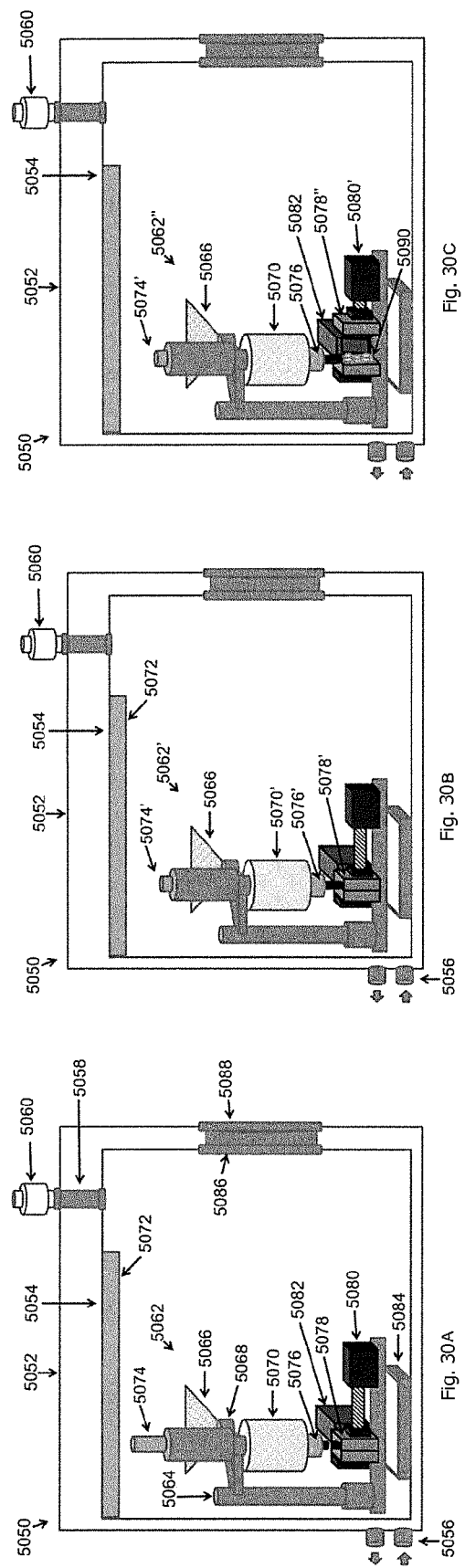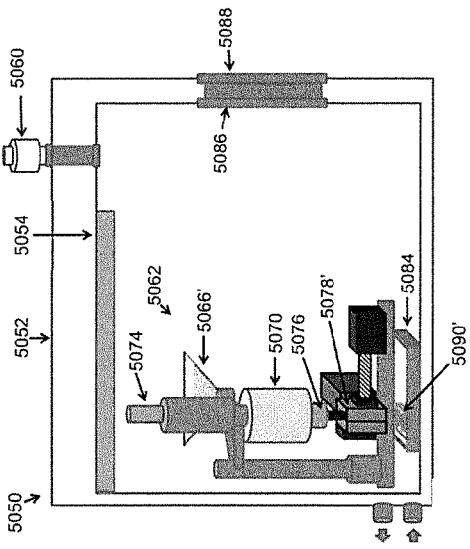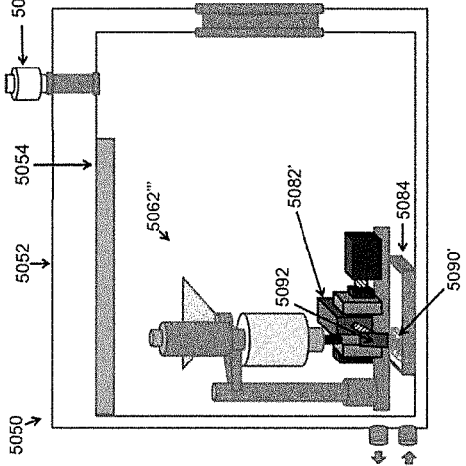

MANUFACTURING WITHIN A SINGLE-USE CONTAINER

BACKGROUND

1. Field of the Invention

The invention relates to manufacturing methods for use inside of a sterile/sterilizable single-use three-dimensional container or chamber, manipulation of the manufactured products, and coating, growing, or integrating biologically active materials with those manufactured products.

2. Description of the Related Art

The forming of three-dimensional objects or the coating of three-dimensional objects under sterile conditions, particularly a coating with biochemical materials, requires high effort to uphold the sterile conditions and to assemble the required apparatuses for forming or coating under sterile conditions.

Thus, it is a problem to provide a manufacturing device, a manufacturing system and manufacturing methods that are capable to form, cut, print, or coat a material under sterile conditions in a reliable and easy manner.

SUMMARY OF THE INVENTION

The manufacturing operations performed in the systems and/or devices described in the following may be performed relative to a sterile/sterilizable chamber, in that the operations may take place within the sterilized chamber or be carried out in relation to the dimensions or walls of the chamber. One aspect of the invention relates to a manufacturing device that is a three-dimensional printing device comprising a sterilizable printer assembly including at least one printing head, a printing platform, and a driving mechanism adapted to achieve a relative displacement between the at least one printing head and the printing platform along two or three degrees of freedom. A printer housing encloses the printer assembly in a sterile manner, and at least one aseptic connector is fluidly connected to a corresponding one of the at least one printing head.

The printer assembly is intended for single-use applications, and, thus, is disposable after use. Preferably, the three-dimensional printing device is disposable with the inclusion of the printer housing after a single use. The printer housing can comprise a rigid or flexible wall, and is preferably made of a sterilizable material. An external structural assembly, such as a stainless steel support container, may be utilized to provide rigid support to a flexible-walled printer housing. An example of a printer housing may be a sterile or sterilizable chamber.

The printer assembly is sterile or sterilizable, e.g. by gamma-irradiation, autoclaving, or chemical sterilant such as ethylene oxide or vaporized hydrogen peroxide.

The printer assembly may comprise a single printing head or a plurality of printing heads. Each of the printing heads can utilize a specific technique of additive manufacturing such as extrusion, fused deposition modeling, heated extrusion, spray deposition, granular material binding, photopolymerization, etc. The printing heads are adapted for the deposition of the materials onto a printing platform or printing tray or any object located thereon. A three-dimensional computer-aided design (CAD) file can be utilized to serve as the instructions for building the three-dimensional printed structure. By depositing the appropriate printing material, three-dimensional objects may be created or formed. Other appropriate printing material may be used for coating two-dimensional or three-dimensional objects. The printer assembly may be utilized for the dispensing of nutrient media or the metered dosing of at least one drug product.

In order to print the three-dimensional object, it can be sufficient to allow a relative displacement between the at least one printing head and the printing platform along two degrees of freedom, wherein the third dimension of the object is created during by depositing printing material. A displacement of the printing platform and the at least one printing head along three degrees of freedom is an option. In order to obtain the relative displacement the at least one printing head or the printing platform can be moved. Particularly, the driving mechanism is adapted to perform a movement of the at least one printing head relative to the printing platform along at least two or three degrees of freedom. Alternatively, the driving mechanism is adapted to perform a movement of the printing platform relative to the at least one printing head along two or three degrees of freedom.

A finishing head can be utilized to subtractively remove material from the three-dimensional object after the additive manufacturing steps have been completed. Debris generated from the subtractive process can be flushed into a debris tray with a fluid media and filtered out during a recirculation of the fluid within the debris tray.

Optionally, the aseptic connector of the three-dimensional printer comprises a single-use aseptic connector, where a sterile connection and the sterile fluid transfer can occur between at least two connected complementary aseptic connectors. The aseptic connector can additionally comprise a thermoplastic tubing, which can be heat-connected in a sterile manner to a complementary aseptic connector. The heat-connection can be performed by at least one of welding, ultrasonic welding, partial melting and gluing with a thermoplastic glue.

Optionally, the internal volume of the printer housing is fluidly connected with the exterior by means of a venting filter. The venting filter may be a sterilizing grade vent filter in order to keep the interior of the printer housing in a sterile condition. The interior of the printer housing enclosing the printer assembly can be filled with a homogenous or heterogeneous gas mixture such as compressed air, nitrogen, carbon dioxide, or other mixtures and can be vented to the exterior utilizing a venting filter, preferably a sterilizing-grade vent filter.

Optionally, the at least one printing head is in a fixed position and the printing platform can be moved along two or three degrees of freedom. A degree of freedom can be a movement along a linear axis or a rotation around a rotational axis. Thus, the three degrees of freedom may comprise three rotational axes or may comprise two rotational axes and one linear axis or may comprise one rotational axis and two linear axes or may comprise three linear axes. Preferably, the degrees of freedom are all linear axes, which are orthogonal to each other, and thus, the axes are defining a cartesian coordinate system.

Optionally, the at least one printing head is in a fixed position and the printing platform can be moved along multiple degrees of freedom, such as more than three degrees of freedom or more than six degrees of freedom. Multiple degrees of freedom for the printing platform and/or the printing head can be achieved by linkage mechanisms and/or joints, which enable articulation along a plurality of angles by combining movements along a linear axis and/or rotations around a rotational axis of multiple rigid bodies connected together. Thus, the degrees of freedom may be increased to allow manufacturing by printing at a plurality of angles within a three-axis coordinate system.

Optionally, the at least one printing head is in a fixed position and contains a plurality of articulating joints which may position the dispensing printing head along multiple degrees of freedom relative to the printing platform.

Optionally, the at least one printing head of the three-dimensional printer is in a fixed position and the printing platform can be moved along multiple degrees of freedom. The printing platform may be moved along the axis framework utilizing a pneumatic actuator, a hydraulic actuator, an electric actuator, or a magnetic actuator.

Optionally, the pneumatic/hydraulic actuator comprises at least one bag or bladder, which is extendible in at least one direction by providing a fluid pressure to the inside of the at least one bag or bladder. In order to obtain a precise movement and positioning of the printing platform by means of the pneumatic/hydraulic actuator, the actuator may comprise a coarse bag and a fine bag, wherein the coarse bag is more extendible in at least one direction than the fine bag, when filled with an identical volume of a fluid or when the same internal fluid pressure is applied to the bags. Additionally, the printing platform can contain a plurality of coarse and fine bags, which can be utilized to automatically level and calibrate the distance between the printing platform and the printing head in use.

Optionally, the pneumatic/hydraulic actuator may comprise at least one of linear actuators, rolling diaphragm actuators, sterilizable linear actuators, sterilizable syringes, compressible cylinder, hydraulic rotary actuator, and hydraulic rotary vane actuators that are extendible in at least one direction by providing a fluid pressure to the inside of the actuating unit. In order to obtain a precise movement and positioning of the printing platform by means of the pneumatic/hydraulic actuator, the actuator may comprise a coarse actuator and a fine actuator, wherein the coarse actuator is more extendible in at least one direction than the fine actuator, when filled with an identical volume of a fluid or when the same internal fluid pressure is applied to the actuators. Additionally, the printing platform can contain a plurality of coarse and fine actuators, which can be utilized to automatically level and calibrate the distance between the printing platform and the printing head in use. To reduce the friction between components, the actuators may utilize rolling diaphragms to reduce the loss of force transferred via friction and to respond to changes in force with higher precision and more immediate feedback.

As an option, the pneumatic/hydraulic actuator may push and/or pull at least one printing tray across the printing platform along a plurality of tracks. The plurality of tracks may serve as guides for the positioning of the at least one printing tray platform relative to the at least one printing head.

As an option, the pneumatic/hydraulic actuator may comprise at least one fluidactuated motor that moves along a track or a threaded screw for positioning the printing platform along a corresponding axis. The fluid actuating the motor may comprise any gas or gas-liquid-mixture. Particularly, the fluid can comprise air, nitrogen, or any inert gas.

As a further option, the three-dimensional printer can comprise a magnetic actuator comprising at least one magnetic drive mechanism, which is rotatable or linearly movable by a complementary external magnetic drive mechanism.

As a further option, the three-dimensional printer may comprise a plurality of actuators formed into a robotic arm for positioning the printing platform at a plurality of positions and a plurality of angles relative to the at least one printing head.

As a further option, the three-dimensional printer may comprise a platform jack, which may convert rotational force into a linear motion. The platform jack may be utilized to control the positioning of the printing platform or printing tray. The platform jack screw may be rotatable by a complementary external magnetic drive mechanism. An internal extension assembly may be utilized to maintain a connection to transfer the force from the external assembly to the platform jack screw even as the screw position is changed by the movement of the assembly during extension and/or retraction.

As a further option, the three-dimensional printer may comprise a plurality of soft robotic actuators, where the soft material is actuated when pressurized with hydraulic and/or pneumatic pressure. The soft robotic actuators may be formed to move the at least one printing tray along the printing platform and/or move the at least one printing head into position above the at least one printing tray.

As a further option, the three-dimensional printer may comprise at least one untethered multiaxis printing device, where the device is self-contained and internal to the sterile chamber. The untethered multiaxis printing device positions itself on a static and/or fixed printing tray on the printing platform. The untethered multiaxis printing device may contain a plurality of fluid reservoirs and an internal drive mechanism to power the positional movement of the device above the printing tray.

Optionally, the three-dimensional printer comprises a position tracking system, also called precision tracking system, which is capable to determine the position of the printing platform relative to the at least one printing head along each of the three degrees of freedom. Thus, one or more of the coordinates of the printing platform within the three axis framework can be measured precisely by means of the tracking system. In order to obtain a maximum accuracy of positioning the printing platform along one or more of the framework axes a plurality of (magnetic, hydraulic, or pneumatic) actuators can be utilized along the same axis of freedom. Particularly, two or more actuators may actuate a corresponding track or threaded screw in order to provide coarse to fine resolution for movement of the printing platform. A position controller may be provided to control and auto-correct the movement of the actuators to position the printing platform to the exact coordinates required for the deposition of material by the at least one printing head.

The tracking system can include a laser tracking system, comprising an external laser source arranged exterior to the three-dimensional printer assembly, a mirror or reflective material on at least one portion of the printing platform, a laser detecting device, for detecting the time and angle of the reflected laser emission, and a computing system to calculate and report the coordinates of the printing platform relative to the at least one printing head.

Alternatively, the tracking device can comprise a plurality of cameras exterior to the three-dimensional printer assembly, a visual target material on at least one portion of the printing platform, and a computing system to calculate and report the coordinates of the printing platform relative to the at least one printing head. The cameras may be macro cameras with high resolution, such as HDTV cameras or generally cameras having a horizontal resolution of 1000 pixels or more.

Optionally, the three-dimensional printer comprises a transfer hatch adapted for removing the printing platform containing the three-dimensional printed object. By means of the transfer hatch objects may be transferred from or into the printer housing in a sterile manner. Thus, the transfer hatch may be formed in the wall of the printer housing. Preferably, the transfer hatch is aseptically connectable to a sterile transfer bag allowing for the printing platform containing the three-dimensional printed object to maintain sterility during transfer of the printed object.

Optionally, the three-dimensional printer can comprise a membrane dispenser for dispensing a roll or sheets of membrane and which are printable on by means of the printing assembly. By means of the at least one printing head the membranes can be printed with proteins, antibodies, molecules, structural scaffolding or other printing materials. These printing materials might be stored in a tank located in the corresponding printing head within the sterile printer housing or might be provided from an external printing material source via a fluid line. The fluid line can be permanent fixed to the belonging printing head, particularly to keep the printing material and/or the printing head sterile. Alternatively, the fluid line can be removably connected to the belonging printing head, e.g. by a sterile connector.

The membrane dispenser can be driven hydraulically, pneumatically or magnetically. In order to be able to manufacture membrane of different sizes and shapes, the three-dimensional printer might further comprise a membrane cutter for cutting the roll or sheets of membrane into strips, sections, shapes, or pieces. The membrane cutter might be passive or active. A passive membrane cutter can comprise one or more fixed blade(s), thus utilizing the dispensing of the membrane roll to cut the membrane into strips utilizing the static blade(s) or a cutting die. An active membrane cutter can comprise one or more movable or rotatable blade(s), and thus, utilizing a mechanical motion of the blade(s) to cut the membrane, wherein the blades might be driven by a hydraulic/pneumatic actuator or an external magnetic drive mechanism.

Optionally, the three-dimensional printer further comprises a collection device for collecting the strips, sections, shapes, or pieces cut from the membrane, wherein the collection device can be moveable along the three axis framework in order to collect the strips etc. at different locations within the printer housing.

Depending on the printing materials, which are printed by means of the at least one printing head, it is required to support the fixation of the printing material. E.g. it might be required for printing material dissolved in aqueous solutions to support the drying process by providing dry air and/or hot air and thermoplastic material might require a cooling, particularly by blowing cool air to the printed material. Therefore, the three-dimensional printer might comprise a drying device for drying the three-dimensional printed object. Particularly, the drying device can comprise a dry air vent for providing air from an external air supply device. As an option, the dry air vent can comprise a sterilizing grade vent filter for filtering the incoming air to keep the interior of the printer housing sterile.

The hot air or cool air may be provided by an external device and flows through the vent into the interior of the printer housing, particularly to the printing platform. The three-dimensional printer may comprise a dispersal mechanism to evenly distribute the hot air or the cold air over the area of the printing platform, especially over the membrane, in order to dry the printed material onto the membrane. The three-dimensional printer may alternatively or additionally comprise a heating or cooling device being a disposable single-use device attached to the printer housing or included by the printer housing.

In order to keep a more or less constant pressure inside the printer housing, the excessive air from the dry air vent might be released into the exterior of the printer housing by means of a vent, particularly, a sterile vent. Correspondingly, waste air from the pneumatic actuators may be released into the printer body housing which is maintained at ambient pressure using the vent. The vent may also act as an air pressure regulating device keeping the interior of the printer housing at ambient pressure or at a predetermined underpressure or overpressure.

In order to keep the temperature inside the printer housing more or less constant at least a part of the printer housing can be formed as a thermal insulation or jacketing. The thermal insulation or jacketing can contain thermal barrier layers to prevent the transfer of heat or comprise tubing or capillaries for pumping a fluid through the insulation for the purposes of maintaining a constant temperature within the three-dimensional printer.

The three-dimensional printer may also comprise a temperature regulation device for maintaining a constant temperature within the printer housing. A temperature regulating device can measure the internal temperature of the three-dimensional printing assembly inside the printer housing and either heat or cool a fluid flowing into the printer housing via the in the printer housing to provide temperature regulation and/or incubation of the printed material.

The three-dimensional printer may also comprise an external temperature regulation device, such as a stainless steel container assembly, for maintaining a constant temperature within the printer housing. An external temperature regulating device may regulate the temperature by recirculating a temperature-controlled fluid inside of a jacketed container. The external temperature regulation device may alternatively utilize temperature controlled plates to provide a temperature exchange with the surface area of the printer assembly. The external temperature regulation device may utilize temperature measurements internal to the printer assembly for temperature regulation control.

The printing platform may be formed as the printing tray or may include the tray, e.g. positioned thereon, which is fillable with a liquid, preferably a nutrient rich liquid, for supplying living cells with an environment for growth during the printing process. The fluid in the tray can be recirculated, mixed, filtered, or drained and replaced according to the requirements of the printed structure.

Optionally an electric charge is providable by the printing platform or at least one printing head. Therefore, each of the at least one printing head(s) and/or the printing platform can comprise an electrode, in order to produce and distribute the small electric charge. A regulated electric charge can be utilized to stimulate cells located on the printing platform, particularly in a tray, during organ growth, incubation, or development.

Optionally, the three-dimensional printer may comprise a leveling device for horizontal leveling of the printing platform. By means of the leveling device it can be ensured that the three-dimensional printer and its printing platform or tray are leveled during the printing process. The leveling device can additionally be used to automatically calibrate the distance between the printing platform and the printing head in use.

The invention also relates to a printing system with a three-dimensional printing device comprising a sterilizable printer assembly including at least one printing head, a printing platform, and a driving mechanism adapted to achieve a relative displacement between the at least one printing head and the printing platform along two or three degrees of freedom.

A printer housing encloses the printer assembly in a sterile manner, and at least one aseptic connector fluidly connected to a corresponding one of the at least one printing head. The printing system also has a control device comprising a complementary driving mechanism adapted to drive a corresponding one of the driving mechanism of the three-dimensional printing device, at least one sterile printing material container fluidly connected with a corresponding one of the at least one aseptic connector and a controller for controlling the movement of the at least one printing head by means of the complementary driving mechanism and for controlling the ejection of the printing material by means of the at least one printing head.

Optionally, the complementary driving mechanism for moving the at least one printing head comprises a complementary magnetic actuator.

Optionally, the complementary magnetic actuator comprises an external motor driving a shaft to which a plurality of magnets is attached. It has to be understood, that a plurality of complementary magnetic actuators may be provided for each degree of freedom or movable axis. Each complementary magnetic actuator may utilize an external motor, preferably a stepper motor, containing a shaft and head with a plurality of magnets. The magnets can be ferrous magnets (such as iron), rare earth magnets (such as Neodymium), superconducting magnets, or magnetic fluids (ferrofluids). At least one magnetic head can mate directly or indirectly with an internal magnetic head of the magnetic actuator being internal and containing a plurality of magnets utilizing a bearing system or rigid wall separation. When the external motor rotates the magnetic connection between the external or internal magnets turns the internal magnetic head which in turn drives the corresponding printing head relative to the printing platform along one degrees of freedom. The driving can be performed by an internal threaded screw which is utilized to precisely move the printing platform along a track and or threaded screw within a three axis framework. This movement of the printing platform tray can be measured precisely with a tracking system. The system can auto-correct the position the printing platform by movement of the external magnetic drive mechanism to the exact coordinates required for the deposition of material by the printing device.

Optionally, the complementary driving mechanism for moving the at least one printing head comprises a controllable pneumatic source. The controllable pneumatic source is preferably an automated integrity testing device. In order to provide only a single controllable pneumatic source, this pneumatic source can be connected to a pneumatic manifold or a pneumatic multiplexer in order to sequentially fluidly connect a single one of a plurality of complementary driving mechanisms to the controllable pneumatic source. The three-dimensional printer, wherein an automated integrity testing device, preferably a Sartocheck® bag integrity testing device with a fine resolution pressure transducer, can be utilized as a measuring and pressure source for the pneumatic driving mechanism, such as a bag or bladder inflation mechanism, for positioning the printing platform/tray to the exact coordinates required for the deposition of printing material by the at least one printing head.

The manifold device linking the tubing from the three-dimensional printer to the measured pressure source can be controlled by the automated integrity testing device or an external device. The manifold device may link the tubing from the three-dimensional printer to the measured pressure source, which can be controlled by the automated integrity testing device or an external device. An electronic control section of manifold device which can be re-used can be externally attached to the sterile section of the manifold device which can be single-use.

Optionally, the printing system comprises a position tracking system, which is capable to determine the position of the printing platform relative to the at least one printing head along each of the three degrees of freedom. The position tracking system is connected to the controller for correcting position of the printing platform to the predetermined coordinates required for the deposition of the printing material by the at least one printing head. The position tracking system is capable to determine the position of the printing platform relative to the at least one printing head along each of the three degrees of freedom. The controller of the printing system can control the driving mechanism, e.g. auto-correct the inflation of the bags, in order to position the printing platform to the exact coordinates required for the deposition of printing material by the printing head.

Optionally, the printing system's three-dimensional printer further comprises a membrane cutter for cutting the roll or sheets of membrane into strips, sections, shapes, or pieces driven by a hydraulic/pneumatic actuator or an external magnetic drive mechanism controlled by the controller.

Optionally, the printing system's three-dimensional printer further comprises a drying device for drying the three-dimensional printed object, wherein the drying device includes an air supply device located outside the printer housing providing air through a vent in the printer housing towards the printing platform. The printing material can be dried utilizing a forced hot air or forced cold air provided by the air supply device through the vent, preferably through a sterilizing grade vent filter for filtering the air flowing into the printer housing. A heating or cooling device can take hot or cold air processed from an external device and can input it into the three-dimensional printing assembly. The heating or cooling device can contain a dispersal mechanism to evenly distribute the hot or cold air over the printing platform or a printed object, such as a membrane, to dry the printed material, e.g. onto the membrane. The heating or cooling device can be a disposable single-use device.

Optionally, the aseptic connector of the three-dimensional printer is fluidly connected to a feed or processing source including at least one of a bioreactor, a fermenter, a filtration train, a cross flow assembly, a membrane adsorber, a column, a centrifugation apparatus, a continuous centrifugation apparatus, an incubator, or other bioprocessing assemblies. The filtration train may include depth filters, pre-filters, sterilizing grade filters, ultra-filters, virus filters, etc. The cross flow assembly may include microfiltration or ultra-filtration cassettes.

The invention further relates to a printing method including the step of providing a three-dimensional printing device comprising a sterilizable printer assembly including at least one printing head, a printing platform, and a driving mechanism adapted to achieve a relative displacement between the at least one printing head and the printing platform along two or three degrees of freedom. A printer housing encloses the printer assembly in a sterile manner, and at least one aseptic connector fluidly connected to a corresponding one of the at least one printing head. The method proceeds by connecting at least one sterile printing material container fluidly with a corresponding one of the at least one aseptic connector, moving the at least one printing head by means of a complementary driving mechanism coupled to the driving mechanism and ejecting printing material by means of the at least one printing head for printing the printing material onto the printing platform or onto an object located on the printing platform under sterile conditions.

In case the printer assembly is not in a sterile condition that printing method may including the step of sterilizing the printer assembly. The sterilization may be carried out by using gamma-irradiation, autoclaving, or a chemical sterilant such as ethylene oxide or vaporized hydrogen peroxide.

In case the printing head is not pre-assembled with the sterilized printer assembly, a printing head assembly that is pre-sterilized, potentially by an alternate sterilization method than is used with the printer assembly, may be aseptically connected to the sterile printer assembly. A non-sterile printing head assembly may be inserted into a connection chamber and sterilized utilizing a chemical sterilant method such as ethylene oxide or vaporized hydrogen peroxide prior to removing the barrier between the printing head assembly and the printer assembly and prior to usage within the printer assembly.

One aspect of the invention relates to a manufacturing device that comprises a robotic arm assembly. The robotic arm assembly is internal to a sterilizable chamber and may comprise at least one actuator, at least one articulating support, at least one gripping assembly, and a driving mechanism adapted to achieve a relative displacement within the sterilizable chamber. The robotic arm assembly may be utilized for moving components and manufactured products from one place to another within a sterile chamber and/or from one sterile chamber to another in a connected network of sterile chambers. The robotic arm assembly may additionally be utilized for stacking and storing items as well as performing assembly of individual components.

The robotic arm assembly and the internal components making up the assembly, including the plurality of actuators, supports, articulations, seals, and plastic covering materials are sterile or sterilizable, e.g. by gamma-irradiation, autoclaving, or chemical sterilant such as ethylene oxide or vaporized hydrogen peroxide.

Optionally, the robotic arm assembly may comprise at least one pneumatic/hydraulic actuator comprising at least one of linear actuators, rolling diaphragm actuators, sterilizable linear actuators, sterilizable syringes, compressible cylinder, hydraulic rotary actuator, and hydraulic rotary vane actuators that are extendible in at least one direction by providing a fluid pressure to the inside of the actuating unit. The actuators apply force to an articulating support which extends or retracts the movement of a robotic arm. A plurality of actuators may be assembled with a plurality of articulating supports to provide the desired movements within the sterile chamber.

Optionally, the robotic arm assembly may move along a plurality of tracks using a wheeled and/or track assembly to increase the range of movement within the sterile chamber. The wheeled and/or track assembly may be powered by a hydraulic motor, a pneumatic motor, an electric motor, and/or a magnetic motor.

Optionally, the robotic arm assembly may comprise a soft robotic assembly. The soft robotic assembly may be actuated when pressurized with hydraulic and/or pneumatic pressure. A soft robotic assembly of sufficient complexity may allow the robotic arm to articulate around a fixed location instead of requiring a rotatable platform to direct the robotic arm in a particular direction.

Optionally, the robotic arm assembly may comprise a plurality of inflatable assemblies, where the supports of the robotic arm assembly comprise inflatable sections. The inflatable sections may comprise bags, bladders, and/or expandable reservoirs. The inflatable assemblies may be articulated along a seam and/or seal between two or more inflatable sections. The articulation of the robotic arm may be controlled by the movement of a plurality of cables connected to the inflatable sections.

Optionally, the fluid connections for control of the robotic arm assembly may be internal or external to the sterile chamber containing the robotic arm assembly. For an externally connected assembly the fluid lines for hydraulic/pneumatic control of the robotic arm assembly may be aseptically connected to the sterile chamber. The control mechanism for the robotic arm assembly may be manually controlled by an operator and/or automatically controlled utilizing a computer controlled setup. The computer-controlled setup may follow positional commands from a pre-programmed sequence stored in a memory storage unit.

Optionally, the robotic arm assembly may utilize a positional system for determining the distances and orientations of objects to determine how best to grab the objects and move them within the three-dimensional space of the sterile chamber. The positional system may comprise a plurality of cameras located on the sterile chamber and visual targets placed onto the components, items, and/or physical barriers. The visual targets may comprise variable augmented reality markers. Alternatively, a plurality of cameras may be placed onto the robotic arm assembly itself to position the robotic arm assembly. Alternatively, for additional precision a laser tracking system may be utilized externally by mounting it on the sterile chamber or internally by mounting it onto the robotic arm assembly. The robotic arm assembly may utilize other positioning techniques such as depth scanning, LIDAR, ultrasound, acoustic tracking, RFID/NFC tags, and other electronic methods to determine the position of the robotic arm operating within the three-dimensional space of the sterile chamber.

One aspect of the invention relates to a manufacturing device that comprises a vacuum-forming unit. The vacuum-forming unit assembly is internal to a sterilizable chamber and may comprise at least one rigid support structure, at least one vacuum platform with a plurality of holes, at least one vacuum pressure source, at least one heating element, at least one dispensing mechanism for dispensing moldable plastic sheets, at least one mold, and at least one vent filter assembly. The vacuum-forming unit assembly is intended for use in the manufacture of items with reproducible shapes by the forming of heated plastic sheet over a mold on a vacuum platform under vacuum pressure. Exemplarily, this manufacturing method may be used to produce a plurality of items with the same shape.

Optionally, the vacuum-forming unit assembly may utilize a vacuum pressure source which is external to the sterilizable chamber and is aseptically connected to such a vacuum source and/or is connected to a sterilizing grade air filter which is sized to sufficient capacity for the maximum vacuum pressure required for the forming process.

Optionally, the vacuum-forming unit assembly may utilize a vent filtration device which is sized to sufficient capacity to prevent the collapse of the sterile chamber under maximum vacuum pressure conditions.

Optionally, the vacuum-forming unit assembly may utilize a heating element for the heating of a deformable plastic sheet. The heating element heats a plastic sheet to make it easily deformable to take on the shape and structure of a fixed mold when it comes in contact with the mold under vacuum pressure. The heating element may be an electric heater, a single-use chemical heater device such as a device exploiting the exothermic oxidation of iron when exposed to air, a re-usable chemical heater device such as a device exploiting the exothermic crystallization of supersaturated solutions, or through the circulation of an externally-heated fluid source such as heated sterile filtered water, glycol, and/or steam. An externally-connected heating source may utilize an aseptic connection to connect to the heating element assembly within the sterile chamber.

Optionally, the sterilizable chamber may utilize a thermal barrier insulation to prevent structural damage to the sterile chamber and other internal components through the use of a heating element used with a manufacturing process device located within the sterile chamber.

Optionally, the vacuum-forming unit assembly may utilize a plurality of blades and/or die-cutting tools to cut the molded plastic sheet around the mold and to separate the desired formed product from the remaining plastic sheet.

One aspect of the invention relates to a manufacturing device that comprises an injection-molding unit. The injection-molding unit assembly is internal to a sterilizable chamber and may comprise at least one rigid support structure, at least one reservoir with meltable material, at least one heating element, at least one compression source, at least one dispensing unit, at least one solid mold comprising of at least two parts, and at least one vent filter assembly. The injection-molding unit assembly is intended for use in the manufacture of items with reproducible shapes by the melting of heated plastic material injected into a solid mold. Exemplarily, this manufacturing method may be used to produce a plurality of items with the same shape.

Optionally, the injection-molding unit assembly may utilize a heating element for the heating of moldable material, such as plastic pellets. The heating element heats the plastic pellets until they are melted within a chamber and the melted plastic is extruded into a solid mold made from at least two parts. The heating element may be an electric heater, a single-use chemical heater device such as a device exploiting the exothermic oxidation of iron when exposed to air, a re-usable chemical heater device such as a device exploiting the exothermic crystallization of supersaturated solutions, or through the circulation of an externally-heated fluid source such as heated sterile filtered water, glycol, and/or steam. An externally-connected heating source may utilize an aseptic connection to connect to the heating element assembly within the sterile chamber.

Optionally, the injection-molding unit assembly may utilize an external connection to supply the moldable material reservoir. The external connection for the moldable material supply into the sterile chamber may utilize an aseptic connection.

One aspect of the invention relates to a manufacturing device that comprises a laser-cutting unit. The laser-cutting unit assembly is internal to a sterilizable chamber and may comprise at least one rigid support structure, at least one two-axis positioning assembly, at least one laser assembly, at least one power source, and at least one substrate. The laser-cutting unit assembly is intended for use in the manufacture of custom-shaped items by cutting through a material substrate with a precision directed laser.

In case the laser-cutting device is not pre-assembled with the sterilized chamber, a laser-cutting device that is pre-sterilized, potentially by an alternate sterilization method than the sterilized chamber, may be aseptically connected to the laser-cutting assembly within the sterilized chamber. A non-sterile laser-cutting device may be inserted into a connection chamber and sterilized utilizing a chemical sterilant method such as ethylene oxide or vaporized hydrogen peroxide prior to removing the barrier between the printing head assembly and the printer assembly prior to usage within the sterilized chamber.

Optionally, the laser-cutting unit assembly may utilize an internal laser assembly which is powered by an external electrical connection, an internal battery storage mechanism, an inductively charged electrical connection, a chemical reaction, a microwave or visual line-of-sight power source, or other wireless power source. A visual line-of-sight power source is similar to a laser but does not require safety glasses to protect human eyes during operation since it is emitted within the visual part of the spectrum. Such a system to power local electronic devices is outlined in US patent application: US 2007/0019693 A1.

Optionally, the laser-cutting unit assembly may utilize a two-axis controller positional system, which may be driven by hydraulic, pneumatic, electric, or magnetically controlled motors. The positional system may utilize a system comparable to the system utilized for the three-dimensional printing control system.

Optionally, the laser-cutting unit assembly may be utilized for the laser labeling and/or barcoding of some materials or manufactured components.

Optionally, the sterile chamber may utilize a plurality of vent filters to remove heated air within the sterile chamber and to replace it a temperature regulated air. The airflow speed and number of air changes in the sterile chamber may serve as a temperature regulation mechanism. An external heat exchanger may be utilized to recirculate the air and control the temperature of the air entering into the sterile chamber.

Optionally, the sterile chamber may utilize a plurality of vent filters to remove aerosolized particulates or smoke from the sterile chamber. This may be utilized to remove aerosolized bioactive materials during the laser-cutting process, aerosols from spray coating, aerosolized particulates from CNC removal of materials, smoke or particulates from laser cutting, or general aerosolized particulates from manufacturing processes or material movements.

Optionally, the sterile chamber may utilize an absorptive material in the sterile chamber walls to block and/or reduce the intensity of the laser at the specific wavelengths that the laser assembly operates at. This will reduce the risk of exposure to operators who may or may not be wearing sufficient eye protection.

One aspect of the invention relates to a manufacturing device that comprises an ultrasonic-welding unit. The ultrasonic-welding unit assembly is internal to a sterilizable chamber and may comprise at least one rigid support structure, at least one ultrasonic welder comprising of a piston, a transducer, a converter, a booster, a sonotrode, a horn, an anvil, and at least two materials to weld together.

Optionally, the ultrasonic-welding unit assembly may be powered by an external electrical connection, an internal battery storage mechanism, an inductively charged electrical connection, a chemical reaction, a microwave or visual line-of-sight power source, or other wireless power source.

One aspect of the invention relates to a sampling system that comprises a single-use sampling system. The sampling system may be part of a manufacturing device and the sampling procedure may be part of a manufacturing operation. The single-use sampling system may comprise a collection container for holding a fluid sample, a fluid connection to the collection container, a single-use aseptic connection to a sterile chamber, a sampling method for drawing fluid material from the sterile chamber, and an aseptic disconnection method for removal of the container containing the fluid sample. The aseptically disconnected container may undergo measurement by an external measurement device, be used for storage of the material, or be used as a reference for the generation of other materials.

One aspect of the invention relates to a sampling system that comprises an external continuous sampling system. The external continuous sampling system may comprise an aseptic connection to a sterile chamber, a sampling method for drawing fluid material from the sterile chamber, an external measurement device, and a fluid connection to the external measurement device. The external measurement device may be a multi-use device which may additionally use single-use sensors for the testing of material from the sterile chamber. The fluid material after sampling or measurement may be aseptically returned to the sterile chamber via an aseptic connection or may be discarded through storage in a container or through a drain.

One aspect of the invention relates to a sampling system that comprises an internal sampling system. The internal sampling system may comprise a fluid connection to a collection container, a sampling method for drawing fluid material from the sterile chamber, and an internal measurement device. The internal measurement device may be integrated into the collection container and/or may be integrated into the sterile chamber.

One aspect of the invention relates to an optical measurement device. The optical measurement device, such as a microscopic camera, may contain a plurality of lenses, a zoom lens, an autofocus, and internal and/or external LED lighting.

Optionally, the optical measurement device may be inserted into a fixed position port within the sterile chamber using the same methods as used with the printing head insertion. The optical measurement device may be single-use or multi-use. A non-sterile optical measurement device may be connected to the sterile chamber and sterilized in place utilizing chemical sterilization methods. Alternatively, a pre-sterilized optical measurement device may be connected and inserted into the sterile chamber through an aseptic connection method.

Optionally, the optical measurement device may utilize the array of cameras utilized for the positioning system. The array of cameras may be positioned externally to the sterile chamber and view the internal assembly through a plurality of transparent windows and/or transparent material.

Optionally, the optical measurement device may optically examine, measure, record, and store the optical data in a digital storage device for comparison, trending, or time-lapse. The optical measurements may also be utilized to determine the profile, density, coverage, adherence, invasiveness, health, and viability of cell growth onto a structural support. The optical measurements may additionally examine other factors like color change from a chromic die for measuring pH, temperature, or other factors. The optical measurements may additionally be able to examine the contents for potential contamination of bacteria, fungi, viruses, or other unwanted cell growth.

One aspect of the invention relates to a chemical temperature-regulation device. The chemical temperature-regulation device of the sterile chamber may house a chemical reaction that comprises exothermic and/or endothermic reactions. The chemical temperature-regulation device may be internal to the sterile chamber and may be single-use. A single-use chemical temperature-regulation device may be endothermic such as by using ammonium nitrate or exothermic such as by exothermic oxidation of iron in air. It is possible for the chemical reaction to be recharged such as by exothermic crystallization of supersaturated solutions with sodium acetate. The chemical temperature regulation device may be sterilized along with the single-use chamber and discarded when the use of the chamber is completed.

One aspect of the invention relates to the aseptic connection of at least two sterile chambers together to form a network of sterile chambers where each sterile chamber performs a specific task. The network of sterile chambers increases the functionality of the items manufactured within the sterile chambers and the bioactive products which are derived from that manufacturing. The network of sterile chambers additionally allows the bioactive products to be printed within custom manufactured containers, supplied with nutrient rich media, undergo precise metered dosing of at least one drug product, undergo incubation within a temperature regulated environment, undergo analysis by an optical measuring device, undergo sampling by an aseptic sampling device and be aseptically removed from the network of chambers as a final manufactured bioactive product. The types of usages for such a network of sterile chambers include but are not limited to in vitro testing, the manufacture of biologically active cell products, the manufacture of implantable biological products, the manufacture of biologically active products on biosensors, the manufacture of biologically active products on diagnostic membranes, and custom manufactured filters coated with bioactive materials such as antibodies for use in capture or capture and elute processing methods. In vitro testing inside a network of sterile chambers includes the manufacturing of custom multi-well plates and coatings for in vitro testing, the use of multi-well plates for the screening of three-dimensional cell products, in vitro efficacy and toxicity studies of the effects of metered drug products on three-dimensional printed cells within multi-well plates. The manufacture of biologically active cell products inside a network of sterile chambers includes the printing of scaffolding materials for coating with bioactive products, the manufacture of complex multi-material assemblies for coating with bioactive products, the manufacture of complex multi-material medical devices with bioactive coatings, the printing of cells and cell products onto complex multi-material assemblies, the printing of cell products, cellular structures, scaffoldings, organs, and organ simulants grown from an individual patient's cells in a single-use bioreactor, processed, dispensed, incubated and grown in a single-use sterile environment. The manufacture of biologically active products on biosensors inside a network of sterile chambers includes the printing of biologically active products onto electronic devices and/or substrates to add to electronic devices for the detection of an analyte. The analyte may be detected through the combination of a biological component with a physicochemical detector. The manufacture of biologically active products on diagnostic membranes inside a network of sterile chambers includes the printing of biologically active products onto a diagnostic membrane and the assembly of the protective covering and/or device delivery tool for the diagnostic testing, reading of results, and test analysis. The manufacture of custom filters with biologically active products inside a network of sterile chambers includes the printing of biologically active products onto filter membranes which are assembled into a completed filtration unit. Bioactive materials such as antibodies may be utilized with a custom filter membrane for the capture and removal or for the capture and elution of a specific material from a filtered fluid.

Additional objects, advantages and features of the present invention will now be described in greater detail, by way of example, with reference to preferred embodiments depicted in the drawings.

BRIEF DESCRIPTION OF THE DRAWINGS

FIGS. 3A-3F illustrate an embodiment of the movements of the x-axis and z-axis controls of the three-dimensional printing platform utilizing inflatable bags/bladders.

FIGS. 5A and 5B illustrate an embodiment of alternate mechanisms to drive the three-dimensional printing tray into a precise location for deposition of printing material.

FIGS. 13A-13F illustrate an embodiment of the connections steps to insert the printing head into the sterile three-dimensional assembly body.

FIGS. 14A-14E illustrate an embodiment of the setup process for a flexible wall three-dimensional printer from the packed shipping configuration.

FIGS. 15A-15D illustrate an embodiment of the movements of the x-axis, y-axis, and z-axis controls of the three-dimensional printing platform utilizing hydraulically-driven actuators.

FIGS. 16A-16G illustrate several embodiments of printing with multiple degrees of freedom.

FIGS. 17A-17G illustrate several embodiments of moving print platforms for printing with multiple degrees of freedom.

FIGS. 18A-18M illustrate several embodiments of printer designs.

FIGS. 19A-19F illustrate alternate embodiment of the connections steps to insert the printing head into the sterile three-dimensional assembly body.

FIGS. 20A-20E illustrate another embodiment of the connections steps to insert the printing head into the sterile three-dimensional assembly body.

FIGS. 21A-21E illustrate an alternate embodiment of the connections steps to insert a sterilized printing head with a bellows assembly into the sterile three-dimensional assembly body.

FIGS. 27A-27E illustrate multiple embodiments of a sampling system that may provide periodic and/or continuous sampling of the materials located in the printing tray.

FIGS. 30A-30E illustrate an embodiment of an injection-molding unit internal to a sterile chamber for the manufacturing of components for use with biologically active materials.

DETAILED DESCRIPTION OF THE PREFERRED EMBODIMENTS

Figure 1:
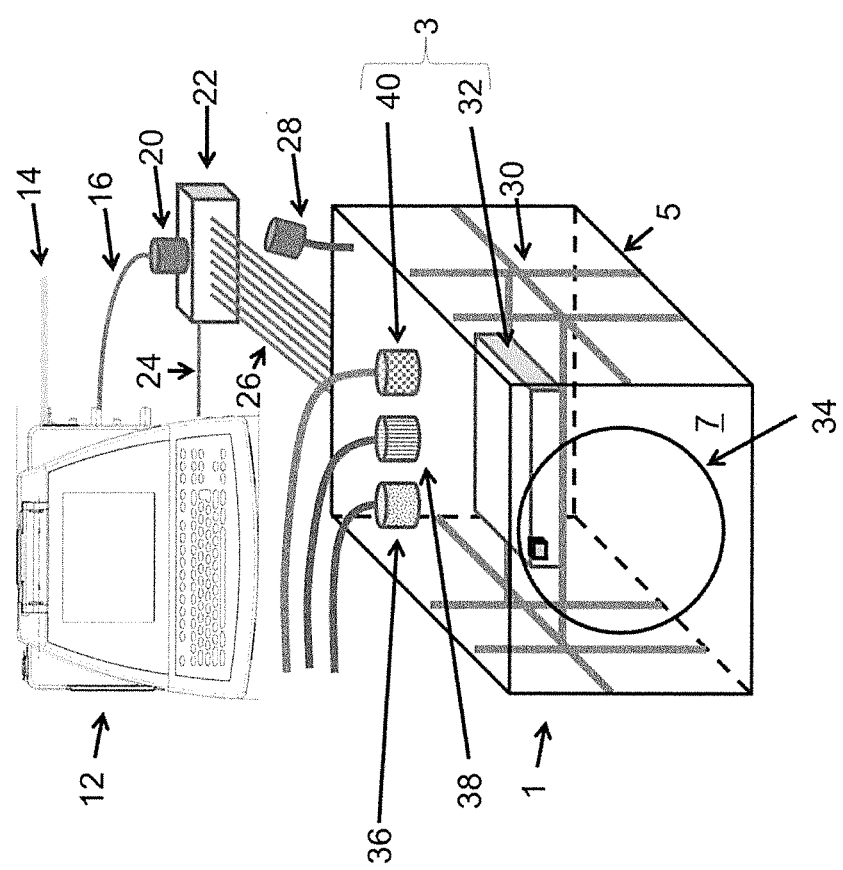
FIG. 1 illustrates an embodiment of a sterile, single-use three-dimensional printer utilizing a highly regulated pressure source and an electronically controlled tubing manifold to control the movement of a 3 axis tray.

FIG. 1 shows a three-dimensional printing device 1 comprising a printer housing 5 enclosing a printer assembly 3. The inside of the printer housing 5, particularly the printer assembly 3, is sterilizable and disposable, i.e. intended for single use. The printer housing 5 can be formed of rigid walls or flexible walls 7 held open by a rigid internal and/or external skeleton.

The three-dimensional printing device 1, particularly the printer assembly 3 and/or the inside of the printer housing 5, can be sterilized by gamma-irradiation, autoclaving, or chemical sterilant (such as ethylene oxide or vaporized hydrogen peroxide). The electronic and controlling components for controlling the printer assembly 3 that are reused or that are sensitive to the sterilization method can be arranged outside the printer housing 5 and might be removably attached to the sterilized three-dimensional printer 1 during setup.

The at least one printing head of the three-dimensional printing device can positioned along three grades of freedom, such as the three axes x, y, and z, by means of a pressurized fluid, which can be provided by a fluid source. As an example, compressed air might be used as pressurized fluid. A regulated fluid source, which drives a three axis controller for the three-dimensional printer can be controlled by an automated integrity testing device 12 which takes air pressure from an incoming source and uses a sensitive, calibrated pressure transducer to accurately measure and dispense a precise pressure of fluid, such as air, to an outlet connection 16.

The outlet connection 16 can be connected to a sterilizing grade filter 20 which feeds an electronically controlled tubing manifold 22. The tubing manifold physically open and closes the connections to all of the air pressure tubing lines 26 which feed the three-dimensional printer 1 and is controlled by an electronic connection 24 to the controlling device 12. The tubing manifold 22 and vent filter 20 unit can be sterilizable along with the three-dimensional printer 1 as a single piece and have an external electronically controlled device (not shown) that can be attachable to the tubing manifold 22 to control the opening and closing of each of the air pressure tubing lines 26. The tubing lines 26 can deliver fluid pressure and be individually attached to fluid actuator, such as air actuators or inflatable bags or bladders, which can be utilized to move a printing tray 32 on a three axis framework 30. The tubing manifold 22 can also individually vent each of the tubing lines 26 to remove air pressure in the inflatable bag/bladder or the air actuators. The three-dimensional printer is vented by a sterilizing grade air filter 28 so the internal pressure is always maintained at ambient. The printing tray 32 is push or pulled along the three axis framework 30 which can consist of threaded screws or tracks by the fluid actuators.

The printing tray 32 can be a flat platform or have walls which can hold a fluid during the printing process. The three-dimensional printer 1 can feature a plurality of fixed or movable printing heads with different functionality. In this embodiment the printing heads are fixed and features a spray deposition printing head 36 for coating the three-dimensional printed object with proteins, chemicals or molecules, a solid extruder printing head 38 for deposition of cells and other materials from a bioreactor, and a heated solid extruder head 40 for the deposition of structural elements. After the printing onto the tray has been completed the tray and printed structure can be removed via a transfer hatch 34 on the three-dimensional printer 1 wall. A sterile transfer bag (not shown) can be connected to the transfer hatch 34 where the tray and three-dimensional printed object can be removed and maintained within a sterile environment. The entire three-dimensional printer assembly 1 can also be placed in an incubator if further printing steps are required with the same unit.

FIGS. 2A-2D show an embodiment of inflatable bags or bladders utilized in a three-dimensional printer for the purpose of moving a platform on a three-axis framework.

Figure 2B:
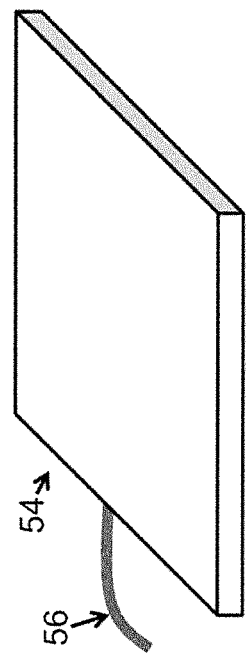
FIGS. 2A-2D illustrate an embodiment of inflatable bags/bladders utilized in a three-dimensional printer for the purposes of moving a platform on a 3 axis framework.
Figure 2D:
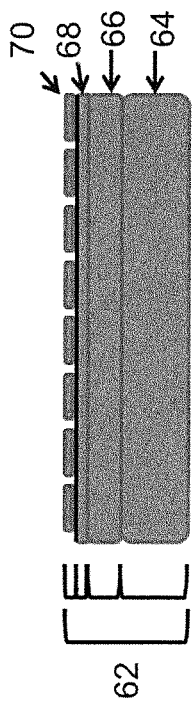
Figure 2A:
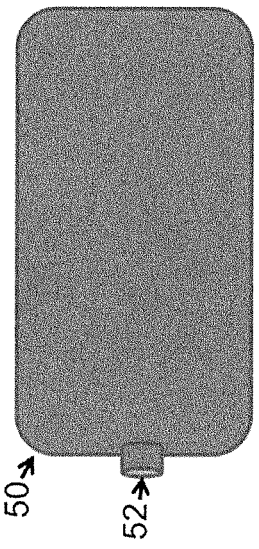

FIG. 2A is a top view of a two dimensional bladder 50 which can be inflated and vented out of a port 52.

FIG. 2B is a side view of a three-dimensional bag 54 which can be inflated and vented out of a port 56.

Figure 2C:
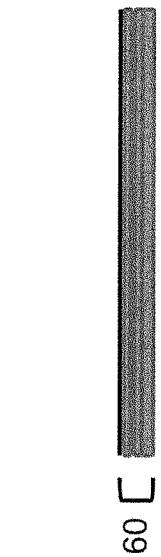

FIG. 2C is a side view of an assembly of three-dimensional bags 60 which are in a deflated state.

FIG. 2D is a side view of an assembly of three-dimensional bags 62 which are in an inflated state.

The individual three-dimensional bags in the assembly go from larger sizes to smaller sizes and provide coarse to fine resolution for movement of a three-dimensional printing platform. The bags 64 and 66 provide the coarse resolution for inflation while bags 68 and 70 provide fine resolution for inflation. These are in place to move the three-dimensional printing platform into the correct position for the accurate deposition of printing materials within the specified coordinates.

FIGS. 3A-3F show an embodiment of the movements of the x-axis and z-axis controls of the three-dimensional printing platform utilizing inflatable bags or bladders.

FIG. 3A is a top view of an embodiment of a three-dimensional printing device having a printable space 100 where a three-dimensional printing platform 102 in the following also called printing tray 102, as a preferred printing platform, is pushed into a precise position by the coarse and fine resolution of the inflatable bags or bladders. In this case the three-dimensional printing tray 102 is in a centralized position and the bags 104 and 106 are in a deflated position.

FIG. 3B is a top view of the printable space 100 where a three-dimensional printing tray 102', as a preferred printing platform, is pushed to a precise position to the left by the inflation of bag assembly 106'. Bag assembly 104 remains in a deflated position.

FIG. 3C is a top view of an embodiment of the printable space 100 where a three-dimensional printing tray 102", as a preferred printing platform, is pushed to a precise position to the right by the inflation of bag assembly 104' and the deflation of bag assembly 106.

FIG. 3D is a top view of an embodiment of the printable space 100 where a three-dimensional printing tray 102''', as a preferred printing platform, is pushed to a precise position forward by the inflation of bag assembly 108'. Bag assemblies 104, 106, and 110 remain in a deflated position.

FIG. 3E is a top view of an embodiment of the printable space 100 where a three-dimensional printing tray 102'''', as a preferred printing platform, is pushed to a precise position backward by the inflation of bag assembly 110' and the deflation of bag assembly 108. Bag assemblies 104 and 106 remain in a deflated position.

FIG. 3F is a top view of an embodiment of the printable space 100 where a three-dimensional printing tray 102''''', as a preferred printing platform, is pushed to a precise position in the forward right direction by the inflation of bag assembly 108' in the forward direction and bag assembly 104' in the right direction. Bag assemblies 106 and 110 are in a deflated position.

Figure 4B:
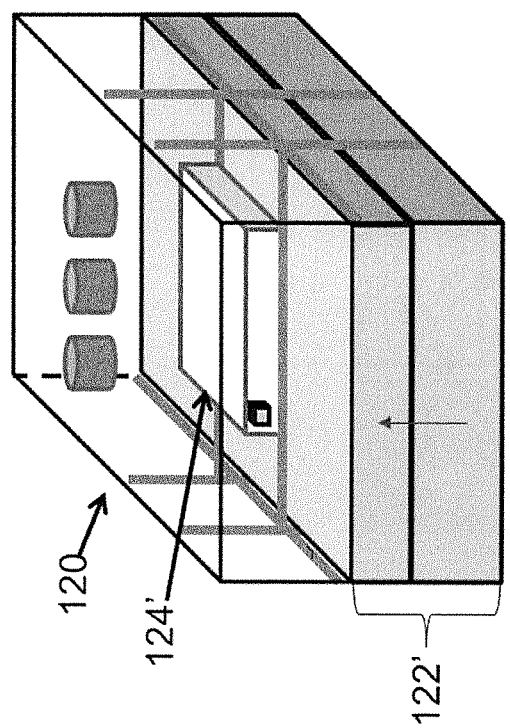
FIGS. 4A and 4B illustrate an embodiment of the movements of the y-axis of the three-dimensional printing platform utilizing inflatable bags/bladders.
Figure 4A:
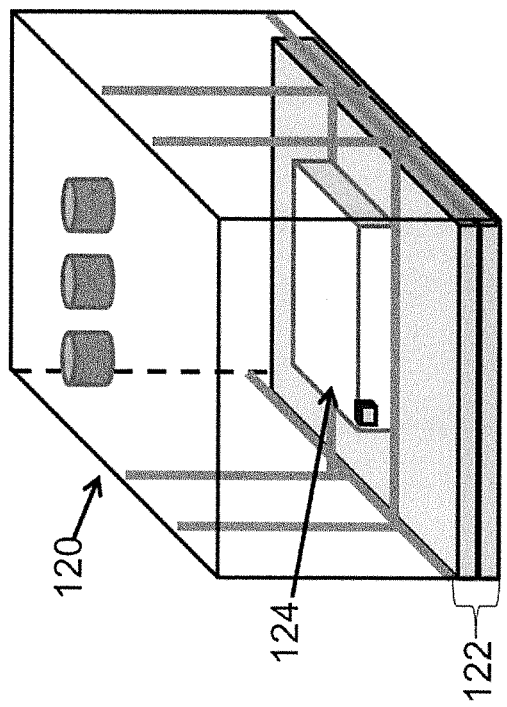

FIGS. 4A and 4B show an embodiment of the movements of the y-axis of the three-dimensional printing platform or printing tray 124 utilizing inflatable bags or bladders.

FIG. 4A is a side view of an embodiment of a three-dimensional printer 120 where a three-dimensional printing tray 124 is pushed into a precise position by the coarse and fine resolution of the inflatable bags or bladders. In this case the three-dimensional printing tray 124 is in a centralized position and the bag assembly 122 is in a deflated position.

FIG. 4B is a side view of an embodiment of a three-dimensional printer 120 where a three-dimensional printing platform or printing tray 124' is pushed upwards into a precise position by the inflation of bag assembly 122'. The elevation of the tray by the inflation of bag assembly 122' also lifts the bag assemblies (not shown) utilized for the x-axis and z-axis controls on the three-axis framework.

FIGS. 5A and 5B show an embodiment of alternate mechanisms to drive the three-dimensional printing tray or printing platform into a precise location for deposition of printing material.

FIG. 5A is a side view of an embodiment of an pneumatic actuator 140 which utilizes compressed air 150 through an airline 144 which converts the air pressure to a mechanical motion, utilizing a valve stem or a rotary actuator 146, and driving an internal screw mechanism 148 which is attached to the three-axis framework, which in this embodiment comprises a threaded screw 142. This mechanism allows the pneumatic actuator 140 to move in a forward or backwards direction 154 along the path of the threaded screw 142, or alternatively a track. The waste compressed air is expelled out of outlet 152 and into the three-dimensional printer chamber where it is vented by an appropriately sized sterilizing grade vent filter (not shown) which maintains the chamber at ambient pressure.

FIG. 5B is a side view of a magnetic motor control device which can drive an internal screw to move the three-dimensional printing tray. The magnetic motor control device comprises an external motor 156, a shaft 158 and a linkage device 160 containing a plurality of magnets 162. The linkage device 160 connects to a location on a three-dimensional printer body wall 164 which can be rigid or flexible. An internal linkage device 168 contains a plurality of magnets 166 which mates with the plurality of magnets 162 of the external linkage device 160. The external motor 156 rotates the external linkage device 160 and magnets 162, and thus, drives the internal magnets 166 and the linkage device 168 which results in a turning motion 172 of an internal threaded screw 170. A friction reducing assembly, such as ball bearings (not shown), can be utilized on the internal and the external linkage devices 160 and 168 to reduce the friction from the drive magnets on the three-dimensional printer wall 164. This turning motion 172 of the internal threaded screw 170 allows the three-dimensional printing tray or printing platform to move precisely in a forward or reverse direction along rotational axis of the internal threaded screw 170.

FIGS. 6A-6D show an embodiment of a precision tracking system or position tracking system to verify the coordinate location of the printing platform also called printing tray along the three axis framework. The precision tracking system can additionally be utilized to calibrate the distance between the printing platform or the printing tray and the printing head in use. The precision tracking system can determine the distance and location of multiple points on the printing platform or the printing tray and make the adjustments to level the printing platform in line with the printing head. This function can be performed prior to printing and/or during the printing function.

Figure 6B:
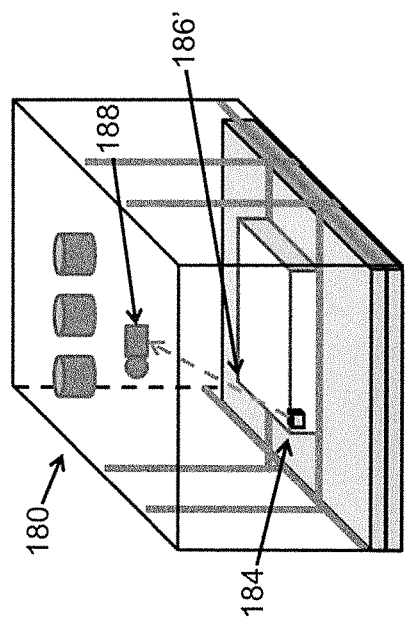
FIGS. 6A-6D illustrate an embodiment of a precision tracking system to verify the coordinate location of the tray along the 3 axis framework.
Figure 6D:
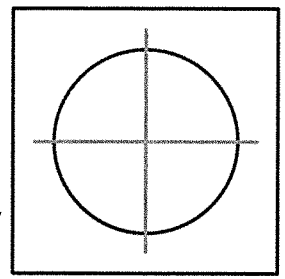
Figure 6A:
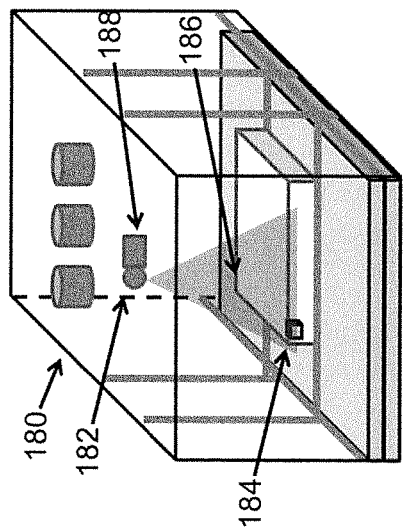

FIG. 6A is a front view of a three-dimensional printer 180 where a laser emitting device 182 sends out a signal 186 which is reflected by means of a plurality of mirrors 184 located on the printing platform or tray.

FIG. 6B is a front view of the same three-dimensional printer 180, as in FIG. 6A where a laser detection device 188 detects the angle and time the signal 186' takes to reach the detector giving precise coordinates of the three-dimensional printing tray location. This information is relayed to the controller where the printer can precisely deposit material onto the printing tray along the three axis framework.

Figure 6C:
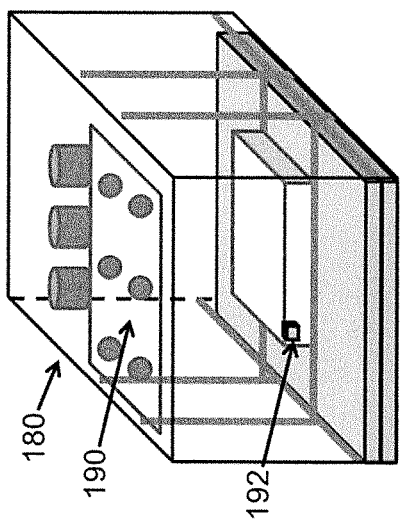

FIG. 6C is a front view of a three-dimensional printer 180 comprising a camera array 190, wherein the camera array 190 observes a visual target 192 attached to the three-dimensional printing platform or formed with the three-dimensional printing platform, also called a printing tray. The location and size of the visual target 192 can provide precise coordinates of the three-dimensional printing tray location which is relayed to the controller where the printer can precisely deposit material onto the printing tray along the three axis framework.

FIG. 6D is an embodiment of the visual target 194 which is recognized by the camera array 190.

Figure 7:
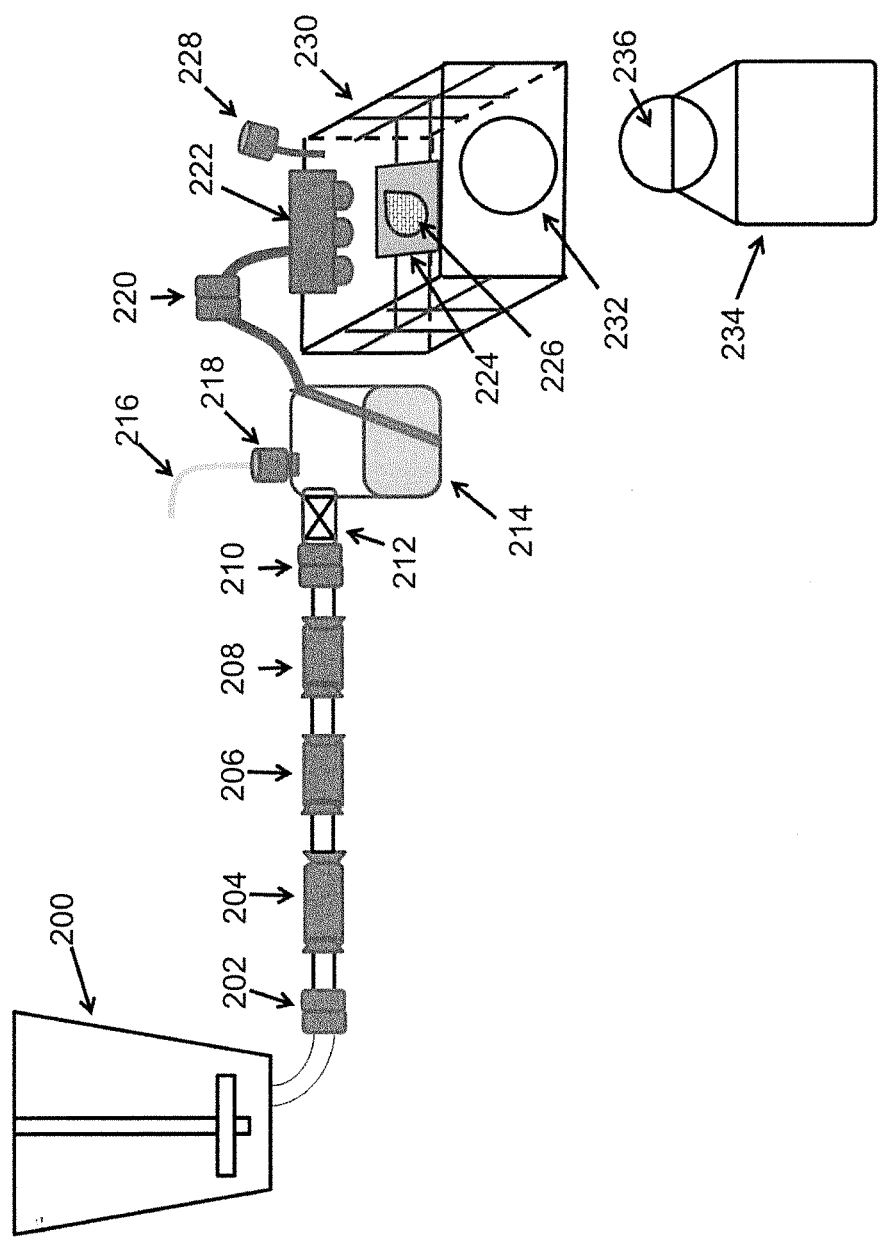
FIG. 7 illustrates an embodiment of a single-use bioreactor and filtration assembly connected to a single-use three-dimensional printer via an aseptic connector to form a printed object.

FIG. 7 shows an embodiment of a single-use bioreactor and filtration assembly connected to a single use three-dimensional printer via an aseptic connector, wherein the three-dimensional printer is capable to form a printed object. This embodiment shows a gamma irradiated assembly containing a single-use bioreactor 200 which is connected to a filtration train via an aseptic connector 202. The filtration train can comprise a plurality of filters including but not limited to a depth filter 204, a pre-filter 206, and a sterilizing grade filter 208.

The filter train is connected to a surge vessel container 214 via an aseptic connector 210. The surge vessel container 214 fills with the material filtered from the bioreactor, which can be driven by a constant pressure or constant flow source. A sterilizing grade vent filter 218 allows the surge vessel container 214 to vent during filling. After the filtration process is complete or the surge vessel container 214 is full the valve 212 to the filter train is closed and a regulated compressed air line 216 is attached to the sterilizing grade air filter 218. The pressure drives the liquid up a dip tube and into a tubing piece which is connected via an aseptic connector 220 to the three-dimensional printing assembly 230. The material from the surge vessel container 214 can be concentrated utilizing a cell retention and concentration device, preferably a gamma irradiatable Hydrocyclone (not shown). The processed material can be deposited onto the three-dimensional printing tray or printing platform 224 in a precise location through extrusion, spray deposition, or by mixing with a structural component through one or more of the at least one printing head of the printer assembly 222. The three-dimensional printed object 226 on the three-dimensional printing tray 224 is formed by layer-by-layer additive printing of material from the printer assembly 222. The three-dimensional printer 230 vessel, which can be rigid or flexible, is vented by a sterilizing grade vent filter 228. After the printing of the three-dimensional printed object 226 has been completed the three-dimensional printing tray 224 and printed structure 226 can be removed via a transfer hatch 232 on the three-dimensional printer 230 wall. A sterile transfer bag 234 can be connected to the transfer hatch 232 via a sterile connection 236. Thus, the printing tray 224 and three-dimensional printed object 226 can be removed from the three-dimensional printer 230 while being maintained within a sterile environment.

Figure 8:
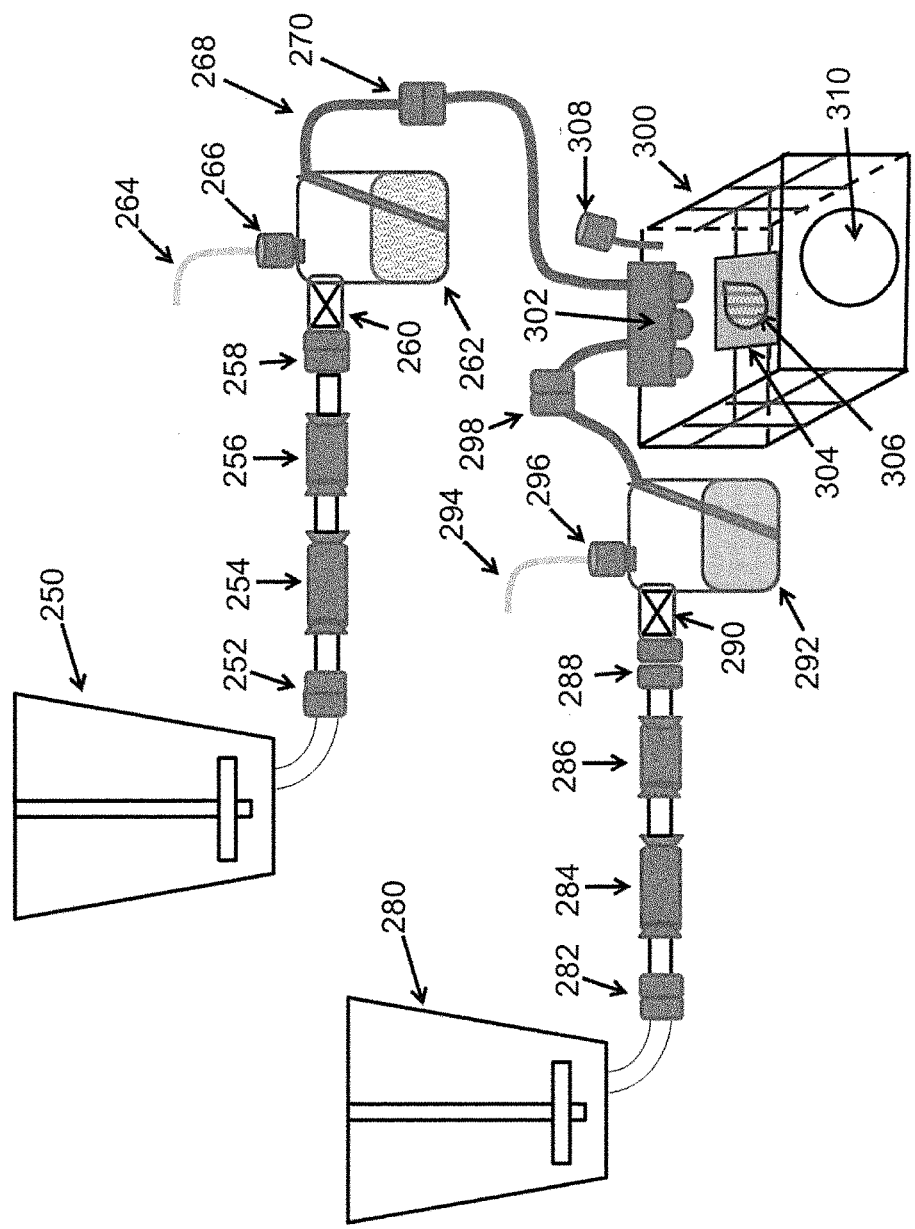
FIG. 8 illustrates an embodiment of two single-use bioreactors and filtration assemblies connected to a single-use three-dimensional printer via aseptic connectors to form a printed object.

FIG. 8 shows an embodiment of two single-use bioreactors and filtration assemblies connected to a single-use three-dimensional printer via aseptic connectors to form a printed object. This embodiment shows a gamma irradiated assembly containing two single-use bioreactors 250 and 280 which are connected to filtration trains via aseptic connectors 252 and 282. The filtration trains can comprise a plurality of filters including but not limited to pre-filters 254 and 284 and sterilizing grade filters 256 and 286. The filter trains can be connected to a surge vessel container 262 and 292 via aseptic connectors 258 and 288. The surge vessel containers 262 and 292 fill with the material filtered from their respective bioreactors, which can be driven by a constant pressure or constant flow source. Sterilizing grade vent filters 266 and 296 allow for the surge vessel containers 262 and 292 to be vented during filling. After the filtration process is complete or the surge vessel containers 262 and 292 are full, the valves 260 and 290 to the filter trains are closed and regulated compressed air lines 264 and 294 are attached to the sterilizing grade air filters 266 and 296. The pressurized air provided by the air lines 264 and 294 drives the liquid up a dip tube and into a tubing piece which is connected via aseptic connectors 270 and 298 to a single three-dimensional printing assembly 300.

The material from the surge vessel containers 262 and 292 can be deposited onto the three-dimensional printing tray or printing platform 304 in a precise location through extrusion, spray deposition, or by mixing with a structural component through one or more of the printing heads on the printer assembly 302. The three-dimensional printed object 306 on the three-dimensional printing tray 304 is formed by layer-by-layer additive printing from material coming from either bioreactor or from both in a specified mixture from the printer assembly 302.

The three-dimensional printer 300 vessel, which can be rigid or flexible, is vented by a sterilizing grade vent filter 308. After the printing of the three-dimensional printed object 306 has been completed the three-dimensional printing tray 304 and printed structure 306 can be removed via a transfer hatch 310 on the three-dimensional printer 300 wall.

Figure 9:
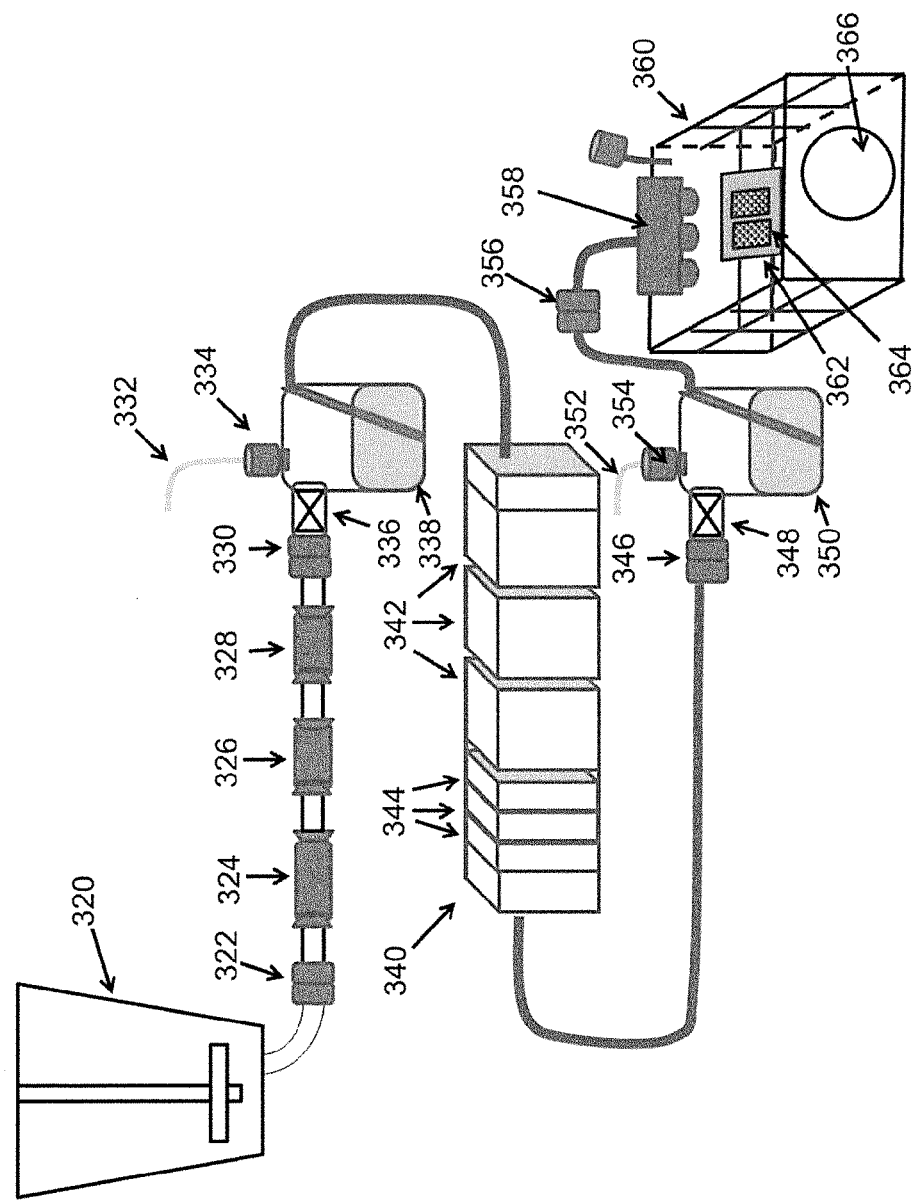
FIG. 9 illustrates an embodiment of a single-use bioreactor, a filtration assembly, and a crossflow assembly connected to a single-use three-dimensional printer via an aseptic connector to form a printed object.

FIG. 9 shows an embodiment of a single-use bioreactor, a filtration assembly, and a cross flow assembly connected to a single-use three-dimensional printer via an aseptic connector to form a printed object. This embodiment comprises a gamma irradiated assembly containing a single-use bioreactor 320 which is connected to a filtration train via an aseptic connector 322. The filtration train can comprise a plurality of filters including but not limited to a depth filter 324, a pre-filter 326, and a sterilizing grade filter 328. The filter train is connected to a surge vessel container 338 via an aseptic connector 330. The surge vessel container 338 fills with the material filtered from the bioreactor which can be driven by a constant pressure or constant flow source. A sterilizing grade vent filter 334 allows the surge vessel container 338 to vent during filling. After the filtration process is complete or the surge vessel container 338 is full, the valve 336 to the filter train is closed and a regulated compressed air line 332 is connected fluidly with the sterilizing grade air filter 334. The pressure drives the liquid up a dip tube and into a tubing piece which is connected to a pre-sterilized cross flow assembly 340.

The cross flow assembly 340 can comprise a plurality of microfiltration 342 and/or ultrafiltration cassettes 344 in varying sizes. The cross flow assembly is connected to a surge vessel container 350 via an aseptic connector 346. The surge vessel container 350 fills with the material filtered and/or concentrated from the cross flow assembly which can be driven by a constant pressure or constant flow source. A sterilizing grade vent filter 354 allows the surge vessel container 350 to vent during filling. After the cross flow processing is complete or the surge vessel container 350 is full, the valve 348 to the cross flow assembly is closed and a regulated compressed air line 352 is attached to the sterilizing grade air filter 354. The pressure drives the liquid up a dip tube and into a tubing piece which is connected via an aseptic connector 356 to the three-dimensional printing assembly 360.

The material from the surge vessel container 350 can be deposited onto the three-dimensional printing tray or printing platform 362 in a precise location through extrusion, spray deposition, or by mixing with a structural component through one or more of the printing heads on the printer assembly 358. Prior to gamma irradiation membrane and/or diagnostic strips 364 can be prepositioned onto the three-dimensional printing tray 362. The three-dimensional printing assembly 358 can spray deposit proteins and/or other concentrated ultra-filtered materials onto the membranes strips for use in diagnostic analysis. Additionally other structural components can be added to the membrane strips by layer-by-layer additive printing of material from the printer assembly 358. After the printing onto the three-dimensional printed membrane strips 364 has been completed the three-dimensional printing tray 362 and printed membrane strips 364 can be removed via a transfer hatch 366 on the three-dimensional printer 360 wall.

Figure 10:
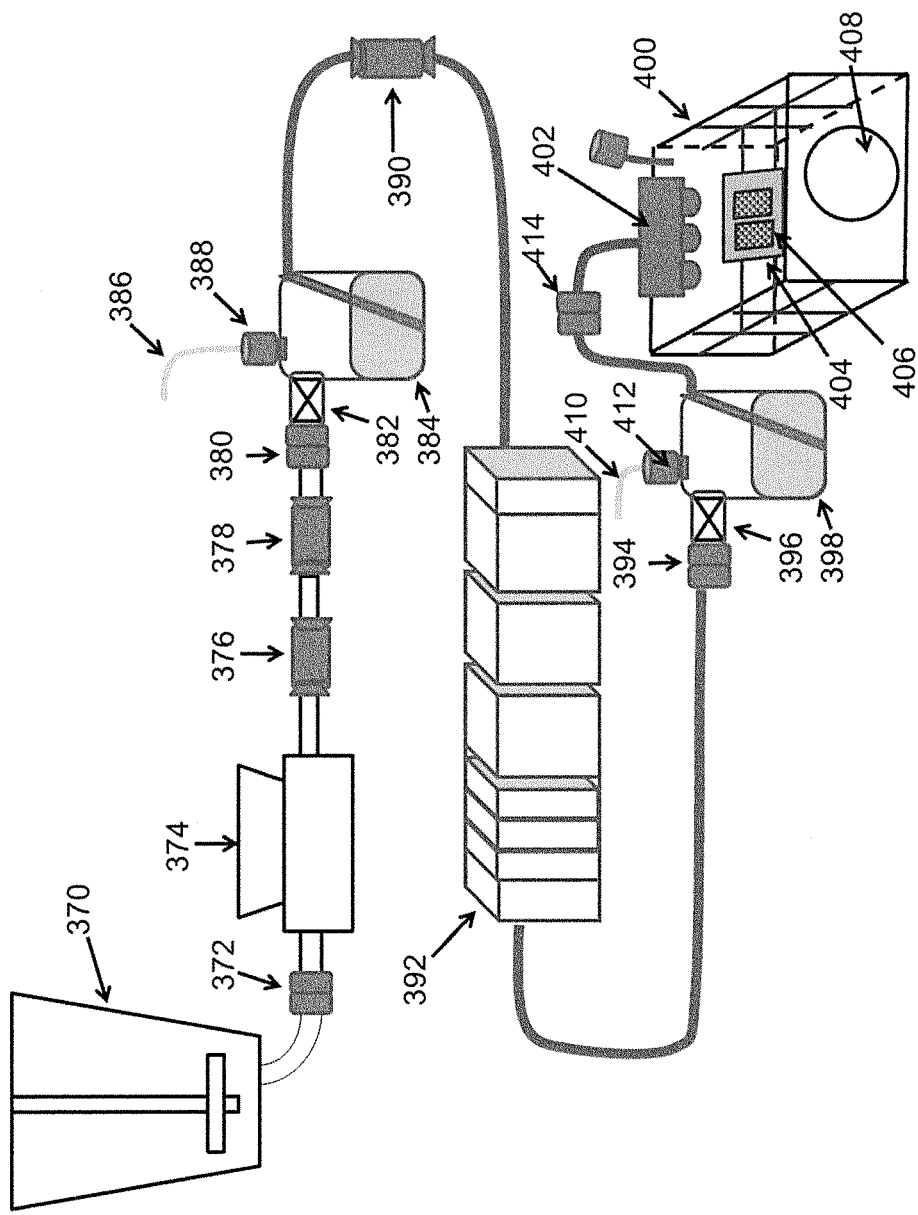
FIG. 10 illustrates an embodiment of a single-use bioreactor, a centrifugation assembly, a filtration assembly, a membrane adsorber assembly, and a crossflow assembly connected to a single-use three-dimensional printer via an aseptic connector to form a printed object.

FIG. 10 shows an embodiment of a single-use bioreactor, a centrifugation assembly, a filtration assembly, a membrane adsorber assembly, and a cross flow assembly connected to a single-use three-dimensional printer via an aseptic connector to form a printed object. This embodiment comprises a gamma irradiated assembly containing a single-use bioreactor 370 which is connected to a continuous flow centrifuge 374 via an aseptic connector 372. The continuous flow centrifuge removes the heavy particulates from the bioreactor harvest and allows the supernatant to continue into the filtration train assembly. The filtration train can comprise a plurality of filters including but not limited to a depth filter (not shown), a pre-filter 376, and a sterilizing grade filter 378. The filter train is connected to a surge vessel container 384 via an aseptic connector 380. The surge vessel container 384 fills with the material filtered from the bioreactor which can be driven by a constant pressure or constant flow source. A sterilizing grade vent filter 388 allows the surge vessel container 384 to vent during filling. After the filtration process is complete or the surge vessel container 384 is full, the valve 382 to the filter train is closed and a regulated compressed air line 386 is fluidly connected to the sterilizing grade air filter 388. The pressure drives the liquid up a dip tube and into a tubing piece which is connected to a pre-sterilized membrane adsorber 390. The membrane adsorber 390 is a chromatographic membrane carrying functional groups for the reversible binding of biomolecules. The desired molecules can be captured with the membrane adsorber and eluted at a later time or undesirable molecules can be removed by membrane adsorption before further processing. The membrane adsorber 390 can be connected to a pre-sterilized cross flow assembly 392. The cross flow assembly 392 can comprise a plurality of microfiltration and/or ultrafiltration cassettes in varying sizes. The cross flow assembly is connected to a surge vessel container 398 via an aseptic connector 394. The surge vessel container 398 fills with the material filtered and/or concentrated from the cross flow assembly 392 which can be driven by a constant pressure or constant flow source. A sterilizing grade vent filter 412 allows the surge vessel container 398 to vent during filling. After the cross flow processing is complete or the surge vessel container 398 is full, the valve 396 to the cross flow assembly is closed and a regulated compressed air line 410 is attached to the sterilizing grade air filter 412. The pressure drives the liquid up a dip tube and into a tubing piece which is connected via an aseptic connector 414 to the three-dimensional printing assembly 400.

The material from the surge vessel container 398 can be deposited onto the three-dimensional printing tray or printing platform 404 in a precise location through extrusion, spray deposition, or by mixing with a structural component through one or more of the printing heads on the printer assembly 402. Prior to gamma irradiation membrane and/or diagnostic strips 406 can be pre-positioned onto the three-dimensional printing tray 404. The three-dimensional printing assembly 402 can spray deposit proteins and/or other concentrated ultra-filtered materials onto the membranes strips for use in diagnostic analysis. Additionally other structural components can be added to the membrane strips by layer-by-layer additive printing of material from the printer assembly 402. After the printing onto the three-dimensional printed membrane strips 406 has been completed the three-dimensional printing tray 404 and printed membrane strips 406 can be removed via a transfer hatch 408 on the three-dimensional printer 400 wall.

Figure 11:
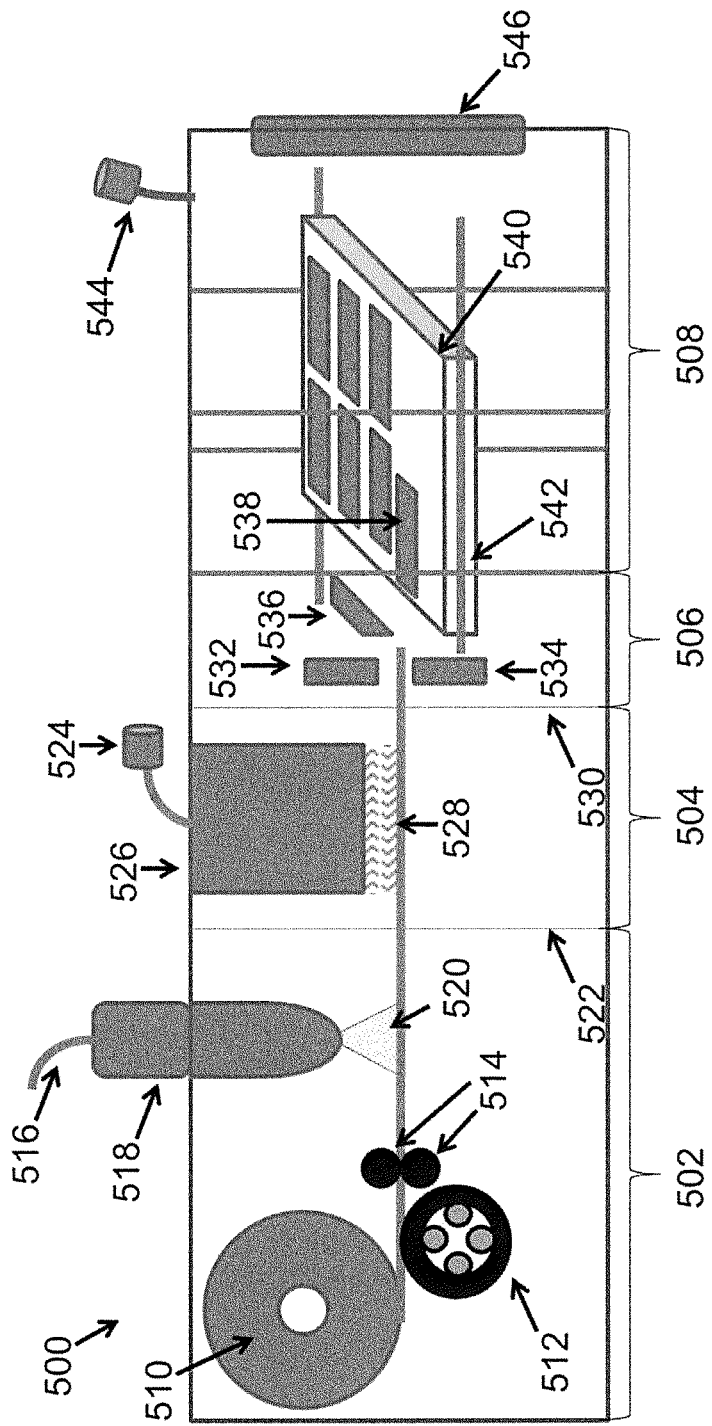
FIG. 11 illustrates an embodiment of a single-use three-dimensional membrane printer with a three-dimensional axis framework for a stacking/storage tray.

FIG. 11 shows an embodiment of a single-use three-dimensional membrane printer with a three-dimensional axis framework for a stacking or storage tray. This embodiment shows a gamma irradiated membrane printing assembly 500 containing a membrane dispensing and print section 502 which has a membrane roll 510 suspended by a dowel (not shown). The membrane from the membrane roll 510 is dispensed utilizing a magnetic roller assembly 512 which mates to an external motor with a magnetic head (not shown) to drive the movement of the membrane through the membrane printing assembly 500. The motor speed of the external motor controls the speed at which the magnetic roller assembly 512 moves and at which the membrane is dispensed from the roll 510. An assembly of passive rollers 514 keeps the membrane straight and at tension as the membrane is dispensed. These passive rollers 514 can be present throughout the membrane printing assembly 500 to maintain tension and a straight path for the membrane.

Fluid material, which may be provided by a single-use bioreactor, enters the printing head 518 from the tubing 516 under pressure. The electronically controlled printing head 518 dispenses the fluid 520 onto the membrane with a specific pattern. The magnetic roller assembly 512 can reverse the membrane if multiple passes of fluid and/or structural deposition of material onto the membrane is required for the process. The printed membrane section then moves through an opening in a wall 522 where it enters the drying section of the assembly 504 where the membrane can undergo drying by utilizing heated or cooled sterile air.

A sterilizing grade vent filter 524 can be utilized to bring air that has been heated or cooled from an outside source. The air can enter into the membrane printing assembly 500 through a diffuser block 526, wherein the diffuser block 526 takes the incoming air and diffuses it so that there is an even application of the heated or cooled air 528 across the membrane to allow for even drying. The membrane section then passes through an opening in a wall 530 to a cutting section 506 of the membrane printing assembly 500. Both walls 522 and 530 serve as a physical barrier to prevent the overheating of components within the membrane assembly if heated air is used to dry the printed materials on the membrane.

In a simple embodiment the walls 522 and 530 can be a simple layer of thin plastic. In a more complex embodiment the walls 522 and 530 can contain a thermal insulation to prevent the transfer of heat to other areas of the assembly. In an even more complex embodiment the walls 522 and 530 can contain a capillary network of tubing which can be connected to a cooling or heated water source to prevent thermal transfer and offset the temperature of the air used to dry the printed membrane. The walls of the entire three-dimensional printing assembly can also be jacketed to maintain a constant desired temperature.

The cutting section 506 contains at least two movable clamps including one top clamp 532 and one bottom clamp 534. The top clamp 532 and the bottom clamp 534 can clamp down onto the membrane in a specified section preferably one that has not undergone printing and allows for a rigid hold so that the membrane can be cut into sections by a knife cutting assembly 536. A plurality of cutting knives or cutting dies in the knife cutting assembly 536 can cut the membrane into horizontal and/or vertical sections, or die-cut shapes to a specified sizing as required. The knife cutting assembly 536 can feature passive knives under the membrane which cuts the membrane into sized vertical strips as the membrane is fed through it. A horizontal cutting knife can be mechanically actuated to cut the membrane strips at a specific length. The top clamp 532 the bottom clamp 534 and an actuated horizontal cutting knife from the knife cutting assembly 536 can all be driven pneumatically from an external air pressure source or magnetically driven from an external mechanical source. As the membrane is cut by the knife cutting assembly 536 the membrane strips 538 falls into a collection tray or collection device 540 in the membrane strip collection section 508 of the assembly. This collection tray can move along a 3 axis framework 542 to stack the membrane strips 538 as they fall into the tray.

In this assembly multiple trays, as preferred collection device, can be utilized along the same three axis framework to increase the area of the membrane strips collected into the trays. The trays can also have a rotatable feature where the internal tray can be rotated along the holding platform to increase the area where the membrane strips 538 can be stacked. In other words the trays may have two linear degrees of freedom and one rotational degree of freedom. The number of trays and the sizing type of trays used can be determined by the size of the membrane roll, the size and the number of strips that need to be cut, and if the printed material on the membrane is sensitive and cannot undergo stacking or can only undergo limited stacking. The entire membrane printing assembly can be maintained at ambient pressure through a sterilizing grade vent filter 544. After the printing process has completed and the membranes strips 538 are placed in the collection trays 540 the trays can be removed through the transfer hatch 546. A sterile transfer bag not shown can be attached to the transfer hatch 546 if the maintenance of sterility is required.

Figure 12:
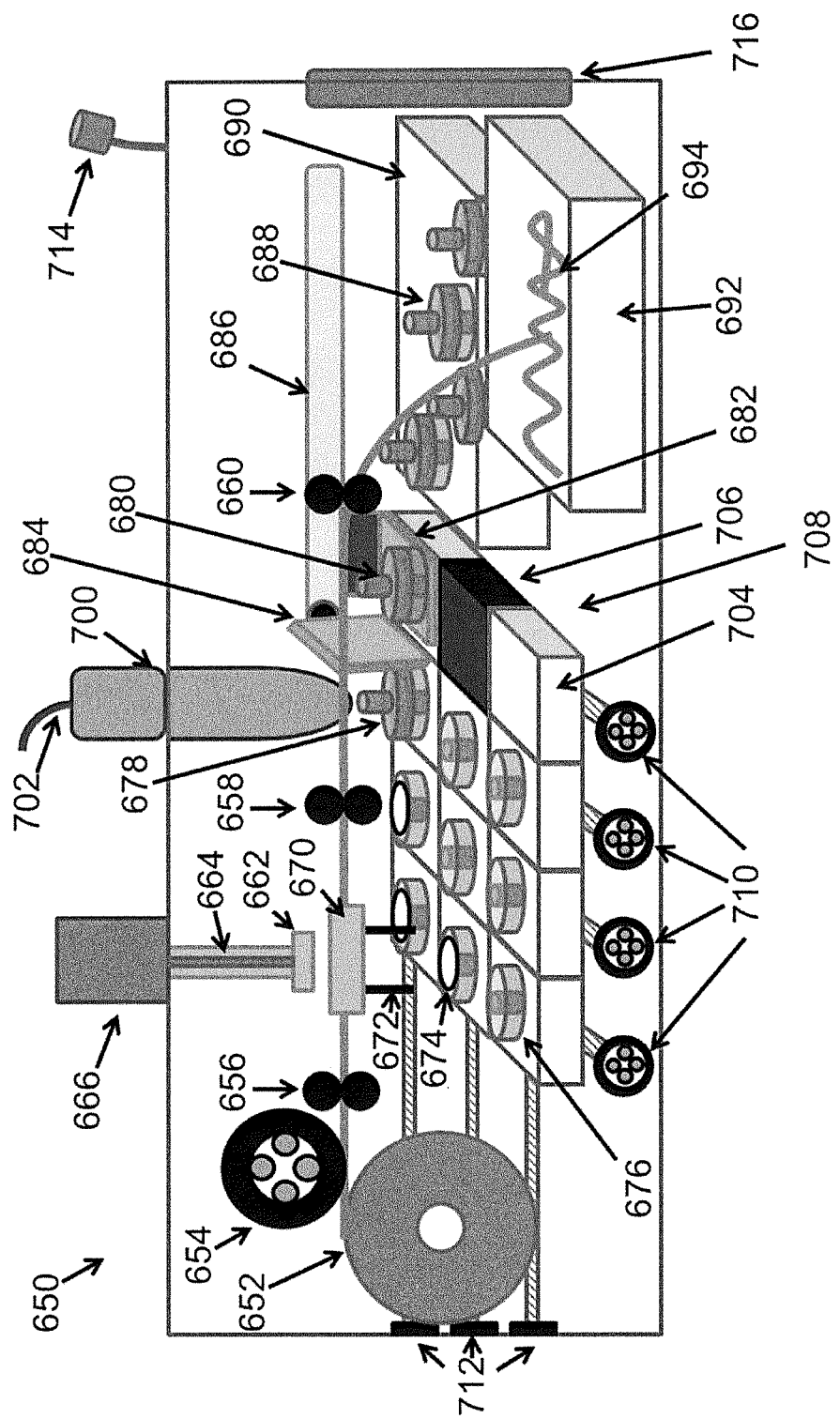
FIG. 12 illustrates an embodiment of a single-use three-dimensional printer with a multi-segmented tile printing platform and a membrane dispenser to form a plurality of printed filtration devices.

FIG. 12 illustrates an embodiment of a single-use three-dimensional printer with a multi-segmented tile printing platform and a membrane dispenser to form a plurality of printed filtration devices.

This embodiment shows a gamma irradiated filter device printing assembly 650 containing a membrane dispenser which has a membrane roll 652 suspended by a dowel (not shown) and only takes up a portion of the horizontal space within the printing assembly. The membrane from the membrane roll 652 is dispensed utilizing a magnetic roller assembly 654 which mates to an external motor with a magnetic head (not shown) to drive the movement of the membrane through the filter device printing assembly 650. The motor speed of the external motor controls the speed at which the magnetic roller assembly 654 moves and at which the membrane is dispensed from the roll 652. An assembly of passive rollers 656, 658, and 660 keeps the membrane straight and at tension as the membrane is dispensed. These passive rollers 656, 658, and 660 can be present throughout the filter device printing assembly 650 to maintain tension and a straight path for the membrane. In a more complex embodiment a pleating device (not shown) may be utilized to form pleats with the membrane, which are used to increase the surface area of the membrane available within a limited space.

The membrane sheet from membrane roll 652 is spooled out into a holder 670 where a cutting die 662 presses down utilizing the force from an internal shaft 664 from an externally mounted piston 666 to cut through the membrane. This forms a die-cut membrane shape 674 which falls through the holder 670 and maintains placement via guide bars 672. The die-cut membrane 674 is guided to a partially formed filter device 676 which was printed by a three-dimensional printing head 700 by layer-by-layer additive printing of a plastic material, preferably polypropylene by a heated extrusion head, but could also be made of Polylactic acid or polylactide (PLA), Acrylonitrile butadiene styrene (ABS), or other printable material which can be fed to the printing head 700 as a spooled material 702, heated and extruded onto the printing platform. The partially formed filter device 676 can include an opening for the fluid to pass through, material to form the body of the filter device, a cavity to fit the die cut membrane 674, and structural material to assist in the building of overhanging structures such as a bridge. Biologic material originating from a bioreactor including proteins, ultra-filtered materials, or other materials can be spray deposited using a separate printing head onto the membrane prior to die-cutting or prior to the completion of the filter device.

After the die-cut membrane 674 is placed on the cavity in the partially formed filter device 676 the individual tiles 704 of the multi-segmented printing platform 708 can be moved utilizing magnetic roller assemblies 710 and 712 which mates to an external motor with a plurality of magnetic heads (not shown) to drive the movement of the individual tiles 704 via a series of rotating screws in a stepwise movement through the filter device printing assembly 650 which mimics a sliding tile puzzle. The multi-segmented printing platform 708 has an empty space 706 which allows for all individual tiles 704 to be moved to all possible positions on the printing platform. The individual tiles 704 containing the partially formed filter devices 676 containing the die-cut membranes 674 are moved in a stepwise movement to the printing head 700 which occupies a portion of the horizontal space not taken up by the membrane dispensing assembly. The printing head 700 then seals the die-cut membrane 674 by extruding material around the rim of the partially formed filter device 676. The printing head 700 then prints the remainder of the filter device by layer-by-layer additive printing to form a completed filter device 678 containing a sealed membrane layer. In a more complex embodiment the die-cut membrane 674 may be ultrasonically welded onto the rim of the partially formed filter device 676 using an ultrasonic welding device (not shown) described in FIG. 32. The ultrasonic welding device (not shown) may additionally ultrasonically weld the at least one bottom part of a partially formed filter device 676 to the at least one top part of corresponding partially formed filter device (not shown) to form a completed filter device 678. The ultrasonic welding device (not shown) may additionally ultrasonically weld a pleated section of membrane (not shown) together to form a pleated membrane assembly (not shown) prior to assembly into a pleated filter device (not shown). The completed filter device individual printing platform tile is moved into position in a stepwise movement to enter the completed filter device bin 690. A rigid blade 682 cuts the bottom of the completed filter device 680 to remove it from the printing platform tile. A printed structural element, like a raft, could be utilized to ease the process of removing the completed filter device 680 with a clean break from the rest of the printing platform to reduce any potential defect from the cutting/removal process. A movable guide on a hinge 684 can push the completed filter device into the completed filter device bin 690. This guide can go along the guide path 686 and push completed filter devices 688 throughout the bin 690. The movable guide can be controlled externally by a magnetic motor assembly or an insertable shaft motor (not shown).

The waste components of the membrane roll after being die-cut can be spooled into a membrane waste bin 692 which can collect the remaining membrane 694 and make for easy disposal after the printing process has completed. The entire membrane printing assembly can be maintained at ambient pressure through a sterilizing grade vent filter 714. After the printing process has completed the completed filter devices 688 located in the holding bin 690 can undergo sterile transfer using the transfer hatch 716 if the maintenance of sterility is required.

FIGS. 13A-13F show an embodiment of the connections steps to insert the printing head into the sterile three-dimensional assembly body.

FIG. 13A is a side view of an embodiment that shows a gamma irradiated three-dimensional printer assembly body 550, with a rigid or flexible wall, containing a printing head insertion assembly 548 containing a cap assembly 552 internal to three-dimensional printer assembly with an internal dip tube 554. The external portion of the printing head insertion assembly 548 contains a removable cap 560, a fluid inlet port 556, and a fluid outlet port 558.

FIG. 13B is a side view of the removable cap 560' being removed from the printing head insertion assembly 548 and the electronically controlled printing head 562 being inserted into the assembly.

FIG. 13C is a side view of the electronically controlled printing head 562 inserted into the printing head insertion assembly 548 and twisted one position into place 564.

FIG. 13D is a side view of the printing head insertion assembly 548 with a tubing piece 566 inserted into the fluid inlet port 556 where a chemical sterilant or sanitizer 568 fills the cap assembly 552 sterilizing the internal section of the electronically controlled printing head. The chemical sterilant or sanitizer 568 can comprise a liquid like 30% hydrogen peroxide, or may comprise a gas sterilant such as vaporized hydrogen peroxide or ethylene oxide.

FIG. 13E is a side view of the printing head insertion assembly 548 with a tubing piece 570 inserted into the fluid outlet port 558 where the chemical sterilant or sanitizer is removed by vacuum pressure after the period of time required to sterilize the printing head is completed. The internal dip tube 554 can be utilized to remove a fluid chemical sterilant or sanitizer or condensate from a gas chemical sterilant.

FIG. 13F is a side view of the printing head insertion assembly where the printing head is twisted 572 into the second position where the cap assembly 552' drops into the interior of the three-dimensional printer assembly body. The cap assembly 552' can be moved manually to a holding bin within the three-dimensional printer assembly body by tilting the three-dimensional printer assembly until the cap assembly 552' falls into place. The sterilized printing head 562 is ready to print within the three-dimensional printed assembly.

FIGS. 14A-14E show an embodiment of the setup process for a flexible wall three-dimensional printer from the packed shipping configuration.

FIG. 14A is a side view of an embodiment that shows a gamma irradiated three-dimensional printer assembly 600 with flexible walls that is folded flat in a configuration for shipping. The entire assembly can be enclosed in multiple gamma irradiatable bags for ensuring sterility of the bags when moving from the receiving to the end use facility. The shipping configuration consists of the air bags completely deflated or the actuators and/or magnetic drivers in the minimal position. The bag handles 602 and 604 on the top of the three-dimensional printer assembly 600 are folded over. The printing head insertion assembly 606 rest inside of the printing platform tray during shipping. The sterilizing grade venting filter 608 is laid on its side and is capped off with cap 610. A bag integrity testing device, preferably a Sartocheck® automated bag integrity testing unit, can be utilized by inserting the bag assembly between two plates containing a fleece layer to test the integrity of the bag seal and ensure there are no leaks prior to use.

FIG. 14B is a side view of an embodiment that shows a gamma irradiated three-dimensional printer assembly 600' with the handles extended and the operator pulling the handles 602' and 604' upwards. The three-dimensional printing assembly bag chamber can be inflated with sterile air from an external source not shown. The folded screws or tracks forming the three axis framework and the internal support skeleton can be manually snapped into place by the operator by pulling up and pushing down on the external handles 602' and 604'. The printing head insertion assembly 606 is supported by an internal crossbar support that can also be snapped into place by the operator. The cap 610 on the venting air filter 608 can be removed after the support skeleton is in place to ensure that the flexible walls do not collapse when vented to the outside.

FIG. 14C is a side view of an embodiment that shows a threaded screw assembly 620 making up the three axis framework where the printing platform is precisely moved. The threaded screw assembly 620 is in a folded configuration for shipping where the first threaded screw section 622 is separated by the second threaded screw section 624 by a hinge 626 and an internal locking mechanism 628.

FIG. 14D is a side view of an embodiment that shows a threaded screw assembly 620' which is folded back into a vertical position using hinge 626 by the operator pulling back on the external handles to unfold the bag. The threaded screw assembly 620' is in a folded back where the second threaded screw section 624' is in a vertical position and is in line with the first threaded screw section 622.

FIG. 14E is a side view of an embodiment that shows a threaded screw assembly 620" where the second threaded screw section 624' is pushed down to mate with the first threaded screw section 622 covering the hinge assembly 626 and the locking mechanism while forming a single threaded screw body 620". The locking mechanism 628 clicks into place ensuring that the threaded screw cannot be detached unless the locking mechanism is disengaged. The operator pulls the external handles down to achieve the locking of the threaded screws for the three axis framework and/or other internal support elements forming the internal support structure for the three-dimensional printer assembly.

FIGS. 15A-15D show an embodiment of the movements of the x-axis, y-axis, and z-axis controls of the three-dimensional printing platform utilizing hydraulically-driven actuators.

FIG. 15A is a side view of a basic embodiment of a manually controlled hydraulically driven three-dimensional printing device 800 having a sterile chamber where a three-dimensional printing platform 814 containing a printing tray 824, as an exemplary printing platform, is pushed and/or pulled into a precise position by the hydraulic actuators 810, 812, 816, 820 for three-dimensional printing by a plurality of printing heads 838. In this basic embodiment the internal hydraulic actuators 810, 812, 816, 820 are controlled and driven by an external set of manual actuators 802. In more complex embodiments the manually-controlled external set of manual actuators 802 may be replaced by an automated computer-controlled setup (not shown). Some manual actuators 802 may be sized to hold a volume of fluid equivalent to the capacity of the corresponding internal hydraulic actuator, as is the case with hydraulic actuators 816 and 820. Other manual actuators 802 may additionally be sized to hold a volume of fluid equivalent to or larger than the combined capacities of multiple corresponding internal hydraulic actuators, as is the case with actuators 810 and 812, where multiple internal hydraulic actuators 810 and 812 are uniformly controlled by an individual external manual actuator 802. The hydraulic actuators setup may be filled with an incompressible fluid, such as sterile filtered purified water, to drive the internal hydraulic actuators 810, 812, 816, 820. Hydraulically-driven actuators have the following advantages: they have a higher pressure-to-weight ratio over pneumatic actuators, they can hold force and torque constant without the pump supplying more fluid or pressure, they can produce a higher force with respect to a pneumatic cylinder of equal size, and they can be placed at a greater distance away from the device 800 with minimal loss of power. The disadvantage is the potential for leakage in the tubing lines within the setup. In this embodiment a sterile drain 830, containing a sterilizing-grade filter 832, is positioned in the bottom-most portion of the chamber to remove any potential leakage of hydraulic fluid from the setup. Specialty hydraulic fluid oils may be utilized for particular applications where high-weight transfers are required but their use in a clean, sterile environment would require additional precautions for tubing strength and secure connections to prevent the leakage of hydraulic fluids into the sterile chamber. A hydraulic actuator provides unidirectional force through a unidirectional stroke. Examples of hydraulic actuators for the following setup include but are not limited to linear actuators, rolling diaphragm actuators, sterilizable linear actuators, sterilizable syringes, hydraulic rotary actuator, and hydraulic rotary vane actuators. In this embodiment the three-dimensional printing platform 814 and the printing tray 824 are at the lowest height of the compressed y-axis hydraulic actuators. The hydraulically-driven three-dimensional printing device 800 utilizes an external set of manual actuators 802 to drive the internal hydraulic actuators 810, 812, 816, and 820. The hydraulic tubing lines are filled with a sterile filtered fluid, such as sterile filtered purified water, through a filter assembly 804. The filter assembly 804 may contain a sterilizing-grade filter through which the fluid input is provided to fill the tubing lines 806, hydraulic actuators 802, 810, 812, 816, 820, and any fluid reservoirs (not shown). The filter assembly 804 may contain a 'T' connection with a valve to separate the incoming fluid line from the rest of the hydraulic assembly. A sterilizing-grade vent filter (not shown) may be employed to properly vent the tubing lines 806, hydraulic actuators 802, 810, 812, 816, 820, and fluid reservoirs (not shown) of any residual air during the filling procedure. The hydraulic tubing lines 806 enter into the sterile chamber through a port 808 in the chamber. The hydraulic tubing lines 806 connect to the y-axis controlling hydraulic actuators 810 and 812, which vertically raise and lower the height of the printing platform 814 and printing tray 824, to the x-axis controlling hydraulic actuator 816, which moves the printing tray 824 horizontally, and to the z-axis hydraulic actuator 820, which moves the printing tray horizontally and orthogonally to the direction in which the actuator 816 move the printing tray. In this embodiment the x-axis hydraulic actuator 816 is connected to a printing tray assembly 822 with a connection piece 818 that moves along on a track on the printing platform 814. The z-axis hydraulic actuator 820 is connected to the printing tray assembly 822 and moves along with it while moving the printing tray 824 along a track on the printing tray assembly 822. This precisely positions the printing tray 824 for three-dimensional printing through the dispensing of material from a plurality of printing heads 838.

FIG. 15B is a side view of a basic embodiment of a manually-controlled hydraulically driven three-dimensional printing device 800. The external set of manual actuators 802' are manually depressed by an operator, which drives the internal hydraulic actuators to move into positions 810', 812', 816', and 820'. The hydraulic fluid, which in this exemplary embodiment is sterile filtered purified water, enters into the chamber through tubing lines 806 and places pressure on the actuators causing the piston rods from the actuators to extend thus moving the positions of the 3-axis framework to position the printing tray for the plurality of printing heads 838. In this embodiment the three-dimensional printing platform 814 and the printing tray 824 are at the highest height of the extended y-axis hydraulic actuators 810' and 812'. In this embodiment a minor leakage of hydraulic fluid from an internal tubing line connection is removed by adding a vacuum assembly collection flask 834 and a vacuum pump 836 to the sterile drain assembly 830. The vacuum assembly collection flask 834 is connected to the sterilizing-grade filter 832 on the sterile drain assembly 830. The vacuum pump 836 is turned on and the hydraulic fluid material that leaked into the sterile chamber is removed and discarded from the vacuum assembly collection flask 834. Additional hydraulic fluid may be added to the hydraulic fluid tubing line 806 using the filter assembly 804. In more complex embodiments the manually-controlled external set of manual actuators 802 may be replaced by an automated computer-controlled setup (not shown).

FIG. 15C is a top view of the hydraulically-driven three-dimensional printing device 800 where the printing tray 824 is moved along the x-axis and z-axis with corresponding hydraulically driven actuators 816 and 820. In this embodiment the x-axis hydraulic actuator 816 is in a fixed position on the printing platform 814. The x-axis hydraulic actuator 816 is connected to the printing tray assembly 822 with a connection piece 818 that moves the entire printing tray assembly 822 along on a track 826 on the printing platform 814. The z-axis hydraulic actuator 820 is connected to the printing tray assembly 822 and moves along with it while moving the printing tray 824 along a track 828 on the printing tray assembly 822. This precisely positions the printing tray 824 for three-dimensional printing.

FIG. 15D is a top view of the hydraulically driven three-dimensional printing device 800 where the printing tray 824 is moved along the x-axis and z-axis with corresponding hydraulically driven actuators 816' and 820'. In this embodiment the x-axis hydraulic actuator 816' has extended and moved the printing tray assembly 822 horizontally across the printing platform 814. The z-axis hydraulic actuator 820' has extended and moved the printing tray 824' in the z-axis direction across the printing tray assembly 822. This precisely positions the printing tray for three-dimensional printing.

FIGS. 16A-16G show several embodiments of printing with multiple degrees of freedom.

FIG. 16A is a side view of a three-dimensional printer 840 with a hydraulically- and/or pneumatically-linear-actuator-driven printing platform 846. In this embodiment at least two hydraulically- and/or pneumatically-driven linear actuators 842 and 844 are positioned on either side of the printing platform 846. The hydraulically- and/or pneumatically-driven linear actuators 842 and 844 are uniformly extended and raise the printing platform 846 up, thereby positioning the printing tray 848 in the precise location for printing via the printing head 850.

FIG. 16B is a side view of a three-dimensional printer 840' with a hydraulically- and/or pneumatically-linear-actuator-driven printing platform 846'. The hydraulically- and/or pneumatically-driven linear actuators 842' and 844' are extended at different heights resulting in the printing platform 846' and printing tray 848' to be positioned at an angle in relation to the printing head 850. The positioning of the printing tray 848' at a plurality of angles allows for additional degrees of freedom and increased flexibility for printing along multiple axes for three-dimensional printing with respect to a standard three-axis-coordinate printing system. This will assist in the building of structures, such as bioprinted structures, which may require additional degrees of freedom for proper formation of a biological manufactured product.

FIG. 16C is an alternate embodiment of a side view for a three-dimensional dimensional printer 840" with a hydraulically- and/or pneumatically-linear-actuator-driven printing platform 846". The hydraulically- and/or pneumatically-driven linear actuators 842" and 844" are extended into different positions at different heights resulting in the printing platform 846" and printing tray 848" to be positioned at an alternate angle in relation to the printing head 850 with respect to the angle shown in FIG. 16B.

FIG. 16D is a side view of a three-dimensional dimensional printer 860 with a printing head 866 featuring an articulating axis joint 868. The articulating axis joint 868 allows for the positioning of the printing head dispenser 870 at a plurality of angles in relation to the printing tray 864 located on the printing platform 862, which allows for additional degrees of freedom and increased flexibility for printing along multiple axes for three-dimensional printing with respect to a standard three-axis-coordinate printing system. The movement of the articulating axis joint 868 on the printing head dispenser 870 may be driven by a hydraulic, pneumatic, magnetic, electric, and/or other internal/external force. The articulating axis joint 868 may be a hinge joint or a ball and socket joint.

FIG. 16E is an alternate embodiment (with respect to view D') of a side view for a three-dimensional dimensional printer 860' with a printing head 866 featuring an articulating axis joint 868'. The articulating axis joint 868' is moved into an alternate position which allows for the printing head dispenser 870' to be positioned at a different angle in relation to the printing tray 864.

FIG. 16F is a side view of a three-dimensional dimensional printer 872 with a printing head 874 featuring a plurality of articulating axis joints 876 and 878. The at least two articulating axis joints 876 and 878 on the printing head 874 allow for the positioning of the printing head dispenser 880 at a plurality of angles in relation to the printing tray 888. A three-dimensional printer with a plurality of articulating axis joints 876 and 878 allows for the top portion of the printing head 874 to remain in a fixed position through a fixed port on the top of the single-use container as well as for a fixed position of the printing tray 888, while allowing the multi-axis positioning of the printing head without the required movements and positioning by a gantry assembly.

FIG. 16G is a side view of a three-dimensional dimensional printer 872 with a hydraulically- and/or pneumatically-linear-actuator-driven printing platform 886 and a printing head 874 featuring a plurality of articulating axis joints 876 and 878. The at least two articulating axis joints 876 and 878 on the printing head 874 allow for the positioning of the printing head dispenser 880 at a plurality of angles in relation to the printing tray 888. The hydraulically-and/or pneumatically-driven linear actuators 882 and 884 are extended at different heights resulting in the printing platform 886 and printing tray 888 to be positioned at an angle in relation to the printing head dispenser 880. The multi-axis positioning of the printing tray 888 at a plurality of angles as well as the multi-axis positioning of the printing head dispenser 880 allows for additional degrees of freedom and increased flexibility for printing with respect to a standard three-axis-coordinate printing system.

FIGS. 17A-17G show several embodiments of moving print platforms for printing with multiple degrees of freedom.

FIG. 17A is a top view of a printer chamber setup 900 containing a printing tray 902 with a rotational shaft at the center and a hydraulic, pneumatic, electric, and/or magnetically controlled linear actuator 904 set at an angle with the printing tray 902, where the linear actuator shaft connects to the printing tray 902 with a rotating connection joint 906. The linear actuator shaft is in an idle position.

FIG. 17B is a top view of a printer chamber setup 900' where the linear actuator 904' shaft is extended, thereby pushing on the rotating connection joint 906' and causing the printing tray 902' to rotate along the shaft at the center away from the linear actuator 904'. This extension of the linear actuator 904' causing the rotation of the printing tray 902' allows for an additional degree of freedom for movement during the printing process from a printing head. This rotational movement may allow a fixed printing head previously confined to a standard three-axis control setup by gantry positioning to now provide the ability to make curved features, which are present throughout biological and/or biologically-inspired components but are difficult to produce at high resolution with a standard three-axis positioning system.

FIG. 17C is an alternate view of a printer chamber setup 900" where the linear actuator 904" shaft is contracted, thereby pulling on the rotating connection joint 906" and causing the printing tray 902" to rotate along the shaft at the center towards the linear actuator 904". This contraction of the linear actuator 904" allows for a rotation of the printing tray 902" during the printing process.

FIG. 17D is a top view of a printer chamber setup 908 where the square printing tray 910 undergoes a rotation movement 912 via a moving shaft at the center of the square printing tray 910. The center shaft of the square printing tray 910 may be powered by a rotational motor driven by hydraulic, pneumatic, electric, or magnetically controlled methods (not shown). This rotational movement may allow a fixed printing head to make curved, circular, elliptical, parabolic, hyperbolic, or spheroidal features.

FIG. 17E is a top view of a printer chamber setup 914 where the circular printing tray 916 undergoes a rotation movement 918 via a moving shaft at the center of the circular printing tray 916. The center shaft of the circular printing tray 916 may be powered by a rotational motor driven by hydraulic, pneumatic, electric, or magnetically controlled methods (not shown).

FIG. 17F is a side view of a printer chamber setup 920 where the printing tray 924 is connected to a rotating and articulating joint 926 on the printing platform 922. The rotating and articulating joint 926 may be a hinge joint or a ball and socket joint. The rotating and articulating joint 926 can move in a rotational direction 928 and/or a vertical motion 930, which changes the position of the printing tray 924 to a plurality of angles relative to a fixed printing head. The rotating and articulating joint 926 may be powered by a rotational motor driven by hydraulic, pneumatic, electric, or magnetically controlled methods (not shown).

FIG. 17G is a side view of a printer chamber setup 932 where the printing tray 934 is connected to a rotating and articulating joint 936 on the printing platform. The rotating and articulating joint 936 can move in a rotational direction and/or a vertical motion 942, which is controlled by a plurality of linear actuators 938 and 940 connected to the underside of the printing tray 934. The linear actuators 938 and 940 may be extended or contracted to different heights, causing the position of the printing tray 934 to be raised or lowered at a plurality of angles relative to a fixed printing head. The connection of the linear actuators 938 and 940 to the underside of the printing tray 934 may be implemented via a track (not shown), which allows the linear actuator shafts to move freely when the printing tray 934 is rotated while remaining connected, in order to cause the movement of the printing tray 934 to the desired angle during the printing process. The rotating and articulating joint 936 as well as the linear actuators 938 and 940 may be powered by a rotational motor driven by hydraulic, pneumatic, electric, or magnetically controlled methods (not shown).

FIGS. 18A-18M show several embodiments of printer designs. The embodiments of the printer designs are simplified to show the variety of methods for dispensing material within a sterile chamber. More complex designs of each of these embodiments may contain sterilizing grade vent filters, sterile drains, transfer hatches, and other accessories described in the other figures.

FIG. 18A is a side view of a printer chamber setup 1000 containing a three-axis gantry positioning system utilizing at least one vertical linear actuator 1002 to adjust the height of the printing platform 1004. The printing platform 1004 may support a horizontal linear actuator 1006, a second horizontal linear actuator 1008 orthogonal to linear actuator 1006 and a moving printing tray 1010. The horizontal linear actuator 1006 may be utilized to position the printing tray 1010 along the x-axis and the diagonal linear actuator 1008 may be utilized to position the printing tray 1010 along the z-axis. The three-axis gantry positioning system is utilized for printing with a fixed printing head 1012 within the sterile printer chamber setup 1000. The linear actuators may be driven by hydraulic, pneumatic, electric, or magnetically controlled methods (not shown). This embodiment is a minimal design where only three linear actuators may be utilized to position the 3-axis positioning system, where in other embodiments a plurality of actuators including more than three actuators may be utilized.

FIG. 18B is a side view of a printer chamber setup 1020 containing a hybrid three-axis gantry positioning system utilizing at least one vertical inflatable bag assembly 1022 to adjust the height of the printing platform 1024. The vertical inflatable bag assembly 1022 may contain a plurality of bags, which may be filled with a fluid (air, gas, or liquid) to vertically position the printing platform 1024. The printing platform 1024 may support a horizontal actuator 1026, a second horizontal actuator 1028 orthogonal to horizontal actuator 1026 and a moving printing tray 1030. The horizontal actuator 1026 may be utilized to position the printing tray 1030 along the x-axis and the second horizontal actuator 1028 may be utilized to position the printing tray 1030 along the z-axis. The three-axis gantry positioning system is utilized for printing with a fixed printing head 1032 within the sterile printer chamber setup 1020. The inflatable bag assembly 1022 may be driven by hydraulic, pneumatic, or chemical methods (not shown), while the actuators may be driven by hydraulic, pneumatic, electric, or magnetically controlled methods (not shown). In alternate embodiments a plurality of bag assemblies and actuators may be utilized.

FIG. 18C is a side view of a printer chamber setup 1040 containing a hybrid three-axis gantry positioning system utilizing at least one vertical magnetically-controlled assembly 1042 to adjust the height of the printing platform 1044. The magnetically-controlled assembly 1042 utilizes magnets, ferrimagnets, rare earth magnets, magnetic fields, or ferrofluids on the exterior of the printer chamber setup 1040, which are paired with an equivalent magnet on the printing platform 1044 within the interior of the printer chamber setup 1040. The printing platform 1044 may support a horizontal actuator 1046, a second horizontal actuator 1048 orthogonal to horizontal actuator 1046 and a moving printing tray 1050. The horizontal actuator 1046 may be utilized to position the printing tray 1050 along the x-axis and the second horizontal actuator 1048 may be utilized to position the printing tray 1050 along the z-axis. The three-axis gantry positioning system is utilized for printing with a fixed printing head 1052 within the sterile printer chamber setup 1040. The magnetically controlled assembly 1042 may be driven by mechanical, electric methods (not shown) or through the generation of magnetic fields (not shown), while the actuators may be driven by hydraulic, pneumatic, electric, or magnetically controlled methods (not shown). In alternate embodiments a plurality of magnetically-controlled assemblies and actuators may be utilized.

FIG. 18D is a side view of a printer chamber setup 1060 containing a multi-axis positioning system utilizing a robotic arm 1062 for positioning a printing tray 1074 with a plurality of articulating axis joints internal to the printer chamber setup 1060. In one embodiment the robotic arm 1062 may be controlled by utilizing an actuator 1064 to rotate a rotating base 1066. An additional actuator 1068 pushes on a support connected to an articulating joint moving the position of a printing platform 1072 and the printing tray 1074 vertically. An additional actuator 1070 pushes on a support connected to an articulating joint moving the position of the printing platform 1072 and printing tray 1074 at an angle in relation to the fixed printing head 1076. The actuators may be driven by hydraulic, pneumatic, electric, or magnetically controlled methods (not shown). In other embodiments a plurality of additional actuators may be used to position the printing tray 1074 on the printing platform 1072.

FIG. 18E is a side view of a printer chamber setup 1080 containing a hybrid three-axis gantry positioning system utilizing at least one vertical platform jack assembly 1082 to adjust the height of a printing platform 1090. In this embodiment the platform jack assembly 1082 contains a platform jack assembly screw 1083 in a fixed vertical position (known as a low-profile or offset platform jack) to control the positioning of the platform jack scissoring and the printing platform 1090 height. The platform jack assembly screw 1083 is connected to a connection component on the interior of the printer chamber setup 1080 via an extension assembly 1084 which may be a scissoring assembly, a suspension cylinder assembly, a hydraulic/pneumatic cylinder assembly, or a spring assembly. As the platform jack assembly 1082 is raised or lowered, the platform jack assembly screw 1083 changes horizontal position, thereby forcing the extension assembly 1084 inside of the sealed printer chamber 1080. The connection component assembly 1086 contains the interior connection component that drives the platform jack assembly screw 1083, the exterior connection component that connects to an external motor 1088 to turn the interior connection component, and a chamber interface component that connects the exterior of the chamber with the interior. The exterior connection component of the connection component assembly 1086 connects to the exterior of the printer chamber setup 1080 through magnets, or an internal and/or external shaft. In the magnetically-driven embodiment the chamber interface component may comprise a rigid plastic material, seals, and bearings to prevent wear along the interface between the exterior and interior of the chamber. In the internal and/or external shaft embodiment an external shaft may be inserted into the interior connection component (or vice versa) through the chamber interface component, which may comprise a rigid plastic material, seals, and bearings to prevent wear along the interface between the exterior and interior of the chamber. An external motor 1088 contains an external magnetic assembly (not shown) or an external shaft assembly (not shown), which is inserted into the connection component assembly 1086 to drive the platform jack assembly screw 1083 in order to change the position of the printing platform 1090. The printing platform 1090 may support a horizontal actuator 1092, a second horizontal actuator 1094 orthogonal to horizontal actuator 1092 and a moving printing tray 1096. The horizontal actuator 1092 may be utilized to position the printing tray 1096 along the x-axis and the second horizontal actuator 1094 may be utilized to position the printing tray 1096 along the z-axis. The three-axis gantry positioning system is utilized for printing with a fixed printing head 1098 within the sterile printer chamber setup 1080. The actuators may be driven by hydraulic, pneumatic, electric, or magnetically controlled methods (not shown). Various embodiments of the platform jack positioning may be utilized to control different axis positioning of the printer assembly.

FIG. 18F is a side view of a printer chamber setup 1100 containing a hybrid three-axis gantry positioning system utilizing at least one vertical platform jack assembly 1102 to adjust the height of a printing platform 1110. In this embodiment the platform jack assembly 1102 contains a standard platform jack assembly with a platform jack assembly screw 1103 that moves in both vertical and horizontal directions during the rotation of the screw 1103, which changes the height of the jack scissoring and of the printing platform 1110. The platform jack assembly screw 1103 is connected to a connection component on the interior of the printer chamber setup 1100 via a jointed extension assembly 1104, which may be a jointed scissoring assembly, a jointed suspension cylinder assembly, a jointed hydraulic/pneumatic cylinder, or a jointed spring assembly. The jointed extension assembly 1104 comprises an extension element connected to a hinged or ball and socket joint at either end, or a hinged or ball and socket joint in the middle of the assembly. As the platform jack assembly 1082 is raised or lowered, the platform jack assembly screw 1103 changes position vertically and horizontally, forcing the extension assembly 1104 inside of the sealed printer chamber 1100. The jointed extension assembly 1104 allows for the rotational force to act on the platform jack assembly screw 1103 even when the screw 1103 changes position horizontally or vertically. The connection component assembly 1106 contains the interior connection component that drives the platform jack assembly screw 1103, the exterior connection component that connects to an external motor 1108 to turn the interior connection component, and a chamber interface component that connects the exterior of the chamber with the interior. The exterior connection component of the connection component assembly 1106 connects to the exterior of the printer chamber setup 1100 through magnets, or an internal and/or external shaft. In the magnetically-driven embodiment the chamber interface component may comprise a rigid plastic material, seals, and bearings to prevent wear along the interface between the exterior and interior of the chamber. In the internal and/or external shaft embodiment an external shaft may be inserted into the interior connection component through the chamber interface component, which may consist of a rigid plastic material, seals, and bearings to prevent wear along the interface between the exterior and interior of the chamber. An external motor 1108 contains an external magnetic assembly (not shown) or an external shaft that is inserted into the connection component assembly 1106 to drive the platform jack assembly screw 1103 to change the position of the printing platform 1110. The printing platform 1110 may support a horizontal actuator 1112, a second horizontal actuator 1114 orthogonal to horizontal actuator 1112 and a moving printing tray 1116. The horizontal actuator 1112 may be utilized to position the printing tray 1116 along the x-axis and the second horizontal actuator 1114 may be utilized to position the printing tray 1116 along the z-axis. The three-axis gantry positioning system is utilized for printing with a fixed printing head 1118 within the sterile printer chamber setup 1100. The actuators may be driven by hydraulic, pneumatic, electric, or magnetically controlled methods (not shown). Various embodiments of the platform jack positioning may be utilized to control different axis positioning of the printer assembly.

FIG. 18G is a side view of a printer chamber setup 1120 containing a hybrid three-axis gantry positioning system utilizing at least one vertical platform jack assembly 1122 to adjust the height of a printing platform 1136. In this embodiment the platform jack assembly 1122 contains a standard platform jack assembly with a platform jack assembly screw 1123 that moves in both vertical and horizontal directions during the rotation of the screw, which changes the height of the jack scissoring and of the printing platform 1136. The platform jack assembly screw 1123 is connected to a connection component on the interior of the printer chamber setup 1120 via an extension assembly 1124, which may be a scissoring assembly, a suspension cylinder assembly, a hydraulic/pneumatic cylinder, or a spring assembly. As the platform jack assembly 1122 is raised or lowered, the platform jack assembly screw 1123 changes position horizontally, forcing the extension assembly 1124 inside of the sealed printer chamber 1100. The platform jack assembly screw 1123 additionally changes position vertically, causing the vertical movement of connection component assembly. The connection component assembly 1126 in this embodiment utilizes a separate exterior platform jack 1132 with a platform jack assembly screw in a fixed vertical position (known as a low-profile or offset platform jack) where an external motor 1130 is raised with the external platform jack 1132 to match the height of the internal platform jack 1122. The external platform jack 1132 itself contains its own platform jack motor 1134 for adjusting the height of the external motor 1130. The height adjustment from both external motors 1130 and 1134 may be computer-controlled to keep the internal platform jack 1122 and the external platform jack 1132 properly aligned. Alternatively or additionally a detection system such as a camera detection system with a target may be utilized to keep the assembly properly aligned. The exterior connection component 1128 of the connection component assembly connects to the exterior of the printer chamber setup 1120 through magnets, or an internal and/or external shaft. In the magnetically-driven embodiment the chamber interface component 1126 may comprise a rigid plastic material, seals, and bearings to prevent wear along the interface between the exterior and interior of the chamber. In the internal and/or external shaft embodiment an external shaft may be inserted into the interior connection component through the chamber interface component 1126, which may comprise a rigid plastic material, seals, and bearings to prevent wear along the interface between the exterior and interior of the chamber. The external motor 1130 contains an external magnetic assembly (not shown) or an external shaft that is inserted into the connection component assembly to drive the platform jack assembly screw 1123 to change the position of the printing platform 1136. The printing platform 1136 may support a horizontal actuator 1138, a second horizontal actuator 1140 orthogonal to horizontal actuator 1138 and a moving printing tray 1142. The horizontal actuator 1138 may be utilized to position the printing tray 1142 along the x-axis and the second horizontal actuator 1140 may be utilized to position the printing tray 1142 along the z-axis. The three-axis gantry positioning system is utilized for printing with a fixed printing head 1144 within the sterile printer chamber setup 1120. The actuators may be driven by hydraulic, pneumatic, electric, or magnetically controlled methods (not shown). Various embodiments of the platform jack positioning may be utilized to control different axis positioning of the printer assembly.

FIG. 18H is a side view of a printer chamber setup 1150 containing a hybrid three-axis gantry positioning system utilizing at least one vertical linear actuator 1152 to adjust the height of a printing platform 1154. The printing platform 1154 may support a printing tray 1156 which may move along a series of tracks for positioning. In this embodiment a plurality of soft robotic actuators 1158 and 1160, which cause the soft robotics material to curl when pressurized with hydraulic or pneumatic fluid pressure, are utilized to precisely move the printing tray 1156 in relation to the fixed printing head 1164. The soft robotic actuators 1158 and 1160 may be positioned to push and pull the printing tray 1156 along a series of tracks (not shown) on the printing platform 1154 in the two horizontal positions. In this embodiment the soft robotic actuator 1158 is in a resting position, while the soft robotic actuator 1160 is in the deployed position when fluid pressure enters into the fluid assembly 1162. The use of soft robotic actuators is advantageous in that there are no rigid materials if a non-rigid chamber is utilized, they are not made from complex components, and they are readily sterilizable. The three-axis gantry positioning system is utilized for printing with a fixed printing head 1164 within the sterile printer chamber setup 1150. The linear actuators may be driven by hydraulic, pneumatic, electric, or magnetically controlled methods (not shown). In alternate embodiments a plurality of soft robotic actuators and linear actuators may be utilized.

FIG. 18I is a side view of a printer chamber setup 1170 containing a hybrid multiaxis positioning system utilizing at least one vertical linear actuator 1172 to adjust the height of a printing platform 1174. The printing platform 1174 may support a printing tray 1176, which may be in a fixed position or move along a series of tracks for positioning. In this embodiment a plurality of soft robotic actuators 1178 and 1180, which cause the soft robotic material to curl when pressurized with hydraulic or pneumatic fluid pressure, are utilized to precisely move a plurality of printing heads 1184 with a fixed position at the top of the chamber into position above the printing tray 1176 for dispensing material. The plurality of soft robotic actuators 1178 and 1180 may be positioned in a plurality of directions above the printing tray 1176 for precisely dispensing material. In this embodiment the soft robotic actuator 1178 is in an actuated position and moves a printing head into a precise position above the printing tray 1176. The soft robotic actuator 1180 is in an actuated position and moves a different printing head into another precise position above the printing tray 1176. The soft robotic actuators 1178 and 1180 are in the deployed position when fluid pressure enters into the fluid assembly 1182. The linear actuators may be driven by hydraulic, pneumatic, electric, or magnetically controlled methods (not shown). In alternate embodiments a plurality of soft robotic actuators, printing heads, and linear actuators may be utilized.

FIG. 18J is a side view of a printer chamber setup 1190 containing a hybrid multiaxis positioning system utilizing at least two vertical soft robotic actuators 1194 and 1196 to adjust the height of a printing platform 1192. The printing platform 1192 may support a horizontal soft robotic bellows actuator 1202, a second horizontal soft robotic bellows actuator (not shown) and a moving printing tray 1204. In this embodiment a plurality of soft robotic actuators 1194 and 1196, which cause the soft robotic material to curl when pressurized with hydraulic or pneumatic fluid pressure, are utilized to precisely move the printing platform 1192 in a vertical direction. In this embodiment the soft robotic actuators 1194 and 1196 are in an actuated position and move the printing platform 1192 into a precise position below the fixed printing head 1206. The soft robotic actuators 1194 and 1196 are in the deployed position when fluid pressure enters into the fluid assemblies 1198 and 1200, respectively. The horizontal soft robotic bellows actuator 1202 is a soft robotic linear actuator that expands the bellows when actuated under fluid pressure. The soft robotic bellows actuator 1202 may be utilized to position the printing tray 1204 along the x-axis. An additional horizontal linear actuator (not shown) may be utilized to position the printing tray 1204 along the z-axis. Alternatively the soft robotic actuators controlling the movement of the printing platform 1192 along the y-axis may additionally be utilized to position the printing platform 1192 along an additional axis such as the x-axis or z-axis. The soft robotic actuators may be driven by hydraulic and/or pneumatic fluid pressure.

FIG. 18K is a side view of a printer chamber setup 1210 containing a hybrid multiaxis positioning system utilizing a fixed printing platform 1212 and a tethered multiaxis printing device 1216. In this embodiment the tethered multiaxis printing device 1216 comprises a plurality of soft robotic appendages 1218, which are attached to a core of the device that contains the printing head dispenser 1220 and the printing head assembly 1222. The printing head assembly 1222 is tethered to the top of the printer chamber setup 1210 through a port connection 1226 that is utilized to feed material to the tethered multiaxis printing device 1216. The printing platform 1212 may support a printing tray 1214, which may be in a fixed position or move along a series of tracks for positioning. The tethered multiaxis printing device 1216 utilizes a plurality of soft robotic appendages 1218, where the soft robotic material curls when pressurized with hydraulic or pneumatic fluid pressure, to precisely position the printing head dispenser 1220 above the printing tray 1214. The plurality of soft robotic appendages 1218 may also be utilized to push and pull the printing tray 1214 along a series of tracks (not shown) on the printing platform 1212 in the two horizontal directions. In this embodiment a plurality of soft robotic appendages 1218 moves when fluid pressure enters into the fluid assemblies 1224. The soft robotic appendages may be driven by hydraulic and/or pneumatic fluid pressure.

FIG. 18L is a side view of a printer chamber setup 1230 containing a multiaxis positioning system utilizing a fixed printing platform 1232 and an untethered multiaxis printing device 1236. In this embodiment the untethered multiaxis printing device 1236 comprises a plurality of soft, rigid, and/or rigid coated with soft material robotic appendages 1238, which are attached to a core of the device that contains the printing head dispenser 1240 and the printing head assembly 1242, which contains a storage reservoir to hold the materials to dispense. A plurality of storage reservoirs may be utilized for dispensing solid, liquid, gas or mixed materials, where compressed gas or air may be used to drive and regulate the dispensing of solid or liquid materials including cells in a liquid suspension. The printing head assembly 1242 may contain a heater for heating the material prior to dispensing. The printing platform 1232 may support a printing tray 1234, which may be in a fixed position or move along a series of tracks for positioning. The untethered multiaxis printing device 1236 utilizes a plurality of robotic appendages 1238, where the appendages move in response to the movement of the drive mechanism, which may be driven by hydraulic, pneumatic, electric, or magnetically controlled methods (not shown). The drive mechanism may contain its own reservoir within the untethered multiaxis printing device 1236, including a reservoir for hydraulic and/or pneumatic fluid pressure, an internal pump for generating such pressure, a battery pack, a plurality of magnets or other elements. The battery may be charged by inductive charging, directed charging through microwave, laser, or other line-of-sight radiation, solar cell or other wireless charging methods. The untethered multiaxis printing device 1236 may additionally move to a location inside the interior of the printer chamber setup 1230, where it can refill the internal reservoirs for solid, liquid, gas, or mixed inputs as well as recharge an internal reservoir for the drive mechanism, including charging a pressurized hydraulic and/or pneumatic reservoir, a battery through direct charging with energized contacts, inductive charging, or other mechanical energy storage mechanism (winding). The untethered multiaxis printing device 1236 plurality of robotic appendages 1238 may be utilized to position the at least one printing head dispenser 1240 above the printing tray 1234. The untethered multiaxis printing device 1236 may contain a plurality of printing heads, each of which has a different function and dispenses material from a plurality of corresponding internal reservoirs. The plurality of robotic appendages 1238 may also be utilized to push and pull the printing tray 1234 along a series of tracks (not shown) on the printing platform 1232 in the two horizontal directions. The untethered multiaxis printing device 1236 has the advantage of being completely internal to the printer chamber setup 1230 without any external connections or tethering. Additionally the setup is advantageous as the untethered multiaxis printing device 1236 can provide multiaxis printing for a plurality of printing trays by moving to each one independently.

FIG. 18M is a side view of a printer chamber setup 1250 containing a plurality of multiaxis positioning devices 1256, 1258, 1260, and 1262 utilizing a fixed printing platform 1252 and a printing tray 1254. In this embodiment the plurality of untethered multiaxis printing devices 1256, 1258, 1260, and 1262 operate as described in View 'L' with the exception of the potential to be individualized and capable of performing different functions. A plurality of storage reservoirs (not shown) within the plurality of multiaxis positioning devices 1256, 1258, 1260, and 1262 may be utilized for dispensing solid, liquid, gas or mixed materials, where compressed gas or air may be used to drive and regulate the dispensing of solid or liquid materials including cells in a liquid suspension. In this embodiment a single untethered multiaxis printing device 1256, 1258, 1260, or 1262 may contain a single reservoir and a single material to dispense out of the printing head dispenser. The material dispensed from each untethered multiaxis printing device 1256, 1258, 1260, or 1262 may be different for each device. The printing platform 1252 may support the printing tray 1254, which may be in a fixed position or move along a series of tracks for positioning. In this embodiment the untethered multiaxis printing device 1262 contains robotic appendages with magnetic, conductive, or ferrous material at the base that comes in contact with the surface for locomotion. Magnetic plates 1264, ferrous material, and/or magnetic fields may be placed directly external to the printer chamber setup 1250, where the multiaxis positioning devices 1256, 1258, 1260, and 1262 may utilize the full surface area of the interior of the chamber for locomotion, positioning, charging, refilling reservoirs, or other operational functions. The untethered multiaxis printing devices 1256, 1258, 1260, and 1262 may be sterilized within the printer chamber setup 1250 as a complete assembly or may be sterilized using an alternate process (such as chemical sterilization) and aseptically inserted into the interior of the printer chamber setup 1250. The untethered multiaxis printing devices 1256, 1258, 1260, and 1262 have the advantage of being simpler and dedicated to the material inputs that they hold, they can be redundant in case of operating failure inside of sterile chamber, they can self-position and print (dispense materials) over a plurality of printing trays, and they can be replaceable in that additional devices may be aseptically inserted into the interior of the printer chamber setup 1250.

FIGS. 19A-19F show an alternate embodiment of the connections steps to insert the printing head into the sterile three-dimensional assembly body.

FIG. 19A is a side view of an embodiment that shows a sterilized three-dimensional printer assembly body 2000, with a rigid or flexible wall, containing a printing head insertion assembly 2002. The portion of the printing head insertion assembly 2002 internal to three-dimensional printer assembly body 2000 contains an interface assembly 2006 in the closed position and an internal dip tube 2004. The external portion of the printing head insertion assembly 2002 contains a removable cap 2012, a fluid inlet port 2008, and a fluid outlet port 2010.

FIG. 19B is a side view of the removable cap 2012' being removed from the printing head insertion assembly 2002 and the electronically-controlled printing head 2014 being inserted into the assembly.

FIG. 19C is a side view of the electronically-controlled printing head 2014 inserted into the printing head insertion assembly 2002 and twisted into place 2016 in a first position.

FIG. 19D is a side view of the printing head insertion assembly 2002 with a tubing piece 2018 inserted into the fluid inlet port 2008, wherein a chemical sterilant or sanitizer 2020 fills the printing head insertion assembly 2002 and the interface assembly 2006, thereby sterilizing the internal section of the electronically-controlled printing head 2014. The chemical sterilant or sanitizer 2020 can comprise a liquid like 30% hydrogen peroxide, or may comprise a gas sterilant such as vaporized hydrogen peroxide or ethylene oxide.

FIG. 19E is a side view of the printing head insertion assembly 2002 with a tubing piece 2022 inserted into the fluid outlet port 2010, wherein the chemical sterilant or sanitizer is removed by vacuum pressure after the period of time required to sterilize the printing head 2014 is completed. The internal dip tube 2004 can be utilized to remove a fluid chemical sterilant or sanitizer or condensate from a gas chemical sterilant.

FIG. 19F is a side view of the printing head insertion assembly where the electronically-controlled printing head 2014 is twisted 2024 into a second position, where either the printing head 2014 is screwed down and breaks through the interface assembly 2006' into the interior of the three-dimensional printer assembly body or the interface assembly 2006' opens up via a mechanical mechanism (not shown) in multiple directions (like a flower petal or gates). In this way, the sterilized electronically-controlled printing head 2014 is allowed access to the interior of the three-dimensional printer assembly body 2000. The sterilized electronically-controlled printing head 2014 is ready to print within the three-dimensional printed assembly body 2000.

FIGS. 20A-20E show another embodiment of the connections steps to insert the printing head into the sterile three-dimensional assembly body.

FIG. 20A is a side view of an embodiment that shows a sterilized three-dimensional printer assembly body 2030, with a rigid or flexible wall, containing a printing head insertion assembly 2032. The printing head insertion assembly 2032 may comprise an aseptic connection strip 2034, which may contain a sterilizing grade filter membrane and be held in place within the assembly with a seal, an aseptic connection strip guide 2036 to guide the aseptic connection strip 2034 as it is removed, and excess material 2038 from the aseptic connection strip 2034 for the operator to pull after the connection has taken place. The external portion 2040 of the printing head insertion assembly 2032 contains an aseptic connector with a removal strip 2042, which may additionally contain a sterilizing grade filter and be held in place within the assembly FIG. 20B is a side view of the sterilized three-dimensional printer assembly body 2030 containing a printing head insertion assembly 2032. A sterilized printing head assembly 2044, which itself may be rigid or flexible, contains an aseptic connector 2046, which may additionally contain a sterilizing grade filter and be held in place within the assembly 2044 with a seal, an internal sterilized printing head 2048, and a lever assembly 2050 to pull the internal sterilized printing head 2048 into the three-dimensional printer assembly body 2030. The sterilized printing head 2048 may be single-use or multi-use and capable of being re-sterilized.

FIG. 20C is a side view of the sterilized printing head 2044 where the body is twisted into place locking the at least two aseptic connectors 2040 and 2046 into place. The operator pulls the aseptic connection strips 2042 and 2052, which may contain sterilizing grade filter membranes, in direction 2056. The removal of the two aseptic connection strips 2042 and 2052 opens up the sterilized printing head 2044 into the printing head insertion assembly 2032. The aseptic connection strip 2034, which may contain a sterilizing grade filter membrane, may remain in place if the aseptic connection between aseptic connectors 2040 and 2046 was not properly connected or the sterilized printing head 2044 integrity was compromised. The integrity of this assembly may be integrity tested with an integrity testing device (not shown) through a vented connection with a sterilizing grade filter (not shown) prior to proceeding with the next steps of removing the aseptic seal within the sterilized three-dimensional printer assembly body 2030.

FIG. 20D is a side view of the sterilized printing head assembly 2044 where the lever assembly 2050 is depressed and pulls the internal sterilized printing head 2048 into the printing head insertion assembly 2032. The printer material feed tubing assembly 2058, which brings material inputs (such as fluids with biologically active products or structural material) to the sterilized printing head 2048, may be coiled or stored within the sterilized printing head assembly 2044 and sterilized along with the assembly 2044. A port 2060 in the sterilized printing head assembly 2044 serves as an interface between the feed tubing in the interior and exterior of the setup. Alternatively the tubing line to bring the input material to the sterilized printing head 2048 may be aseptically connected to the sterile assembly. The operator pulls the excess material 2038 from the aseptic connection strip 2034 away from the printing head insertion assembly 2032. The aseptic connection strip 2034, which may contain a sterilizing grade filter membrane, is pulled through the aseptic connection strip guide 2036.

FIG. 20E is a side view of the printing head insertion assembly 2032 where the removal of this aseptic connection strip 2034 opens up the sterilized printing head 2048 to the internal sterilized chamber of the three-dimensional printer assembly body 2030. The sterilized printing head 2048 may now print to the internal printing tray within the unit, where additional inputs are brought through internal tubing 2058.

FIGS. 21A-21E shows an alternate embodiment of the connections steps to insert a sterilized printing head with a bellows assembly into the sterile three-dimensional assembly body.

FIG. 21A is a side view of an embodiment that shows a sterilized three-dimensional printer assembly body 2068, with a rigid or flexible wall, containing a printing head insertion assembly 2070 comprising an aseptic connection strip 2072 held in place within the assembly with a seal, an aseptic connection strip guide 2074 to guide the aseptic connection strip 2072 as it is removed, and excess material 2076 from the aseptic connection strip 2072 for the operator to pull after the connection has taken place. A sterilized printing head assembly with a bellows assembly 2078, which itself may be rigid or flexible, contains an aseptic connector, which may additionally contain a sterilizing grade filter and be held in place within the assembly with a seal, and an internal sterilized printing head 2082. The sterilized printing head assembly with a bellows assembly 2078 uses the bellows assembly to push the sterilized printing head 2082 into the printing head insertion assembly 2070 within the three-dimensional printer assembly body 2068. The sterilized printing head 2082 may be single-use or multi-use and capable of being re-sterilized.

FIG. 21B is a side view of the sterilized printing head assembly with a bellows assembly 2078 where the body is twisted 2084 into place locking the at least two aseptic connectors into place. The operator pulls the aseptic connection strips 2086 and 2088, which may contain sterilizing grade filter membranes, in direction 2090. The removal of the two aseptic connection strips 2086 and 2088 opens up the sterilized printing head assembly with a bellows assembly 2078 into the printing head insertion assembly 2070. The aseptic connection strip 2072, which may contain a sterilizing grade filter membrane, may remain in place if the aseptic connection between aseptic connectors was not properly connected or the sterilized printing head 2082 integrity was compromised. The integrity of this assembly may be integrity tested with an integrity testing device (not shown) through a vented connection with a sterilizing grade filter (not shown) prior to proceeding with the next steps of removing the aseptic seal within the sterilized three-dimensional printer assembly body 2068.

FIG. 21C is a side view of the sterilized printing head assembly with a bellows assembly 2078 where the operator pushes on the sterilized printing head assembly with a bellows assembly 2078 in direction 2092 compressing the bellows assembly and pushing the sterilized printing head 2082 into the printing head insertion assembly 2070.

FIG. 21D is a side view of the sterilized printing head assembly with a bellows assembly 2078 where the assembly is twisted in direction 2094 and locked into place. The operator pulls in direction 2096 the excess material 2076 from the aseptic connection strip 2072 away from the printing head insertion assembly 2070. The aseptic connection strip 2072 is pulled through the aseptic connection strip guide 2074.

FIG. 21E is a side view of the printing head insertion assembly 2070 where the removal of this aseptic connection strip 2072 opens up the sterilized printing head 2082 to the internal sterilized chamber of the three-dimensional printer assembly body 2068. The sterilized printing head 2082 may now print to the internal printing tray.

Figure 22:
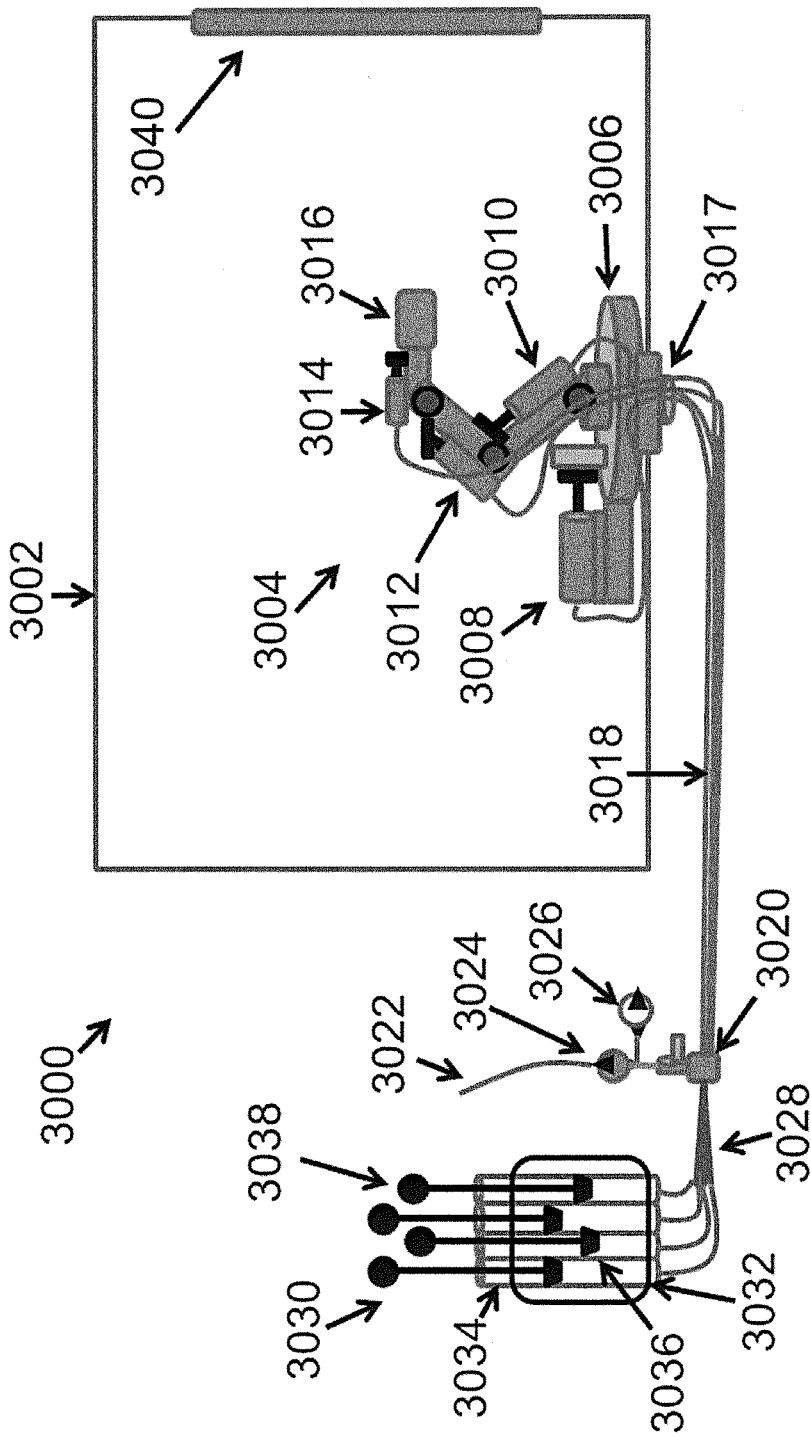
FIG. 22 illustrates an embodiment of a manually-controlled robotic arm within a sterilized three-dimensional assembly chamber.

FIG. 22 shows an embodiment of a manually-controlled robotic arm within a sterilized three-dimensional assembly chamber. The chamber and robotic arm control assembly 3000 comprises a sterilized chamber 3002 that contains at least one robotic arm assembly 3004, a port 3017 to connect a control assembly 3030 with the robotic arm assembly 3004, and a transfer hatch 3040 for the chamber 3002. In this embodiment the robotic arm assembly 3004 utilizes a plurality of actuators to control the positioning and movements of the assembly. The robotic arm assembly 3004, including the plurality of actuators, may be made out of sterilizable (gamma irradiatable and/or autoclavable) plastic materials and rubberized seals. In this embodiment the robotic arm assembly 3004 may be controlled by utilizing an actuator 3008 to rotate a rotating base 3006. An additional actuator 3010 pushes on a support connected to an articulating joint moving the position of the arm. An additional actuator 3012 pushes on a support connected to an articulating joint moving the position of the robotic grippers 3016. An additional actuator 3014 pushes on a support connected to an articulating joint that opens and closes the robotic grippers 3016. The actuators may be driven by hydraulic, pneumatic, electric, or magnetically controlled methods (not shown). In this embodiment the robotic arm control assembly 3030 is a manual controller external to the sterilized chamber 3002 and utilizes hydraulic and/or pneumatic fluid pressure to control the movements of the robotic arm assembly 3004 internal to the sterilized chamber 3002. The manual robotic arm control assembly 3030 utilizes a plurality of hydraulic and/or pneumatic tubing lines 3018 to move fluid through the port 3017 into the actuators located on the robotic arm assembly 3004 to control the movements. The tubing lines 3018 are charged with sterile hydraulic and/or pneumatic fluid pressure through the filling assembly 3020. In this embodiment the tubing lines are filled with a hydraulic fluid, which is for example sterile filtered water. The sterile filtered water enters into the chamber and robotic arm control assembly 3000 after sterilization and is setup for use by an operator. Purified water enters through the tubing line 3022 and passes through a sterilizing grade filter 3024 into the filling assembly 3020, which may serve as a manifold to completely fill each of the individual tubing lines 3018. The tubing lines 3018 may be cleared of air through a sterilizing grade vent filter 3026, which allows the displaced air to vent to the atmosphere as it is displaced by sterile filtered water entering into the assembly. Additional sterile filtered water, other fluids, or, in other embodiments, pneumatic air or gas pressure may be added to the tubing lines 3018 via the filling assembly 3020 in case of leakage or loss of pressure. In this basic embodiment a manual robotic arm control assembly 3030 is utilized to control the movements of the robotic arm assembly 3004. A plurality of hydraulic and/or pneumatic pistons 3034 are arranged in a piston assembly 3032 that comprises cylinders filled with fluid, and the piston heads 3038 are pushed and/or pulled by the operator. The movement of one of the piston heads 3038 affects the movement of a seal 3036 internal to the piston and causes the displacement of the internal fluid through the tubing lines 3028 and 3018, resulting in the movement of the robotic arm assembly 3004. The purpose of the robotic arm assembly 3004 is to manipulate and move objects internal to the sterilized chamber 3002. This has the benefits of moving, storing, stacking or manipulating the objects inside of the sterilized chamber 3002 in ways not possible before. The transfer hatch 3040 may be utilized to remove objects aseptically from the sterilized chamber 3002 and/or to connect to additional sterilized chambers to form a more complex assembly. The robotic arm assembly 3004 may be utilized to move materials from one sterilized chamber to another through the connected transfer hatches 3040.

Figure 23:
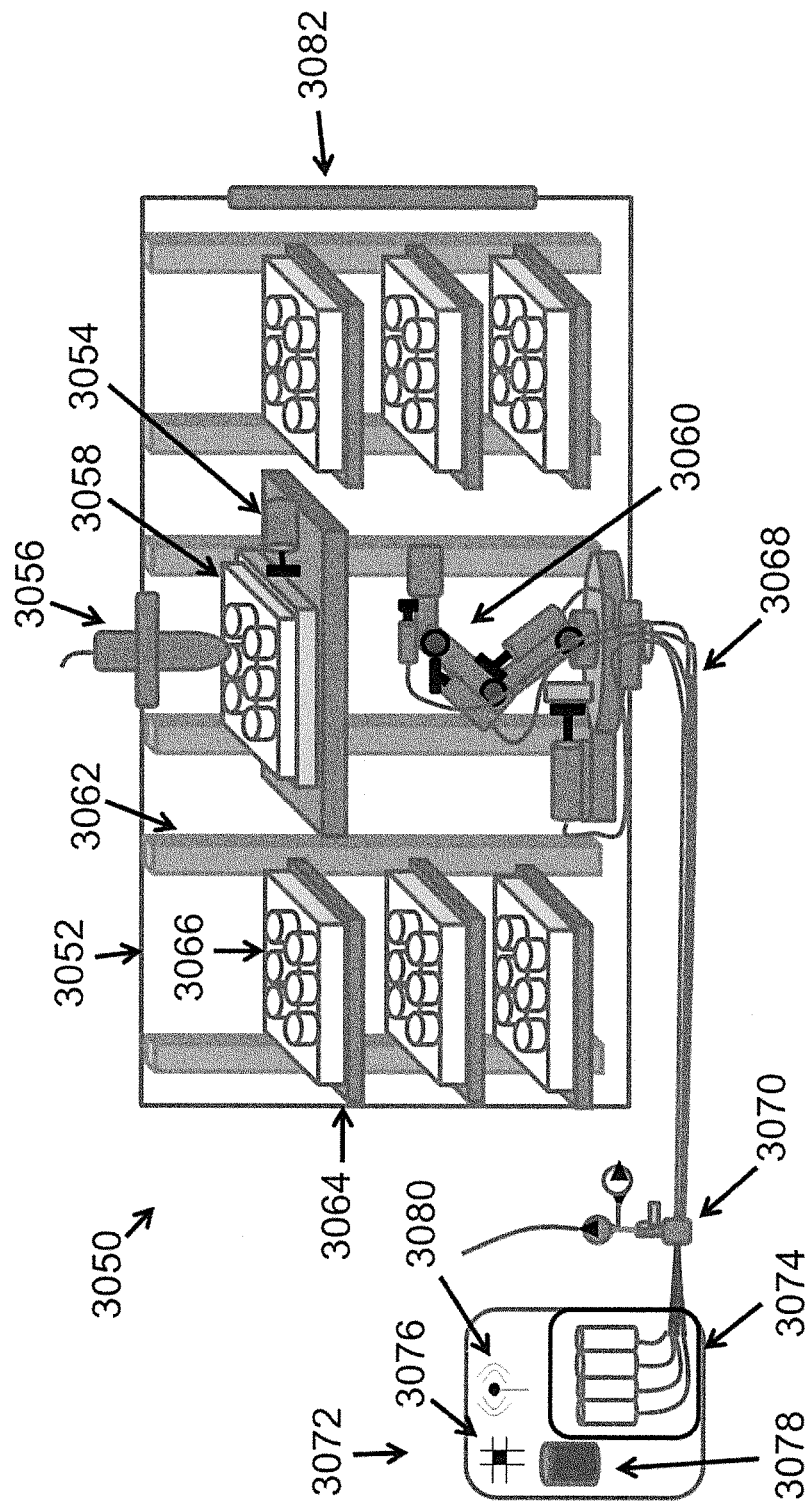
FIG. 23 illustrates an embodiment of an automatically-controlled robotic arm within a sterilized three-dimensional printing chamber.

FIG. 23 shows an embodiment of an automatically controlled robotic arm within a sterilized three-dimensional printing chamber. The three-dimensional printing chamber and robotic arm control assembly 3050 comprises a sterilized chamber 3052 that contains at least one robotic arm assembly 3060, a plurality of tubing that connects an automated control assembly 3072 with the robotic arm assembly 3060, and a transfer hatch 3082 for the chamber. In this embodiment the sterilized chamber 3052 contains a printing assembly with a three-axis positioning gantry assembly 3054 and a printing head 3056 for dispensing material to a printing tray, which in this embodiment contains a multi-well plate 3058. The sterilized chamber 3052 additionally contains a plurality of movable shelves 3064 attached to the walls of the sterilized chamber 3052 with supports 3062 for stacking a plurality of materials and/or printing trays, which in this embodiment contain a plurality of multi-well plates 3066. In this embodiment the robotic arm assembly 3060 is utilized to move the empty multi-well plates 3058 to the printer assembly for printing with structural and biologically-active materials and to move those plates to the movable shelves 3064 for storage, incubation, and/or analysis. The automated control assembly 3072 utilizes a plurality of hydraulic and/or pneumatic tubing 3068 to move pressurized fluid into the actuators located on the robotic arm assembly 3060 to control the movements. The tubing lines are charged with sterile hydraulic and/or pneumatic fluid pressure through the filling assembly 3070. In this embodiment an automated control assembly 3072 is utilized to control the movements of the robotic arm assembly 3060. Pluralities of hydraulic and/or pneumatic pistons are arranged in a piston assembly 3074 that comprises pistons filled with fluid and the movements of the piston heads (not shown) are automatically controlled with a processing device 3076. A memory storage device 3078 may store programs local to the automated control assembly 3072 to control the movements of the robotic arm within a program. The processing device 3076 may also process sensor data and alter the movements of the robotic arm assembly 3060 based on the programs stored within the memory storage device 3078. The automated control assembly 3072 may additionally contain a wireless communication device to import robotic arm assembly control protocols, wireless sensor data, and/or communicate with an external network and/or a mobile device. The transfer hatch 3082 may be utilized to remove objects aseptically from the sterilized chamber 3052 and/or to connect to additional sterilized chambers to form a more complex assembly. The robotic arm assembly 3060 may be utilized to move materials from one sterilized chamber to another through the connected transfer hatches 3082.

Figure 24:
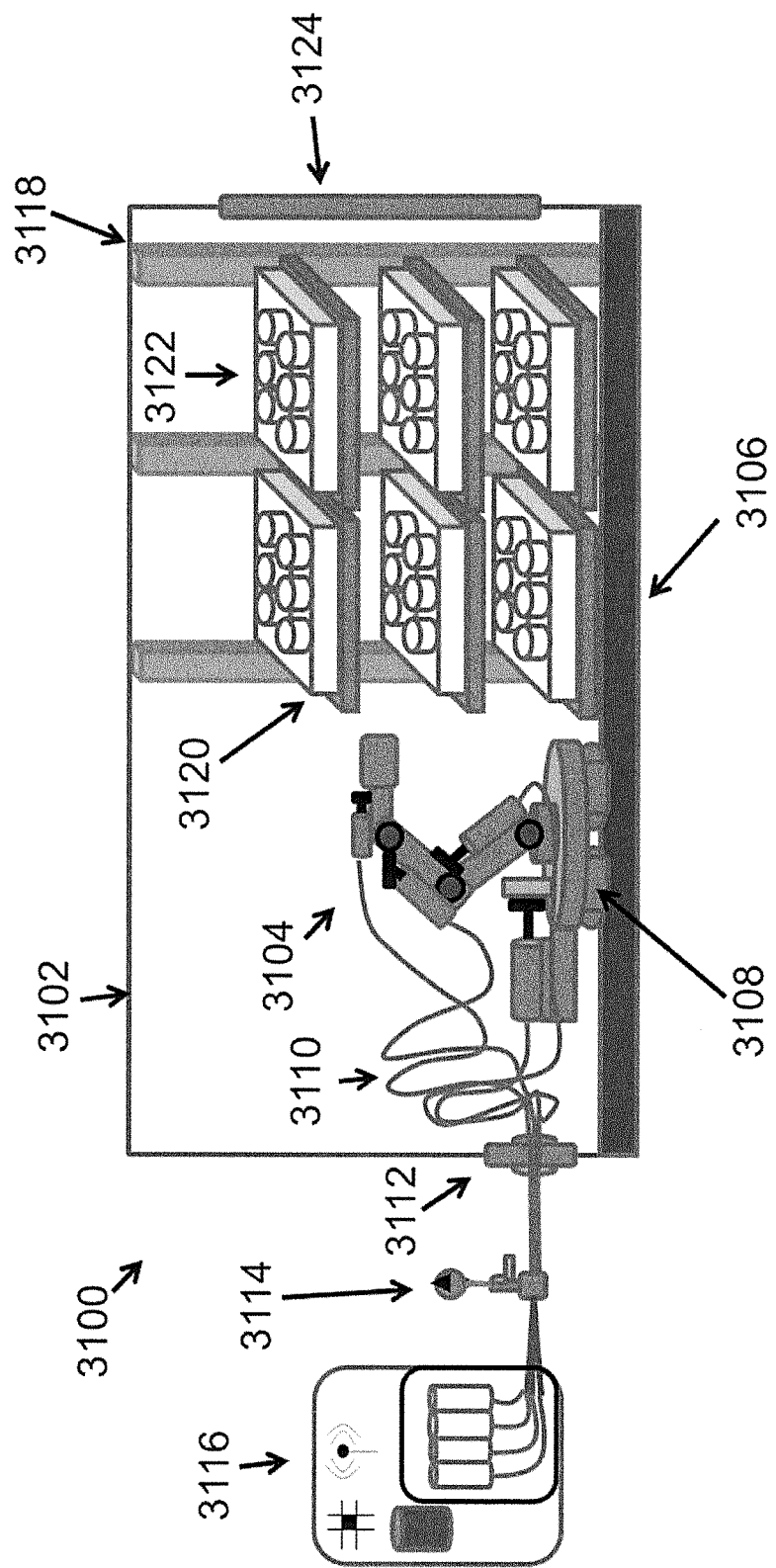
FIG. 24 illustrates an embodiment of an automatically-controlled robotic arm on a movable track within a sterilized three-dimensional assembly chamber.

FIG. 24 shows an embodiment of an automatically controlled robotic arm on a movable track within a sterilized three-dimensional assembly chamber. The three-dimensional chamber and robotic arm control assembly 3100 comprises a sterilized chamber 3102 that contains at least one robotic arm assembly 3104, a plurality of tubing 3110 that connects an automated control assembly 3116 with the robotic arm assembly 3104, and a transfer hatch 3124 for the chamber. In this embodiment the sterilized chamber 3102 contains a plurality of movable shelves 3120 attached to the walls of the sterilized chamber 3102 with supports 3118 for stacking a plurality of materials and/or printing trays, which in this embodiment contain a plurality of multi-well plates 3122. In this embodiment the robotic arm assembly 3104 is utilized to move the stack multi-well plates 3122 on the movable shelves 3120 for storage, incubation, and/or analysis. For additional range of movement the robotic arm assembly 3104 may move along a track 3106 utilizing a wheeled or track assembly 3108. The wheeled or track assembly 3108 may be powered by a hydraulic motor, a pneumatic motor, an electric motor, and/or a magnetic motor. The automated control assembly 3116 utilizes a plurality of hydraulic and/or pneumatic tubing to move pressurized fluid into the actuators located on the robotic arm assembly 3104 to control the movements. The tubing lines are charged with sterile hydraulic and/or pneumatic fluid pressure through the filling assembly 3114. The transfer hatch 3124 may be utilized to remove objects aseptically from the sterilized chamber 3102 and/or to connect to additional sterilized chambers to form a more complex assembly. The robotic arm assembly 3104 may be utilized to move materials from one sterilized chamber to another through the connected transfer hatches 3124.

Figure 25:
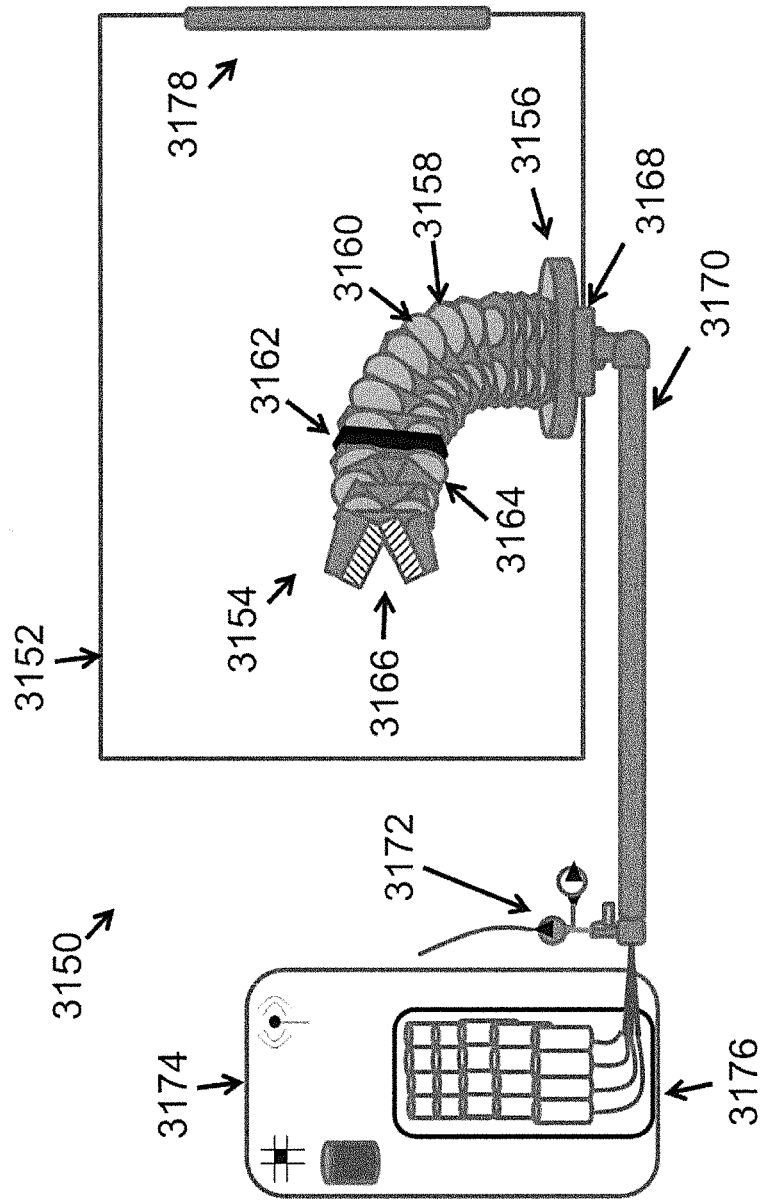
FIG. 25 illustrates an embodiment of an automatically-controlled soft robotic arm within a sterilized three-dimensional assembly chamber.

FIG. 25 shows an embodiment of an automatically controlled soft robotic arm within a sterilized three-dimensional assembly chamber. The three-dimensional chamber and soft robotic arm control assembly 3150 comprises a sterilized chamber 3152 that contains at least one soft robotic arm assembly 3154, a plurality of tubing 3170 that connects an automated control assembly 3174 with the soft robotic arm assembly 3154, and a transfer hatch 3178 for the chamber. In this embodiment the soft robotic arm assembly 3154 contains a base plate 3156 and a plurality of plates 3158 containing at least two inflatable sections, such as bags, bladders, or expandable reservoirs positioned accordingly within the plate assembly. As the inflatable sections in the plurality of plates 3158 are unevenly inflated 3160, the soft robotic arm assembly 3154 bends towards a specific direction. The more inflatable sections available within the plurality of plates 3158, the greater the degree of control for positioning the soft robotic arm assembly 3154. The soft robotic arm assembly 3154 may contain a collar 3162 that separates the positioning section of the soft robotic arm from the gripping section 3166 of the robotic arm. The geometry of the plurality of plates 3164 in the gripping section 3166 may have a hinge in the center, where the inflatable sections cause the gripping section 3166 to close around an object. The automated control assembly 3174 utilizes a plurality of hydraulic and/or pneumatic tubing to move pressurized fluid into the actuators located on the soft robotic arm assembly 3154 to control the movements. The tubing lines are charged with sterile hydraulic and/or pneumatic fluid pressure through the filling assembly 3172. The transfer hatch 3178 may be utilized to remove objects aseptically from the sterilized chamber 3152 and/or to connect to additional sterilized chambers to form a more complex assembly. The robotic arm assembly 3154 may be utilized to move materials from one sterilized chamber to another through the connected transfer hatches 3178.

Figure 26:
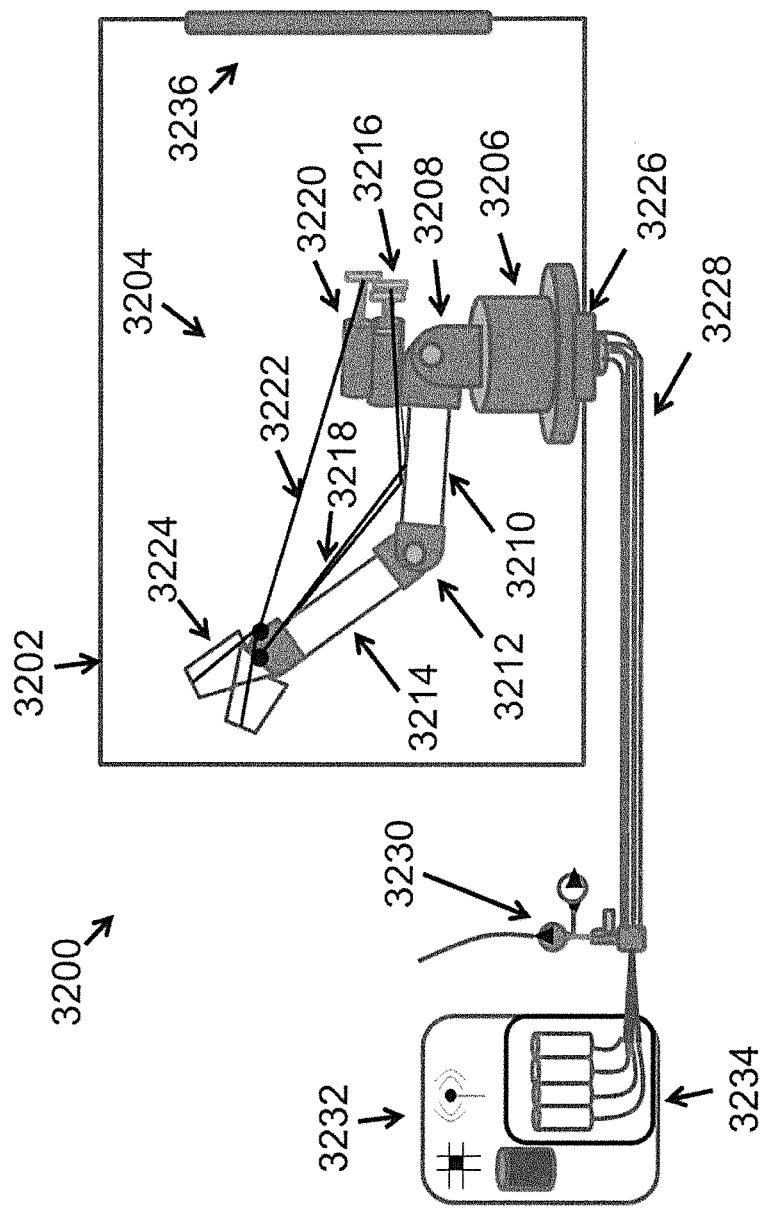
FIG. 26 illustrates an embodiment of an automatically-controlled inflatable robotic arm within a sterilized three-dimensional assembly chamber.

FIG. 26 shows an embodiment of an automatically-controlled inflatable robotic arm within a sterilized three-dimensional assembly chamber. The three-dimensional chamber and inflatable robotic arm control assembly 3200 comprises a sterilized chamber 3202 that contains at least one inflatable robotic arm assembly 3204, a plurality of tubing 3228 that connects an automated control assembly 3232 with the inflatable robotic arm assembly 3204, and a transfer hatch 3236 for the chamber. In this embodiment the inflatable robotic arm assembly 3204 contains a rotating base plate 3206, a movable hinge joint 3208 that positions the inflatable robotic arm assembly 3204, a plurality of inflatable sections, which may be bags, bladders, or expandable reservoirs, including a first inflatable section 3210 and a second inflatable section 3214, with a movable hinge section in between the two inflatable sections 3210 and 3214. Additionally and/or alternatively the inflatable assemblies may be articulated along a seam and/or seal between two or more inflatable sections. A plurality of actuators 3216 pull cables 3218, which are connected to the inflatable sections, and position the inflatable robotic arm assembly 3204. An inflatable gripping section 3224 is available at the end of the inflatable arm assembly and closes around an object when pulled on by cable 3222, which is controlled by actuator 3220. The automated control assembly 3232 utilizes a plurality of hydraulic and/or pneumatic tubing 3228 to move pressurized fluid into the actuators located on the soft robotic arm assembly 3204 to control the movements. The tubing lines are charged with sterile hydraulic and/or pneumatic fluid pressure through the filling assembly 3230. Pluralities of hydraulic and/or pneumatic pistons are arranged in a piston assembly 3074 that comprises cylinders filled with fluid and the movements of the piston heads (not shown) are automatically controlled with a processing device. The transfer hatch 3236 may be utilized to remove objects aseptically from the sterilized chamber 3202 and/or to connect to additional sterilized chambers to form a more complex assembly. The robotic arm assembly 3204 may be utilized to move materials from one sterilized chamber to another through the connected transfer hatches 3236.

FIGS. 27A-27E show multiple embodiments of a sampling system which may provide periodic and/or continuous sampling of the materials located in the printing tray.

FIG. 27A is a side view of a single-use printer chamber 4000 with a single-use aseptic sampling connector 4008. The single-use printer chamber 4000 contains a printing tray 4002, which in this embodiment is a multi-well tray. Each of the multi-well printing tray 4002 wells contains an opening, a seal, septum, and/or a closing assembly (not shown) that can allow material, particularly fluid-based materials, into a sampling tubing assembly 4004 below the printing tray 4002. The sample tubing assembly 4004 may be aseptically connected to at least one external sanitary connection assembly 4006. The sample tubing assembly 4004 may be expertly arranged to provide at least one sampling port for each well of the multi-well plate printing tray 4002, may provide multiple sampling ports for each well, and/or may provide sampling ports to at least one representative well. The external sanitary connection assembly 4006 aseptically connects to an aseptic sampling connector 4008, which in this embodiment is a TakeONE® aseptic sampling assembly. The operator may manually depress at least one of the spring-loaded thumb press actuators 4010 to push a needle through a self-sealing platinum-cured silicone septa (not shown), which provides a channel for the fluid material to pass through the single-use aseptic sampling connector 4008 and into a sampling collection container 4012, which may be a bag, bottle, centrifuge tube, or other sterile container/connector type. The operator aseptically removes the sampling collection container 4012 utilizing a Quickseal® cutting tool (not shown) on the Quickseal® collar 4014. The operator may use the sample from the sampling collection container 4012 originating from the single-use printer chamber 4000 printing tray 4002 in at least one external measurement device (not shown), to make a determination about the state of the material inside of the printing tray 4002. Measurement results from the at least one external measurement device (not shown) may be manually entered and/or automatically (via a wired and/or wireless connection) communicated to the single-use printer chamber 4000 controller (not shown).

FIG. 27B is a side view of a single-use printer chamber 4030 with an external continuous sampling system 4040. The single-use printer chamber 4030 contains a printing tray 4032, which in this embodiment is a multi-well tray. Each of the multi-well printing tray 4032 wells contains an opening, a seal, septum, and/or a closing assembly (not shown) that can allow material, particularly fluid based materials, into a sampling tubing assembly 4034 below the printing tray 4032. The sample tubing assembly 4034 may be aseptically connected to at least one external sanitary connection assembly 4036. The sample tubing assembly 4034 may be expertly arranged to provide at least one sampling port for each well of the multi-well plate printing tray 4002, may provide multiple sampling ports for each well, and/or may provide sampling ports to at least one representative well. The external sanitary connection assembly 4036 aseptically connects to a tubing assembly 4038, which provides the fluid material to at least one external continuous sampling system 4040, which in this embodiment is a BioPAT® Trace analysis system. The external continuous sampling system 4040 may be a manual system, where an operator determines when a sample should be manually taken, or may be an automated system, where samples are taken at predetermined time intervals, by performing continuous sampling, and or by performing sampling based on intervals determined by the measurement data results. The fluid material tested by the external continuous sampling system 4040 may be read by single-use sensors and the fluid material may be discarded after testing through tubing line 4042, which may allow the fluid material to exit the system via a drain (not shown) or by filling a carboy or container (not shown) for discarding after the run has completed. Additionally and/or alternatively the fluid material may be aseptically returned to the printing tray 4032 after testing. Measurement results from the at least one external continuous sampling system 4040 may be manually entered and/or automatically (via a wired and/or wireless connection) communicated to the single-use printer chamber 4030 controller (not shown).

FIG. 27C is a side view of a single-use printer chamber 4050 with an internal sampling system. The single-use printer chamber 4050 contains a printing tray 4052, which in this embodiment is a multi-well tray. An internal sampling system 4054 to provide measurement and sensor data for each of the individual wells of a multi-well tray may be incorporated within the printing tray 4052 itself. The internal sampling system 4054 incorporated into the printing tray 4052 may collect samples, measurements, and/or test data from the material inside of the printing tray 4052. The internal sampling system 4054 incorporated into the printing tray 4052 may be integrated into the printing tray 4052 and/or multi-well plate and may be discarded after use (single-use). Alternatively, the internal sampling system 4054 incorporated into the printing tray 4052 may be removable from the printing tray 4052 and/or multi-well plate and may be inserted into an alternate printing tray 4052 and/or multi-well plate and re-sterilized for re-use (multi-use). The multi-use internal sampling system 4054 incorporated into the printing tray 4052 may incorporate some single-use elements such as single-use sensors, which may be discarded prior to inserting it into a new printing tray 4052 and/or multi-well plate. The internal sampling system 4054 incorporated into the printing tray 4052 may communicate the measurement and/or sensor data via a wired and/or wireless connection to the single-use printer chamber 4050 controller (not shown) and/or external measurement devices (not shown). Additionally and/or alternatively the material from the printing tray 4052 and/or multi-well plate may be sampled utilizing an internal sampling system 4058 incorporated into the printer chamber 4050. Each of the multi-well printing tray 4052 wells contains an opening, a seal, septum, and/or a closing assembly (not shown), which can allow material, particularly fluid based materials, into a sampling tubing assembly 4056 below the printing tray 4052. The sample tubing assembly 4056 may connect to at least one internal sampling system 4058 incorporated into the printer chamber 4050. The internal sampling system 4058 incorporated into the printer chamber 4050 may be a manual system, where an operator determines when a sample should be manually taken, or may be an automated system, where samples are taken at predetermined time intervals, by performing continuous sampling, and or by performing sampling based on intervals determined by the measurement data results. The fluid material tested by the internal sampling system 4058 incorporated into the printer chamber 4050 may be read by single-use sensors and the fluid material may be discarded after testing (not shown) or may be returned to the printing tray 4052 after testing. Measurement results from the at least one internal sampling system 4054 incorporated into the printing tray 4052 and/or at least one internal sampling system 4058 incorporated into the printer chamber 4050 may be manually entered and/or automatically (via a wired and/or wireless connection) communicated to the single-use printer chamber 4050 controller (not shown).

FIG. 27D is a top view of a multi-well plate printing tray 4082 on a printing platform 4080, where each of the wells contains a sampling assembly 4084, which may be an opening, a seal, a septum, and/or a closing assembly that can allow material, particularly fluid-based materials, into a sampling tubing assembly (not shown) below. The sampling assembly 4084 may be expertly arranged to provide at least one sampling port for each well of the multi-well plate printing tray 4082, may provide multiple sampling ports for each well, and/or may provide sampling ports to at least one representative well. A self-healing septum may be pierced by a plurality of needles stored within the printing platform 4080 or within the sampling tubing assembly (not shown) below to extract a metered sample from the well in the printing tray 4082.

FIG. 27E is a top view of a multi-well plate printing tray 4092 on a printing platform 4090, where each of the wells contains a plurality of single-use sensors 4094. The single-use sensors may be expertly arranged to provide at least one single-use sensor 4094 for each well of the multi-well plate printing tray 4092, may provide multiple single-use sensors 4094 for each well, and/or may provide at least one single-use sensors 4094 to at least one representative well.

Figure 28:
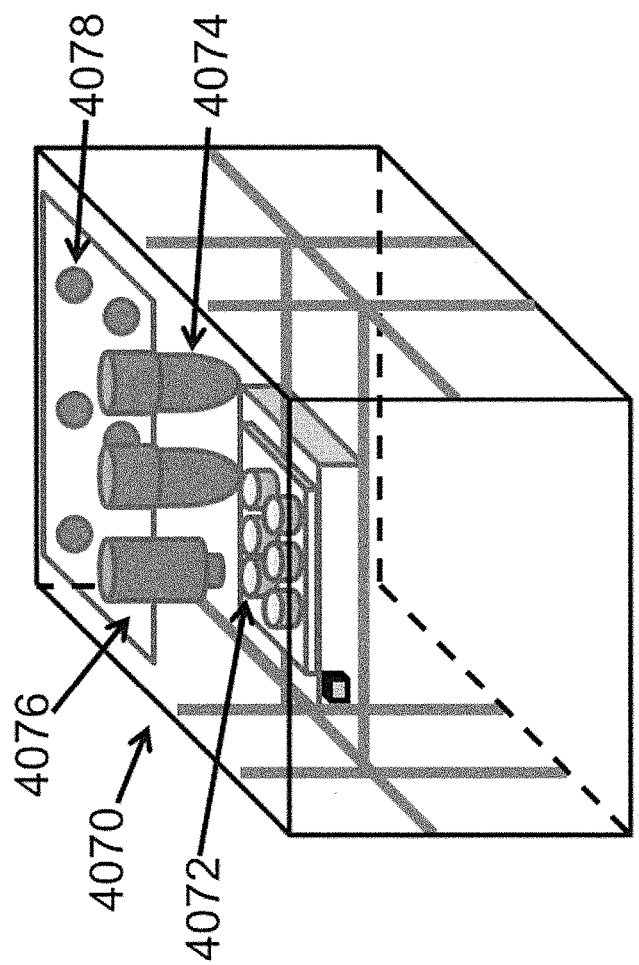
FIG. 28 illustrates an embodiment of a monitoring assembly for optical examination of the material in the printing tray.

FIG. 28 shows an embodiment of a monitoring assembly for optical examination of the material in the printing tray. The single-use printer chamber 4070 contains a printing tray 4072, which may be a multi-well plate, after structural material and/or biological material has been dispensed into the printing tray 4072 from the plurality of printing heads 4074. In addition or alternatively to a printing head 4074 placed in a static position through a port within the single-use printer chamber 4070, an optical measurement device 4076, such as a microscopic camera, may be placed and utilized to optically measure the contents of the printing tray 4072. A positional gantry aided by a positioning system 4078 comprising an array of cameras may be utilized to position the printing tray 4072 into the correct position to examine a specific section or well from the printing tray 4072, wherein the printing tray 4072 may be positioned to reach the correct focal distance for viewing the contents of the printing tray 4072. The optical measurement device 4076, such as a microscopic camera, may contain a zoom lens and/or autofocus to provide a clear image of the contents. Lighting may be provided below by LED lights in the printing platform shining through the printing tray 4072, or provided by an external source on the side of or below the single-use printer chamber 4070. Additionally and/or alternatively the array of cameras utilized for the positioning system 4078 may be utilized for recording the contents of the printing tray 4072, and not only for the positioning of the gantry setup. The array of cameras utilized for the positioning system 4078 may be positioned externally to the single-use printer chamber 4070 and view the internal assembly through a plurality of transparent windows and/or material. The optical measurement device 4076 and/or the array of cameras utilized for the positioning system 4078 may optically examine, measure, record, and store the optical data from the printing tray 4072 over a time period to determine and measure changes within the printed products inside of the printing tray 4072, such as in a time-lapse growth profile. The optical measurements may be utilized to determine if a structural support is of sufficient quality prior to the addition of biologically active products. The optical measurements may also be utilized to determine the profile, density, coverage, adherence, invasiveness, health, and viability of cell growth onto a structural support. The optical measurements may additionally examine other factors, like color change from a chromic die for measuring pH, temperature, or other factors. The optical measurements may additionally be able to examine the printing tray 4072 contents for potential contamination of bacteria, fungi, viruses, or other unwanted cell growth.

FIGS. 29A-29F show a vacuum-forming unit internal to a sterile chamber for the manufacturing of components for use with biologically active materials.

Figure 29A:
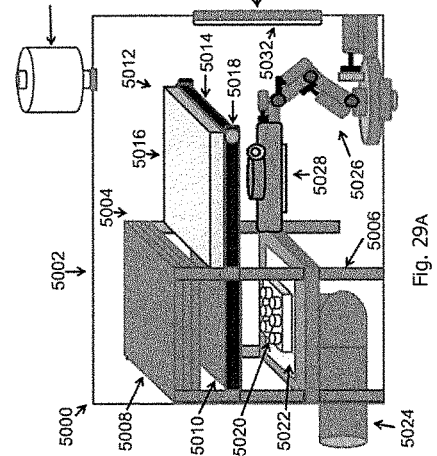
FIGS. 29A-29F illustrate an embodiment of a vacuum-forming unit internal to a sterile chamber for the manufacturing of components for use with biologically active materials.

FIG. 29A shows a side view of a sterile chamber assembly 5000 for the manufacturing of components for use with biologically active materials. A sterile chamber 5002, which may be made from flexible and/or rigid materials, contains at least one internal vacuum-forming unit 5004 for the forming of reproducible shapes utilizing vacuum-former support structure 5006 and a plurality of plastic sheets 5008 that are individually heated to a forming temperature using a heating element 5014. The forming is achieved by overlaying the plastic sheet over a mold 5020 and activating a vacuum pressure on a plate with a plurality of holes 5022 through an external source on the vacuum assembly 5024, which shapes the heated plastic sheet 5008 over the mold 5020 until it cools and solidifies in place. In this embodiment the vacuum-former support structure 5006 holds a plurality of plastic sheets 5008 above a sliding heater element assembly 5012. When the sliding heater element assembly 5012 is in the exterior position on a sliding platform 5018, a single plastic sheet 5010 is released and falls into place using guides into the heating tray holder. The sliding heater element assembly 5012 contains the heating element 5014 and an insulating layer 5016, which prevents the heat from the heating element 5014 to heat the plurality of plastic sheets 5008 above and make them reach forming temperature, or to protect the sterile chamber 5002 itself while heating the single plastic sheet 5010 below. The heating element 5014 may be an electrical heater, a single-use chemical reaction heating device, or may operate through the circulation of an externally-heated fluid source such as heated water, glycol, and/or steam. The plurality of plastic sheets 5008 may have a low melting-point profile so as not to require high heating temperatures for forming structures. The vacuum assembly 5024 may connect to an external vacuum source through the sterile chamber 5002. The vacuum assembly 5024 may utilize an aseptic connection and/or a sized air filter (not shown), such as a sterilizing grade air filter (not shown), which would allow sufficient airflow to result in the vacuum pressure required to shape the heated plastic sheet 5010 around the mold 5020. The sterile chamber 5002 may additionally contain a robotic arm 5026 for the placement of the mold 5020, for the cutting and/or die-cut punching of the formed product, for the removing of the formed product from the vacuum-forming unit 5004, for the transfer of the formed product to a storage assembly (not shown) and/or to a connected sterile chamber (not shown) through a transfer hatch 5034, and for the removal of waste plastic material from the vacuum-forming unit 5004 into a waste container (not shown). The robotic arm may contain a cutting assembly such as a cutting blade (not shown) or a die-cut assembly (not shown) within a robot-arm transfer head 5028 for cutting out the formed product after the vacuum forming has been completed. The robot-arm transfer head 5028 may additionally contain a vacuum assembly for creating a seal and holding onto the formed product during the transfer process. The mold 5020 may be a 3D printed product from another part of a sterile multi-chamber assembly (not shown). The sterile chamber 5002 may additionally contain a vent filter 5030, such as a sterilizing-grade vent filter, of sufficient size to maintain the integrity of the rigid and/or flexible sterile chamber 5002. For example the vent filter 5030 may have a large size if a flexible chamber is utilized, in order to prevent the chamber from collapsing in on itself during the maximum vacuum force from the vacuum assembly 5024. An additional support skeleton may be utilized to strengthen a flexible sterile chamber 5002. An additional transfer hatch support structure 5032 may be utilized to strengthen the transfer hatch 5034 during the maximum vacuum force from the vacuum assembly 5024. The transfer hatch support structure 5032 may be in a closed state during vacuum pressure inside the sterile chamber 5002 to prevent leakage of the vacuum force to an externally connected chamber (not shown) connected to the transfer hatch 5034.

Figure 29B:
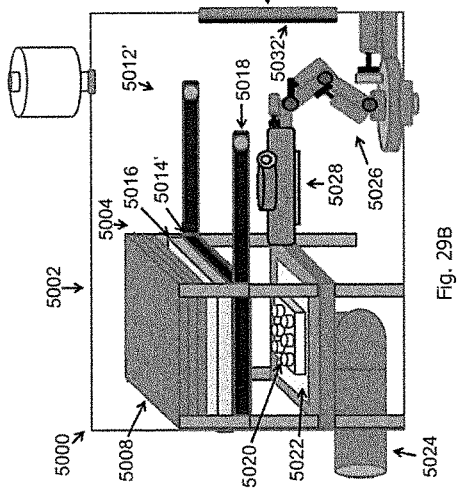

FIG. 29B shows a side view of a sterile chamber 5002 containing at least one internal vacuum-forming unit 5004. In this embodiment the sliding heater element assembly 5012' is in the internal position on the sliding platform 5018. The heating element 5014' is engaged in covering and heating the single plastic sheet 5010 (not shown), while the insulating layer 5016 is preventing the heat from the heating element 5014' from heating the plurality of plastic sheets 5008 above the assembly. In preparation for the vacuum force, the transfer hatch support structure 5032 is engaged into the closed state to strengthen the transfer hatch 5034 and prevent leakage of the vacuum force to an externally connected chamber (not shown).

Figure 29C:
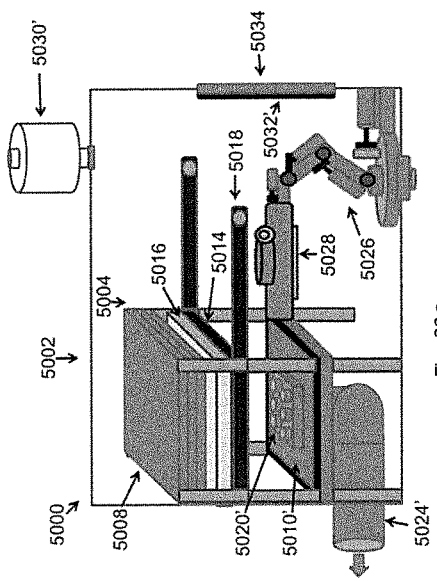

FIG. 29C shows a side view of a sterile chamber 5002 containing at least one internal vacuum-forming unit 5004. In this embodiment the sliding heater element 5014 has heated the single plastic sheet 5010' to the proper forming temperature. The vacuum assembly 5024' is activated using an external vacuum source on the vacuum former, providing vacuum pressure on a plate with a plurality of holes 5022. The heated single plastic sheet 5010' is released and follows the guides to drop directly over the mold 5020'. As it covers the mold 5020', the vacuum pressure from below stretches the single plastic sheet 5010' to take the shape of the mold and adhere to the plate with a plurality of holes 5022. A frame (not shown) may or may not be used to hold the edges of the plastic sheet 5010' in place during the vacuum-forming process. The vent filter 5030' is sized to provide sufficient airflow into the sterile chamber 5002 during the maximum vacuum force from the vacuum assembly 5024' when it is engaged.

Figure 29D:
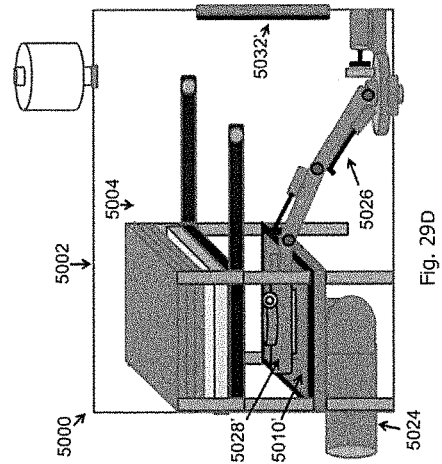

FIG. 29D shows a side view of a sterile chamber 5002 containing at least one internal vacuum-forming unit 5004. The vacuum pressure from the vacuum assembly 5024 is stopped and the formed single plastic sheet 5010' around the mold 5020 is allowed sufficient time to cool and solidify. In this embodiment the robotic arm 5026' moves to cover the formed product (not shown) from the single plastic sheet 5010' over the mold 5020. The robot-arm transfer head 5028 contains a die-cut assembly (not shown) for cutting out the formed product after the vacuum forming has been completed. The robot-arm transfer head 5028 additionally contains a vacuum assembly for creating a seal and holding onto the formed product during the transfer process to a storage area. In this embodiment the formed product is a multi-well plate for use with a printing tray and printing of structural materials and biologically-active materials within a three-dimensional printing chamber that is connected directly or indirectly to the sterile chamber 5002 through the transfer hatch 5034.

Figure 29E:
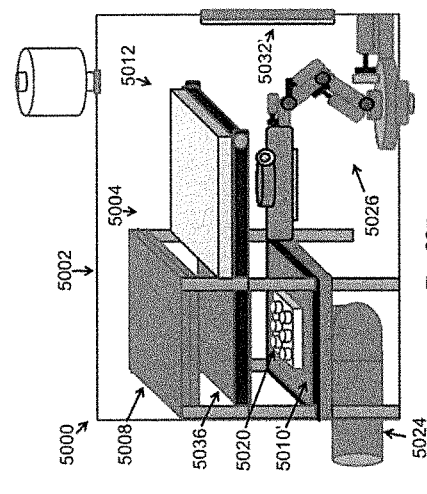

FIG. 29E shows a side view of a sterile chamber 5002 containing at least one internal vacuum-forming unit 5004. The sliding heater element assembly 5012 slides into the external position on the sliding platform 5018 and an additional single plastic sheet 5036 is released and falls into place using guides into the heating tray holder. The robotic arm 5026 moves into position to remove the remaining plastic material 5010' on the vacuum former plate with a plurality of holes 5022. The robot-arm transfer head 5028 utilizes an internal vacuum and/or plurality of suction cups to attach to the remaining plastic material 5010', lifts it over the mold 5020, and places it into a waste container (not shown) inside of the sterile chamber 5002 for discarding. The transfer hatch support structure 5032 is opened to allow for the formed product to be moved through the transfer hatch 5034 into another chamber, where it may be utilized or undergo further processing.

Figure 29F:
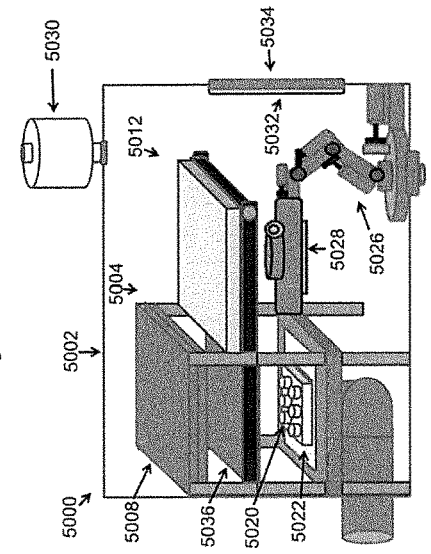

FIG. 29F shows a side view of a sterile chamber 5002 containing at least one internal vacuum-forming unit 5004. The vacuum-forming unit 5004 is returned to the original state for forming an additional product from a new single plastic sheet 5036. The use of a vacuum-forming unit internal to a sterile assembly allows to form a product of a particular design by re-using a mold so that a plurality of products formed in such manner, such as a multi-well assembly for use as a printing tray, may be utilized over and over again within a process inside a network of sterile chamber 5002 assemblies. A vacuum-forming process is faster, easier and has a more consistent manufacturing than current three-dimensional printing methods.

FIGS. 30A-30E show an injection-molding unit internal to a sterile chamber for the manufacturing of components for use with biologically active materials.

FIG. 30A shows a side view of a sterile chamber assembly 5050 for the manufacturing of components for use with biologically active materials. An internal sterile chamber 5054, which may be made from flexible and/or rigid materials, contains at least one internal injection-molding unit 5062 for the forming of reproducible shapes utilizing a melted material injected into a solid mold 5078. In this embodiment the sterile chamber assembly 5050 contains an outer jacketed container 5052 where a cooling fluid, such as cold sterile filtered water, is recirculated 5056 to maintain a stable internal chamber temperature with the heating element 5070 from the internal injection-molding unit 5062. A plurality of plastic supports (not shown), with openings to promote fluid circulation, may be in place between the outer jacketed container 5052 and the internal sterile chamber 5054 to hold the internal sterile chamber 5054 in place. To connect the internal sterile chamber 5054 with the outer jacketed container 5052 at least one vent filter assembly 5060 utilizes at least one connection tube 5058. To connect the internal sterile chamber 5054 with the outer jacketed container 5052 a transfer hatch assembly 5088 utilizes a connection tube to an internal transfer hatch 5086. The at least one internal injection-molding unit 5062 inside of the internal sterile chamber 5054 contains a stand 5064, a hopper 5066 filled with a low-melting-point moldable material, such as plastic pellets, and a feed tube 5068 to feed the moldable material from the hopper 5066 into the insulated heating element 5070. The insulated heating element 5070 heats the moldable material, such as the plastic pellets, into a melted material which is extruded under compression force utilizing a compression motor 5074. The melted material is extruded utilizing a metered dispenser 5076 into a solid mold 5078. As heat rises from the insulated heating element 5070 inside of the internal sterile chamber 5054, an insulated thermal barrier 5072 may be used to prevent deformation and/or damage of the internal sterile chamber 5054 walls from the excess heat. In addition to fluid circulation in the jacketed container 5052, to maintain a stable temperature the vent filter assembly 5060 and/or a plurality of vent filters may be utilized to perform a fluid air exchange to remove excess heat from the internal sterile chamber 5054. Both the jacketed fluid and/or the air exchange may utilize an external heat exchanger device (not shown) to maintain and control the internal temperature of the internal sterile chamber 5054. A plurality of temperature sensors (not shown) may be located within the internal sterile chamber 5054 and/or the outer jacketed container 5052 to provide temperature measurements for the proper regulation of temperature by external devices (not shown). The solid mold 5078 may comprise at least two parts that are closed and sealed with a motor 5080. The injection molded material is allowed to cool and solidify within the solid mold 5078 and is removed utilizing a removal tool 5082 which places the final injection molded product into a holding container 5084.

FIG. 30B shows a side view of an internal sterile chamber 5054 containing at least one internal injection-molding unit 5062'. In this embodiment the insulated heating element 5070' is actively heating the moldable material from the hopper 5066, such as the plastic pellets, into a melted material. The insulated heating element 5070' may be an electrical heater, a single-use chemical reaction heating device, or may operate through the circulation of an externally-heated fluid source such as heated water, glycol, and/or steam. The compression motor 5074' exerts a force on the melted material and pushes it through the metered dispenser 5076 into the solid mold 5078'. The compression motor 5074' may be driven by hydraulic, pneumatic, electric, or magnetically controlled methods (not shown). The injection-molded material is allowed to cool and solidify within the solid mold 5078'.

FIG. 30C shows a side view of an internal sterile chamber 5054 containing at least one internal injection-molding unit 5062". In this embodiment at least one part of the solid mold 5078" is separated by retracting the first part using the motor 5080', thereby exposing the final injection-molded product 5090.

FIG. 30D shows a side view of an internal sterile chamber 5054 containing at least one internal injection-molding unit 5062'''. In this embodiment the removal tool 5082' is activated and pushes, pulls, and/or scrapes the final injection-molded product 5090' out of the second part of the solid mold 5078 and into a holding container 5084.

FIG. 30E shows a side view of an internal sterile chamber 5054 containing at least one internal injection-molding unit 5062. In this embodiment the internal injection-molding unit 5062 has returned to the original state in that the compression motor 5074 has returned to the original position. As the internal barrel (not shown) of the compression motor 5074 moves up the plastic pellets of the moldable material from the hopper 5066', it fills the empty chamber (not shown) causing a reduction in height of the moldable material from the hopper 5066' reservoir. The motor 5080 can return the first part of the solid mold 5078 to the second part forming a sealed container for the next injection mold. The final injection-molded product 5090' may be individually removed from the holding container 5084 utilizing a robotic arm (not shown) or the entire holding container 5084 may be removed after it has been filled with a plurality of final injection-molded products 5090'. The final injection molded product 5090' may be moved through the internal transfer hatch 5086 and the outer transfer hatch 5088 into another chamber where it may be utilized or undergo further processing.

Figure 31A:
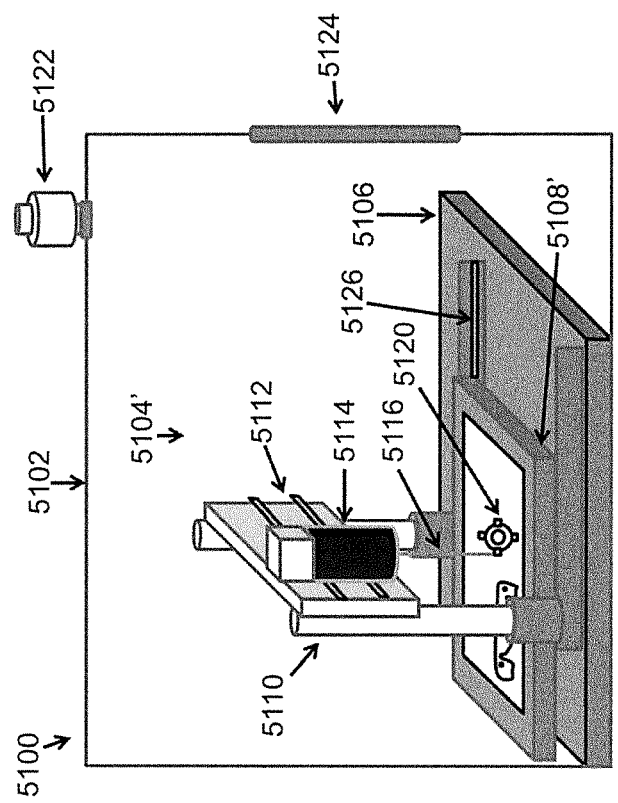
FIGS. 31A and 31B illustrate an embodiment of a laser-cutting device internal to a sterile chamber for the manufacturing of components for use with biologically active materials.

FIGS. 31A and B show a laser-cutting device internal to a sterile chamber for the manufacturing of components for use with biologically active materials.

FIG. 31A shows a side view of a sterile chamber assembly 5100 for the manufacturing of components for use with biologically active materials. A sterile chamber 5102, which may be made from flexible and/or rigid materials, contains at least one laser-cutting device 5104 for the precision-cutting of shapes utilizing a laser 5114 to cut material from a substrate 5118. In this embodiment the at least one laser-cutting device 5104 is supported by a solid base 5106 and a two-axis controller positioning system. In this embodiment the laser-cutting device 5104 contains a platform 5108 that moves along the horizontal x-axis along a track 5126. The laser assembly 5114 is held by a support structure 5110, which contains a track 5112 for the z-axis movements of the laser assembly 5114. The laser beam 5116 comes from the assembly and is utilized to cut through a substrate 5118 located on the platform 5108 with precision. The laser cut products 5120 from the laser assembly may be utilized for manufacturing components for use with biologically active materials. Additionally and/or alternatively the laser may be utilized to laser-label some materials for information and/or coding. A plurality of vent filters 5122 may be utilized to regulate the pressure of the sterile chamber 5102 and may additionally be utilized to remove smoke or aerosolized particulates from the laser 5116 burning through the substrate 5118. The exterior wall of the sterile chamber 5102 may be coated with an absorbing material to block and reduce the intensity of the laser 5116 at the specific wavelengths that the laser assembly 5114 operates at. This will reduce the risk of exposure to the operator even if they are not wearing laser safety eyewear for protection. The laser-cut products 5120 from the substrate 5118 may be moved out of the sterile chamber 5102 through a transfer hatch 5124. The internal laser assembly 5114 may be powered by an external electrical connection, an internal battery storage mechanism, an inductively-charged electrical connection, a chemical reaction, a microwave or visual line-of-sight power source, or other wireless power source. The two-axis motor control mechanism may be driven by hydraulic, pneumatic, electric, or magnetically controlled methods (not shown).

Figure 31B:
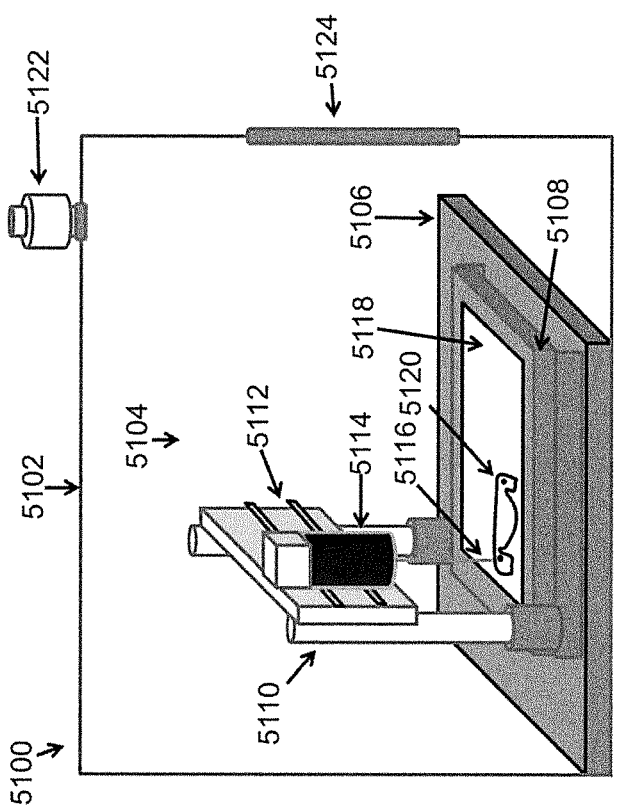

FIG. 31B shows a side view of a sterile chamber 5102 that contains at least one laser-cutting device 5104 for the cutting of shapes utilizing a laser 5114 to cut material from a substrate 5118. In this embodiment the at least one laser-cutting device 5104' contains a platform 5108' which has moved along the horizontal x-axis via a track 5126. The laser assembly 5114 has moved along the z-axis via a track 5112. The combined movements of the laser assembly 5114 and of the platform 5108' were able to control the laser beam 5116 to precisely cut the laser-cut products 5120 from the substrate 5118 located on the platform 5108'. Alternatively the laser assembly 5114 may be in a fixed position inserted through a port (not shown) in the sterile chamber 5102 and the platform 5108 may move along two-axis for positioning the substrate 5118. Additionally the laser assembly 5114 may be aseptically connected to the sterile chamber 5102 or sterilized in place during connection with the sterile chamber 5102 as previously described. The final laser-cut products 5120 may be individually removed from the platform 5108' and placed into a holding container (not shown) utilizing a robotic arm (not shown). Additionally or alternatively a robotic arm (not shown) may be utilized to assemble the final laser-cut products 5120 into an assembly (not shown). The robotic arm (not shown) may be utilized to move the individual laser-cut products 5120 or the assembled product (not shown) into another chamber where it may be utilized or undergo further processing.

Figure 32:
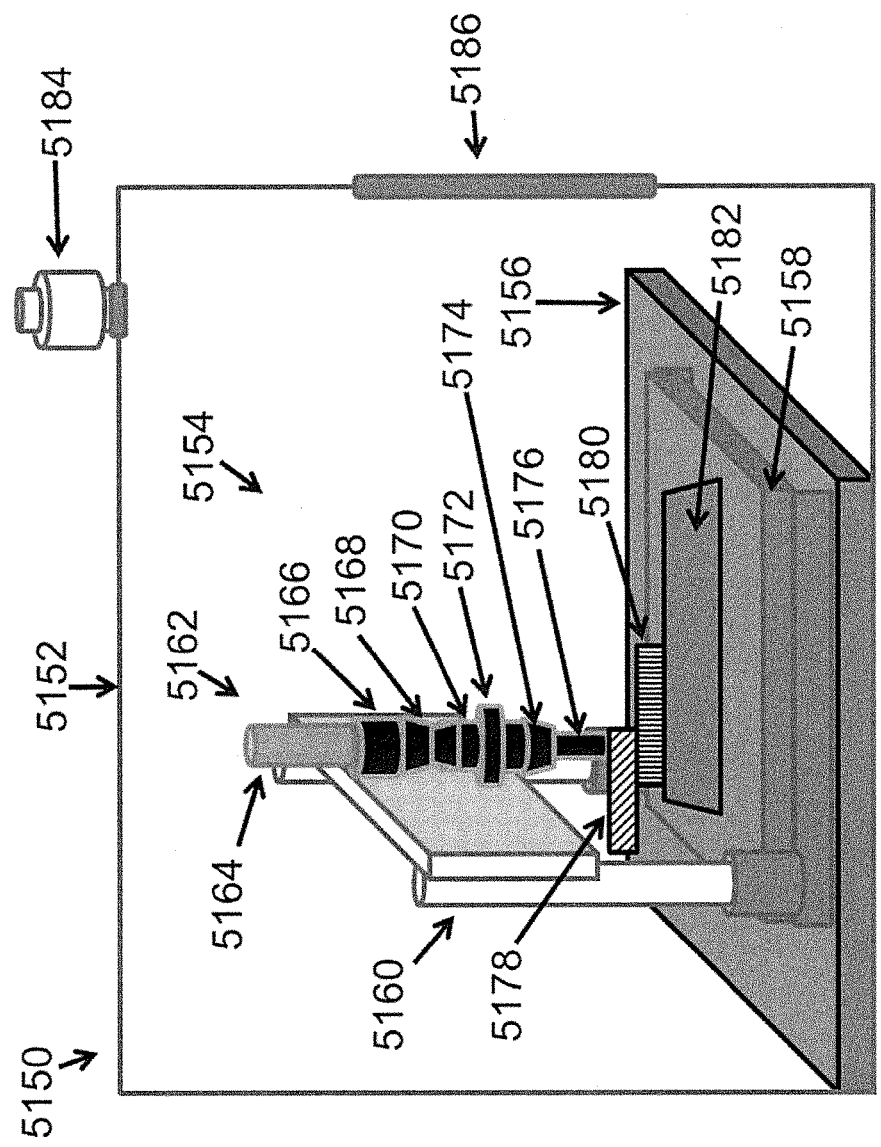
FIG. 32 illustrates an embodiment of an ultrasonic-welding device internal to a sterile chamber for the joining of manufactured components for use with biologically active materials.

FIG. 32 shows an ultrasonic-welding device internal to a sterile chamber for the joining of manufactured components for use with biologically active materials. A sterile chamber 5152, which may be made from flexible and/or rigid materials, contains at least one ultrasonic-welding device 5154 which welds at least two separate materials, such as two plastic materials, together to form a single component. In this embodiment the at least one ultrasonic-welding device 5154 may contain a platform base 5156, which may contain a vibrational damper (not shown) or be made from vibrational-damping materials to prevent the vibrational energy from the ultrasonic welder from being transferred to the sterile chamber 5152. The ultrasonic-welding device 5154 may contain a movable platform 5158 on the platform base 5156. The movable platform 5158 may contain a support structure 5160 to hold an ultrasonic-welding assembly 5162 in place above an anvil 5182. The ultrasonic-welding assembly 5162 may contain a piston 5164, which may be driven by hydraulic, pneumatic, electric, or magnetically controlled methods (not shown). The ultrasonic-welding assembly 5162 may contain a transducer 5166, a converter 5168, a booster 5170, a collar 5172, a sonotrode 5174, and a horn 5176. The sonotrode 5174 and horn 5176 assembly comes in contact with a first weldable component 5178 that is in physical contact with a second weldable component 5180. The first weldable component 5178 and the second weldable component 5180 are lined up for ultrasonic welding on the anvil 5182. Electrical energy is transformed into vibrational energy in the ultrasonic-welding assembly 5162 and makes the interface between the weldable components 5178 and 5180 vibrate at thousands of times per second. The vibrations create frictional heat that causes the materials from the weldable components to melt together forming a single welded component. The standard frequencies utilized with ultrasonic sonotrodes range from about 20 kHz to about 70 kHz and the amplitude of the vibrations is approximately 13 to 130 micrometers. A robotic arm (not shown) within the assembly may precisely position the first weldable component 5178 and the second weldable component 5180. The ultrasonic-welding device 5154 may be powered by an external electrical connection, an internal battery storage mechanism, an inductively-charged electrical connection, a chemical reaction, a microwave or visual line-of-sight power source, or other wireless power source. The robotic arm (not shown) may additionally be utilized for removing the welded assembly from the anvil 5182 and placing it into a holding container (not shown) or moving the welded assembly into another chamber through a transfer hatch 5186 where it may be utilized or undergo further processing.

Figure 33:
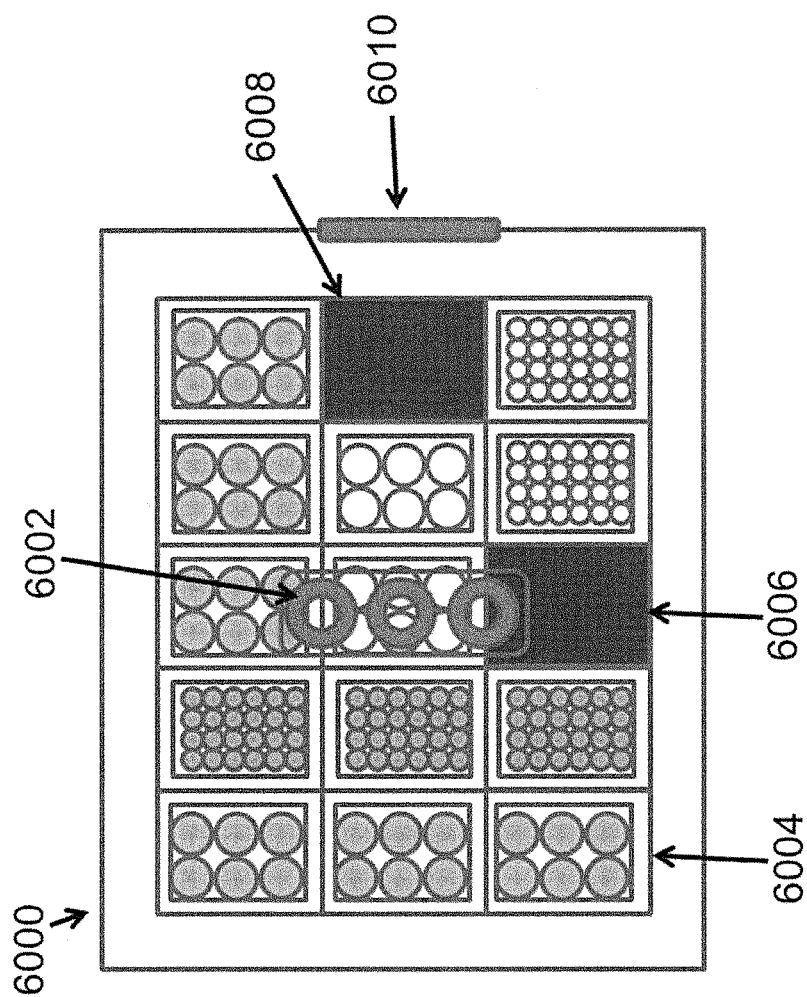
FIG. 33 illustrates an embodiment of a three-dimensional printing assembly inside of a sterile single-use chamber.

FIG. 33 shows a three-dimensional printing assembly inside of a sterile single-use chamber 6000, which may be made from flexible and/or rigid materials and contains a plurality of printing heads 6002, which are used to dispense materials into a printing tray. In this embodiment the printing platform is a multi-segmented tile printing platform that contains a plurality of printing trays 6004 on a plurality of multi-segmented tiles, where at least one of the tiles is missing to allow for each of the individual tiles to move to all possible positions on the printing platform. The multi-segmented printing platform may be driven by hydraulic, pneumatic, electric, or magnetically-controlled methods (not shown) or as previously described. In this embodiment the multi-segmented printing platform is missing at least two tiles 6006 and 6008 to properly position the central tile in both the x-axis and z-axis during the printing process with a plurality of fixed printing heads 6002. In this embodiment the plurality of printing trays 6004 comprises multi-well plates, wherein the plurality of printing heads 6002 may dispense a metered amount of liquid media, three-dimensionally-print structural material, and/or three-dimensionally-print cells onto the structural material, and dispense a metered amount of at least one drug product for the in-vitro testing of the cell products inside of the multi-well plates. The applications could be preclinical efficacy and toxicology testing of drug products on the cells or other bioactive materials. A plurality of cell types may be utilized, for example in a method for screening a patient's own cells grown up in a bioreactor and determine the optimal drug treatment regimen based on the efficacy and toxicology measured within the plurality of printing trays 6004. The sterile single-use chamber 6000 may be regulated to a temperature for incubating the cells within the plurality of printing trays 6004. A transfer hatch 6010 may be utilized for the aseptic transfer of the materials inside of the sterile single-use chamber 6000 or for the transfer of materials to a network of chambers connected by the transfer hatch 6010.

Figure 34:
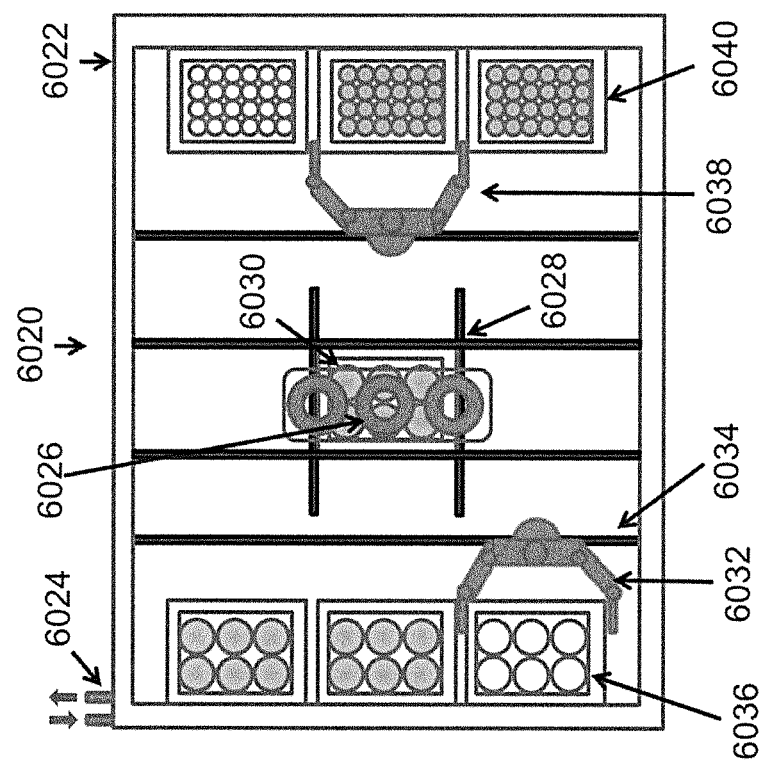
FIG. 34 illustrates an embodiment of a three-dimensional printing assembly inside of a sterile single-use chamber.

FIG. 34 shows a three-dimensional printing assembly inside of a sterile single-use chamber 6020, which may be made from flexible and/or rigid materials and contains a plurality of printing heads 6026 that are used to dispense materials into a printing tray 6030. In this embodiment the printing tray 6030 moves along a printing platform (not shown) along a three-axis gantry setup 6028 during the printing process with a plurality of fixed printing heads 6026. In this embodiment the printing tray 6026 is a multi-well plate, where the plurality of printing heads 6026 may dispense a metered amount of liquid media, three-dimensionally-print structural material, and/or three-dimensionally-print cells onto the structural material, and dispense a metered amount of at least one drug product for the in-vitro testing of the cell products inside of the multi-well plates. In this embodiment a plurality of robotic arms 6032 and 6038 may be utilized to place an empty printing tray 6036 onto the printing platform (not shown) for printing with the plurality of printing heads 6026. The robotic arms 6032 and 6038 may additionally be utilized to move a printing tray 6040, which has completed printing, to a storage location. The storage location may contain a plurality of moving racks for stacking the printing trays within the sterile single-use chamber 6020 to maximize the use of the space as well as to increase the throughput of printing trays 6040 capable of being printed, measured, studied, and/or screened within the chamber 6020. In this embodiment the plurality of robotic arms 6032 and 6038 move along a plurality of tracks 6034 to increase the range of motion for the robotic arms 6032 and 6038 and increase the area available for stacking and/or storage of printing trays 6036 and 6040. The sterile single-use chamber 6020 may be regulated to a temperature for incubating the cells and/or bioactive products within the plurality of printing trays 6004. In this embodiment the sterile single-use chamber 6020 is a jacketed chamber that contains an outer jacketed chamber 6022 and uses the circulation 6024 of a fluid, such as sterile filtered water, for regulating and/or maintaining the proper temperature for the chamber 6020. A transfer hatch (not shown) may be utilized for the aseptic transfer of the materials inside of the sterile single-use chamber 6020 or for the transfer of materials to a network of chambers connected by the transfer hatch (not shown).

Figure 35:
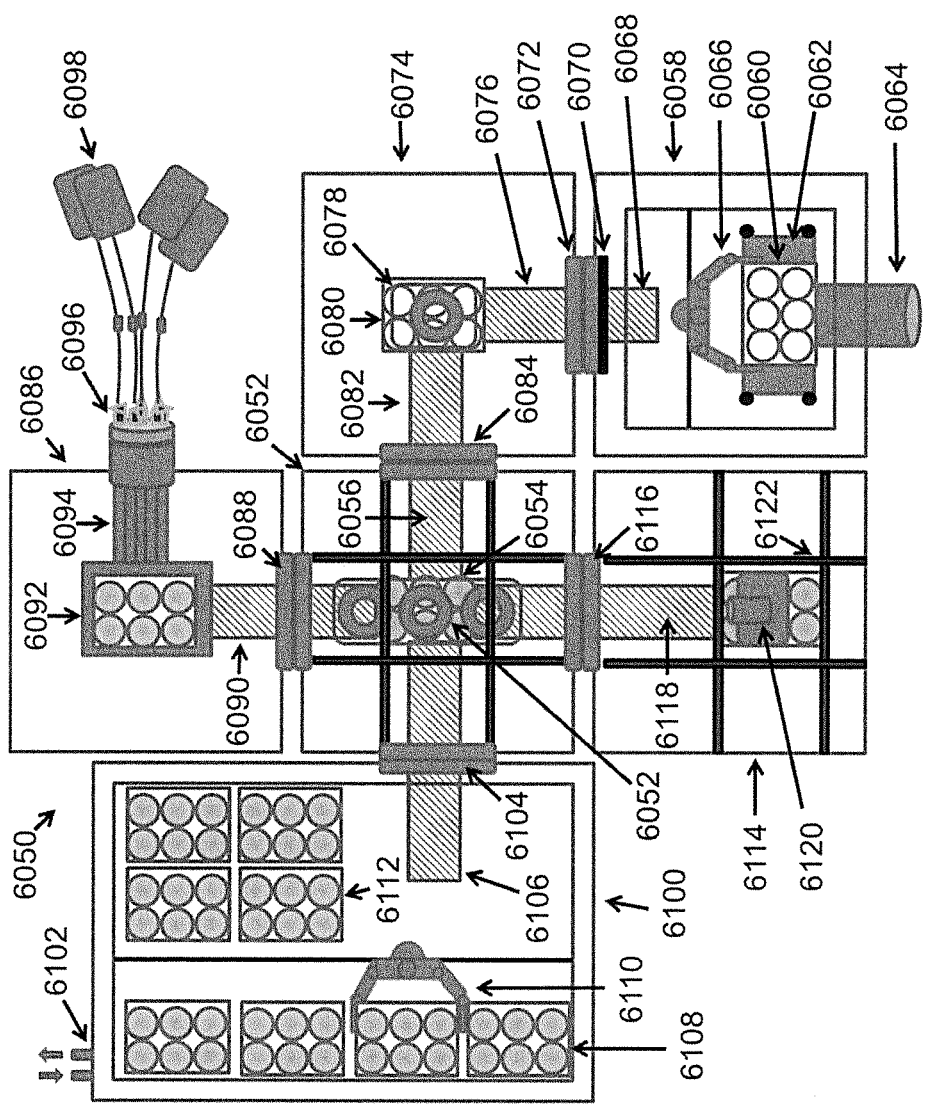
FIG. 35 illustrates an embodiment of a network of single-use chambers, each with their own functionalities, which forms a single-use manufacturing assembly operating within a sterile environment.

FIG. 35 shows a top view of a network of single-use chambers, each with their own functionalities, which forms a single-use manufacturing assembly operating within a sterile environment. The network of single-use chambers 6050 provides a method to connect individual single-use chambers within a certain arrangement to perform a manufacturing, testing, screening, and/or measurement function. In this embodiment the central single-use three-dimensional printing chamber 6052 is connected to a plurality of other chambers each with their own functionalities. In this embodiment the process starts in the single-use vacuum-forming chamber 6058, which utilizes a vacuum-forming unit 6062 to form a heated plastic piece over a mold by exploiting a strong vacuum using the external vacuum port 6064. In this embodiment the vacuum-formed product is a multi-well plate 6060. A robotic arm 6066 grabs the formed multi-well plate 6060 and places it onto a conveyor belt 6068 that moves the multi-well plate 6060 through a transfer hatch 6072, when the vacuum is not running and a hatch support structure 6070 is in the opened state, and into a single-use multi-well-plate coating chamber 6074. The conveyor belt may be made from sterilizable materials and may be driven by hydraulic, pneumatic, electric, or magnetically-controlled methods (not shown) or as previously described. Alternatively or additionally the multi-well plates or other material inputs may be pre-sterilized in an alternate sterile chamber (not shown) and connected to the network of single-use chambers 6050. Alternatively the multi-well plates or other material inputs may be aseptically connected via a transfer hatch (not shown). In another embodiment the multi-well plates or other inputs may utilize a sterilization chamber (not shown) where the non-sterile materials are inserted and the container is sealed, the chamber is sterilized utilizing a validated method and load configuration such as by chemical sterilization by vaporized hydrogen peroxide (VHP) and the sterilization chamber is either connected to the network of single-use chambers 6050 by an aseptic connector (not shown) or was already connected and the barrier (not shown) between the connected chambers is aseptically removed. An additional conveyor belt 6076 moves the multi-well plate 6080 below a fixed printing head 6078 that spray-coats the multi-well plate 6080 in preparation for the printing process. The spray coating may prepare the multi-well plate 6080 for the adhesion of structural materials and/or cells, or may be utilized to keep the cells suspended and not adhering to the side walls. Additionally and/or alternatively the spray coating may add growth factors that support the growth of certain cell types within the multi-well plate 6080. The spray coating from the printing head 6078 may be non-specific and coat the entire plate or may be specific and coat only specific regions of the plate or with a specific pattern or design. The completed multi-well plate 6054 after spray coating moves along a conveyor 6082 through a transfer hatch 6084 and into the central single-use three-dimensional printing chamber 6052. The multi-well plate 6054 enters a printer three-axis gantry setup (not shown) and undergoes three-dimensional printing with a plurality of printing heads 6052. In this embodiment the plurality of printing heads 6052 may dispense a metered amount of liquid media, three-dimensionally-print structural material, and/or three-dimensionally-print cells onto the structural material, and dispense a metered amount of at least one drug product for the in-vitro testing of the cell products inside of the multi-well plates. The printed multi-well plate 6054 moves along a conveyor belt 6056 through a transfer hatch into a single-use incubation and storage chamber 6100. The printed multi-well plate 6054 moves onto a conveyor belt 6106, where the robotic arm 6110 moving along a track grabs it and places it in an open storage space inside the stackable incubation chamber. In this embodiment the single-use incubation and storage chamber 6100 is a jacketed chamber that contains an outer jacketed chamber and uses the circulation 6102 of a fluid, such as sterile filtered water, for regulating and/or maintaining the proper temperature within the chamber. The multi-well plates may be tracked by an individualized labeled barcode (not shown). After a period of time for incubation, the multi-well plates 6108 and 6112 inside of the single-use incubation and storage chamber 6100 are sent for testing and examination. The robotic arm grabs the incubated multi-well plate, such as 6108, and transfers it to the conveyor belt 6106, which moves it to the central single-use three-dimensional printing chamber 6052 and down a conveyor belt 6118 through a transfer hatch into the single-use optical examination chamber 6114. The conveyor belt 6118 loads the incubated multi-well plate into the three-axis gantry setup 6122 where it is positioned at the proper focal length from the optical measurement device 6120, which is at a fixed position within the chamber. In this embodiment the optical measurement device 6120 is a microscopic imager, where the incubated multi-well plate is illuminated by LED lights (not shown) and the microscopic images are captured, stored on an external device, and compared to previous images. After the incubated multi-well plate has completed optical measurement in the single-use optical examination chamber 6114, it is loaded back onto the conveyor belt 6118 through the central single-use three-dimensional printing chamber 6052, through a transfer hatch 6088, onto the conveyor belt 6090, and into the single-use sampling chamber 6086. The single-use sampling chamber 6086 contains a platform 6092 that utilizes a previously described sampling mechanism (not shown) to sample the material from the incubated multi-well plate. The sampled material moves through a sampling tubing assembly 6094 and to a single-use sampling assembly 6096, which in this embodiment is a TakeONE® single-use sampling assembly. The material sampled from the incubated multi-well plate enters into a sterile container 6098, which is aseptically removed from the single-use sampling assembly 6096 and tested on an external measurement device (not shown). After sampling has been completed, the incubated multi-well plate may be returned to the single-use incubation and storage chamber 6100 for further incubation, sent to the single-use three-dimensional printing chamber 6052 for further printing and/or the addition of media or a metered dose of at least one drug product, sent to the single-use optical examination chamber 6114 for additional optical examination, sent to a separate chamber (not shown) for non-incubated storage, or removed from the chamber and discarded (not shown). Alternatively all of the multi-well plates may be discarded when the batch testing has been completed and the plurality of single-use chambers 6052, 6058, 6074, 6086, 6100, and 6114 are disconnected, sterilized for disposal, and discarded.

The following items may be useful for understanding the invention:

Item 1. A three dimensional printing device comprising:
  a sterilizable printer assembly including
    at least one printing head,
    a printing platform, and
    a driving mechanism adapted to achieve a relative displacement between the at least one printing head and the printing platform along two or three degrees of freedom;
  a printer housing enclosing the printer assembly in a sterile manner,
  at least one aseptic connector fluidly connected to a corresponding one of the at least one printing head.

Item 2. The three dimensional printer of item 1, wherein a pre-sterilized printer head may be aseptically connected to the sterile three dimensional printing chamber.

Item 3. The three dimensional printer of item 1, wherein a non-sterilized printer head may be inserted into a printer head insertion assembly within the sterile three dimensional printing chamber and sterilized utilizing a chemical sterilization method.

Item 4. The printer head of item 1, wherein the printer head is utilized to dispense a metered volume of at least one drug product. The at least one drug product may be fluidly connected to the printer head via an aseptic connection.

Item 5. A printing system comprising:
  a three dimensional printing device having:
  a sterilizable printer assembly including
  a tethered multiaxis printing assembly including
    at least one printing head, with a tubing line to a port in the chamber for transferring fluid and/or material inputs to be dispensed by the at least one printing head.
    an aseptic connector to connect an external fluid and/or material connection to the port in the sterile chamber.
  a plurality of soft robotics actuators for positioning the tethered multiaxis printing assembly into position over a fixed printing platform.
    an externally driven hydraulic and/or pneumatic drive mechanism to control the movements of the soft robotic actuators.
  a central body to connect the at least one printing head to the plurality of soft robotics actuators and the inputs and fluid connections for dispensing and positioning the assembly for printing on the printing platform.

Item 6. A printing system comprising:
  a three dimensional printing device having:
  a sterilizable printer assembly including
  an untethered multiaxis printing assembly including
    at least one printing head, with a plurality of fluid reservoirs.
  a plurality of robotic appendages for positioning the untethered multiaxis printing assembly into position over a fixed printing platform.
    an internally powered drive mechanism to control the movements of the robotic appendages.
  a central body to connect the at least one printing head, the plurality of fluid reservoirs, and the plurality of robotic appendages for dispensing and positioning the assembly for printing on the printing platform.

Item 7. A robotic arm assembly comprising:
  a sterilizable chamber including
  a robotic arm assembly made from sterilizable components internal to the sterilizable chamber including
    at least one actuator
    at least one articulating support
    at least one gripping assembly
    at least one control mechanism
    at least one positional system and at least one driving mechanism adapted to achieve a relative displacement within the sterilizable chamber.

Item 8. The robotic arm assembly of item 7, wherein the at least one driving mechanism is a hydraulic and/or pneumatic fluid pressure source. The hydraulic and/or pneumatic fluid pressure source may originate from an external control assembly where the fluid lines are aseptically connected to the robotic arm assembly within the sterilized chamber.

Item 9. The robotic arm assembly of item 7, wherein the at least one control mechanism is a manual control mechanism where an operator may manually manipulate the controls of the robotic arm assembly internal to the sterile chamber.

Item 10. The robotic arm assembly of item 7, wherein the at least one control mechanism is an automated control mechanism which is controlled by a computer setup and/or an electronic device.

Item 11. The robotic arm assembly of item 7, wherein the at least one positional system is a plurality of cameras located on the sterile chamber and/or a plurality of cameras located on the robotic arm assembly.

Item 12. The robotic arm assembly of item 7, wherein the robotic arm internal to the sterile chamber is utilized for moving and stacking a plurality of components, materials, and or printer trays.

Item 13. The robotic arm assembly of item 7, wherein the robotic arm internal to the sterile chamber is utilized for assembling at least two components into an assembly.

Item 14. The robotic arm assembly of item 7, wherein the robotic arm internal to the sterile chamber is utilized for moving a plurality of components from one sterile chamber to another sterile chamber aseptically connected through the transfer hatches.

Item 15. The robotic arm assembly of item 7, wherein the robotic arm internal to the sterile chamber is a soft robotics assembly comprised of soft flexible materials and a plurality of inflatable sections.

Item 16. The robotic arm assembly of item 7, wherein the robotic arm internal to the sterile chamber is an inflatable robotics assembly comprised of a plurality of inflatable sections for the robotic arm supporting structures.

Item 17. A vacuum forming assembly comprising:
a sterilizable chamber including
a vacuum forming assembly made from sterilizable components internal to the sterilizable chamber including
  at least one rigid support structure
  at least one vacuum platform with a plurality of holes
  at least one vacuum pressure source
  at least one heating element
  at least one dispensing mechanism for dispensing moldable plastic sheets
  at least one mold,
  and at least one vent filter assembly.

Item 18. An injection molding assembly comprising:
a sterilizable chamber including
an injection molding assembly made from sterilizable components internal to the sterilizable chamber including
  at least one rigid support structure
  at least one reservoir with moldable material
  at least one heating element
  at least one compression source
  at least one dispensing unit
  at least one solid mold comprising of at least two parts
  and at least one vent filter assembly.

Item 19. A laser cutting assembly comprising:
a sterilizable chamber including
a laser cutting assembly made from sterilizable components internal to the sterilizable chamber including
  at least one rigid support structure
  at least one 2 axis positioning assembly
  at least one laser assembly
  at least one power source
  at least one substrate
  and at least one vent filter assembly.

Item 20. An ultrasonic welding assembly comprising:
a sterilizable chamber including
an ultrasonic welding assembly made from sterilizable components internal to the sterilizable chamber including
  at least one rigid support structure
  at least one ultrasonic welder comprising of a piston
  a transducer
  a converter
  a booster
  a sonotrode
  a horn
  an anvil
  at least two materials two weld together.
  and at least one vent filter assembly.

Item 21. A single-use sampling assembly comprising:
a sterilizable chamber including
a sampling assembly made from sterilizable components internal and external to the sterilizable chamber including
  at least one fluid connection to the container to be sampled
  at least one single-use aseptic connection to the sterile chamber
  at least one sampling method for drawing fluid material from the desired chamber within the container to be sampled
  at least one collection container for holding the sampled fluid from the desired chamber within the container to be sampled
  at least one aseptic disconnection method for removal of the container containing the sample fluid.

Item 22. A continuous sampling assembly comprising:
a sterilizable chamber including
a sampling assembly made from sterilizable components external to the sterilizable chamber including
  at least one fluid connection to the container to be sampled
  at least one aseptic connection to the sterile chamber
  at least one sampling method for drawing fluid material from the desired chamber
  at least one external measurement device
  at least one pump and/or drive mechanism to draw the fluid to the at least one external measurement device.

Item 23. An internal sampling assembly comprising:
a sterilizable chamber including
a sampling assembly made from sterilizable components internal to the sterilizable chamber including
  at least one fluid connection to the container to be sampled
  a sampling method for drawing fluid material from the desired chamber
  an internal measurement device.

Item 24. An optical measurement assembly comprising:
a sterilizable chamber including
an optical measurement assembly made from sterilizable components internal and/or external to the sterilizable chamber including at least one optical measurement device, preferably a microscopic camera, containing a plurality of lenses and an autofocus.

at least one LED light source.

and at least one memory storage device.

Item 25. The optical measurement assembly of item 24, wherein the optical measurement assembly is comprised of a plurality of cameras positioned externally to the sterile chamber and views the internal assembly through a plurality of transparent windows and/or transparent material.

Item 26. A plurality of printer trays comprising multi-well plates comprising a plurality of wells.

Item 27. The plurality of printer trays of item 26, wherein the multi-well plates may be manufactured inside of the sterile chamber utilizing the at least one three dimensional printer, the at least one vacuum forming unit, the at least one injection molding unit, the at least one laser cutting unit, and/or the at least one ultrasonic welding unit.

Item 28. The plurality of printer trays of item 26, wherein the printer trays may be incubated under temperature regulated conditions for the growth of cells in nutrient rich media within the trays or within the scaffolding of the manufactured products.

Item 29. At least two sterile chambers may be aseptically connected together via the transfer hatch connections to form a network of sterile chambers where each sterile chamber performs a specific task.

Item 30. The network of sterile chambers of item 29, wherein the network of sterile chambers includes the manufacturing of a plurality of multi-well plates and spray coating with bioactive materials for growing cells in a nutrient rich media under incubated conditions, the use of cells grown in multi-well plates for the screening of three dimensional printed cell products, in vitro efficacy and toxicity studies of the effects of metered volumes of at least one drug products on three dimensional printed incubated cells within the multi-well plates.

Item 31. The network of sterile chambers of item 29, wherein the network of sterile chambers includes the manufacturing of a plurality of multi-well plates and spray coating with bioactive materials for growing cells in a nutrient rich media under incubated conditions, the use of cells grown in multi-well plates for the screening of three dimensional printed cell products, in vitro efficacy and toxicity studies of the effects of metered volumes of at least one drug products on three dimensional printed incubated cells within the multi-well plates.

Item 32. The network of sterile chambers of item 29, wherein the network of sterile chambers includes the manufacture of biologically active cell products, the printing of scaffolding materials for coating with bioactive products, the manufacture of complex multi-material assemblies for coating with bioactive products, the manufacture of complex multi-material medical devices with bioactive coatings, the printing of cells and cell products onto complex multi-material assemblies.

Item 33. The network of sterile chambers of item 29, wherein the network of sterile chambers includes the printing of cell products, cellular structures, scaffoldings, organs, and organ simulants grown from an individual patient's cells in a single-use bioreactor, processed, dispensed, incubated, and grown in a single-use sterile environment. The biologically grown product may be aseptically removed from the assembly and implanted into a patient in appropriate health care facility.

Item 34. The network of sterile chambers of item 29, wherein the network of sterile chambers includes the manufacture of biologically active products on biosensors inside a network of sterile chambers includes the printing of biologically active products onto electronic devices and/or substrates to add to electronic devices for the detection of an analyte. The analyte may be detected through the combination of a biological component with a physicochemical detector.

Item 35. The network of sterile chambers of item 29, wherein the network of sterile chambers includes the manufacture of biologically active products on diagnostic membranes inside a network of sterile chambers includes the printing of biologically active products onto a diagnostic membrane. The diagnostic membrane with the biologically active product may be assembled with a protective covering and/or a device delivery tool for the diagnostic testing, reading of results, and test analysis.

Item 36. The network of sterile chambers of item 29, wherein the network of sterile chambers includes the manufacture of custom filters by printing biologically active products onto filter membranes which are assembled into a completed filtration unit. Bioactive materials such as antibodies may be utilized with a custom filter membrane for the capture and removal or for the capture and elution of a specific material from a filtered fluid.

What is claimed is:

1. A printing system comprising:
a three dimensional printing device having:
   a sterilizable printer assembly including:
      a sterilizable chamber; and
      a multiaxis printing assembly including:
         at least one printing head;
         a plurality of robotic components for positioning the at least one printing head of the multiaxis printing assembly into position over a fixed printing platform and for pushing and/or pulling at least one printing tray across the fixed printing platform along a plurality of tracks;
         a drive mechanism configured to control movements of the robotic components; and
         a central body configured to connect the at least one printing head and the robotic components.

2. The printing system of claim 1, wherein:
the multiaxis printing assembly is a tethered multiaxis printing assembly;
the at least one printing head has a tubing line to a port in the sterilizable chamber for transferring at least one of a fluid and material inputs configured to be dispensed by the at least one printing head, and the three dimensional printing device further comprises an aseptic connector to connect at least one of an external fluid connection and an external material connection to the port in the sterilizable chamber;
the robotic components comprise soft robotic actuators for positioning the tethered multiaxis printing assembly into position over the fixed printing platform,
the drive mechanism is a fluid drive mechanism comprising at least one of an externally-driven hydraulic and pneumatic drive mechanism configured to control the movements of the soft robotic actuators; and
the central body is further configured to connect the at least one printing head and the soft robotic actuators to the tubing line and the fluid drive mechanism, respectively.

3. The printing system of claim 2, wherein:
the soft robotic actuators are selectively curled and uncurled for positioning the printing head and the printing tray relative to one another.

* * * * *